(12) United States Patent
Whitney et al.

(10) Patent No.: US 8,519,125 B2
(45) Date of Patent: Aug. 27, 2013

(54) COMPOSITIONS AND METHODS FOR BIOLOGICAL SAMPLE STORAGE

(75) Inventors: Scott E. Whitney, San Diego, CA (US); Sohela De Rozieres, San Diego, CA (US); Rolf Muller, Del Mar, CA (US)

(73) Assignee: Biomatrica, Inc., San Diego, CA (US)

( * ) Notice: Subject to any disclaimer, the term of this patent is extended or adjusted under 35 U.S.C. 154(b) by 391 days.

(21) Appl. No.: 12/778,100

(22) Filed: May 11, 2010

(65) Prior Publication Data

US 2011/0081363 A1    Apr. 7, 2011

Related U.S. Application Data

(60) Provisional application No. 61/177,161, filed on May 11, 2009.

(51) Int. Cl.
| | | |
|---|---|---|
| C07D 293/10 | (2006.01) | |
| C07D 279/12 | (2006.01) | |
| C07D 265/30 | (2006.01) | |
| C07D 211/00 | (2006.01) | |

(52) U.S. Cl.
USPC ............... 544/1; 544/59; 544/106; 544/242; 546/184

(58) Field of Classification Search
None
See application file for complete search history.

(56) References Cited

U.S. PATENT DOCUMENTS

| | | | |
|---|---|---|---|
| 4,127,502 A | 11/1978 | Li Mutti et al. | 252/408 |
| 4,257,958 A | 3/1981 | Powell | 260/346.7 |
| 4,451,569 A | 5/1984 | Kobayashi et al. | 435/188 |
| 4,806,343 A | 2/1989 | Carpenter et al. | 424/400 |
| 4,891,319 A | 1/1990 | Roser | 435/188 |
| 5,039,704 A | 8/1991 | Smith et al. | 514/563 |
| 5,078,997 A | 1/1992 | Hora et al. | 424/85.2 |
| 5,089,407 A | 2/1992 | Baker et al. | 435/179 |
| 5,240,843 A | 8/1993 | Gibson et al. | 435/188 |
| 5,428,063 A | 6/1995 | Barak et al. | 514/556 |
| 5,496,562 A | 3/1996 | Burgoyne | 424/488 |
| 5,556,771 A | 9/1996 | Shen et al. | 435/91.2 |
| 5,684,045 A | 11/1997 | Smith et al. | 514/563 |
| 5,789,414 A | 8/1998 | Lapidot et al. | 514/256 |
| 5,827,874 A | 10/1998 | Meyer et al. | 514/423 |
| 5,834,254 A | 11/1998 | Shen et al. | 435/91.2 |
| 5,876,992 A | 3/1999 | De Rosier et al. | 435/188 |
| 6,057,159 A | 5/2000 | Lepre | 436/86 |
| 6,143,817 A | 11/2000 | Hallam et al. | 524/514 |
| 6,475,716 B1 | 11/2002 | Seki | 435/1.3 |
| 6,610,531 B1 | 8/2003 | Mateczun et al. | 435/260 |
| 6,689,353 B1 | 2/2004 | Wang et al. | 424/85.2 |
| 6,896,894 B2 | 5/2005 | Brody et al. | 424/425 |
| 7,011,825 B2 | 3/2006 | Yamazaki et al. | 424/85.1 |
| 7,098,033 B2 | 8/2006 | Chen et al. | 435/488 |
| 7,150,980 B1 | 12/2006 | Lapidot et al. | 435/91.1 |
| 7,258,873 B2 | 8/2007 | Truong-Le et al. | 424/489 |
| 2002/0081565 A1 | 6/2002 | Barnea et al. | 435/2 |
| 2003/0022148 A1 | 1/2003 | Seki | 435/1.3 |
| 2003/0138805 A1 | 7/2003 | Loffert et al. | 435/6 |
| 2003/0157088 A1 | 8/2003 | Elliott et al. | 424/94.64 |
| 2003/0175232 A1 | 9/2003 | Elliott et al. | 424/70.14 |
| 2003/0199446 A1 | 10/2003 | Bunger et al. | 514/12 |
| 2005/0196824 A1 | 9/2005 | Fisher et al. | 435/23 |
| 2005/0276728 A1 | 12/2005 | Muller-Cohn et al. | 422/102 |
| 2006/0099567 A1 | 5/2006 | Muller-Cohn et al. | 435/1.1 |
| 2006/0177855 A1 | 8/2006 | Utermohlen et al. | 435/6 |
| 2006/0193968 A1 | 8/2006 | Keogh et al. | 427/2.24 |
| 2006/0293212 A1 | 12/2006 | Griese et al. | 510/446 |
| 2007/0073039 A1 | 3/2007 | Chisari | 530/300 |
| 2008/0176209 A1 | 7/2008 | Muller et al. | 435/2 |
| 2008/0187924 A1 | 8/2008 | Korfhage et al. | 435/6 |
| 2008/0268514 A1 | 10/2008 | Muller et al. | 435/174 |
| 2008/0307117 A1 | 12/2008 | Muller-Cohn et al. | 710/6 |
| 2009/0291427 A1 | 11/2009 | Muller-Cohn et al. | 435/2 |
| 2009/0298132 A1 | 12/2009 | Muller-Cohn et al. | 435/91.51 |

FOREIGN PATENT DOCUMENTS

| | | |
|---|---|---|
| DE | 198 34 816 | 2/2000 |
| EP | 0 448 146 | 9/1991 |
| EP | 0 915 167 | 5/1999 |
| WO | 87/00196 | 1/1987 |
| WO | 89/00012 | 1/1989 |
| WO | 89/06542 | 7/1989 |
| WO | 90/05182 | 5/1990 |
| WO | 91/14773 | 10/1991 |
| WO | 2004/112476 | 12/2004 |
| WO | 2005/113147 | 12/2005 |
| WO | 2007/075253 | 7/2007 |
| WO | 2009/002568 | 12/2008 |
| WO | 2009/009210 | 1/2009 |
| WO | 2009/038853 | 3/2009 |

OTHER PUBLICATIONS

Baskakov et al., "Forcing Thermodynamically Unfolded Proteins to Fold," *The Journal of Biological Chemistry*, 273(9):4831-4834, 1998.

Chen et al., "Stabilization of Recombinant Human Keratinocyte Growth Factor by Osmolytes and Salts," *Journal of Pharmaceutical Sciences*, 85(4):419-426, 1996.

De Sanctis et al., "Influence of Glycerol on the Structure and Redox Properties of Horse Heart Cytochrome c. A Circular Dichroism and Electrochemical Study," *Journal of Protein Chemistry*, 15(7):599-606, 1996.

Frye et al., "The kinetic basis for the stabilization of staphylococcal nuclease by xylose," *Protein Science*, 6:789-793, 1997.

Galinski et al., "1,4,5,6-Tetrahydro-2-methyl-4-pyrimidinecarboxylic acid. A novel cyclic amino acid from halophilic phototrophic bacteria of the genus *Ectothiorhodospira*," *Eur. J. Biochem.*, 149:135-139, 1985.

(Continued)

*Primary Examiner* — James O Wilson
*Assistant Examiner* — Oluwafemi Masha
(74) *Attorney, Agent, or Firm* — Wilson, Sonsini, Goodrich & Rosati

(57) ABSTRACT

Compositions and methods are disclosed for substantially dry storage at ambient or elevated temperatures of biological samples such as nucleic acids, proteins and cells in a form from which the samples can be substantially recovered, using a dissolvable or dissociable dry storage matrix comprising a borate composition and a stabilizer as disclosed, such as any of a number of zwitterionic stabilizers.

5 Claims, 6 Drawing Sheets

(56) References Cited

OTHER PUBLICATIONS

García De Castro et al., "Anhydrobiotic Engineering of Gram-Negative Bacteria," *Applied and Environmental Microbiology*, 66(9):4142-4144, 2000.

Knapp et al., "Extrinsic protein stabilization by the naturally occurring osmolytes βhydroxyectoine and betaine," *Extremophiles*, 3:191-198, 1999.

Kumar et al., "The role of proline in the prevention of aggregation during protein folding in vitro," *Biochemistry and Molecular Biology International*, 46(3):509-517, 1998.

Malin et al., "Effect of Tetrahydropyrimidine Derivatives on Protein-Nucleic Acids Interaction," *The Journal of Biological Chemistry*, 274(11):6920-6929, 1999.

Manzanera et al., "Hydroxyectoine Is Superior to Trehalose for Anhydrobiotic Engineering of *Pseudomonas putida* KT2440," *Applied and Environmental Microbiology*, 68(9):4328-4333, 2002.

Mascellani et al., "Compatible solutes from hyperthermophiles improve the quality of DNA microarrays," *BMC Biotechnology*, 7(82):1-6, 2007.

Parsegian et al., "Macromolecules and Water: Probing with Osmotic Stress," *Methods in Enzymology*, 259:43-94, 1995.

Roberts, "Organic compatible solutes of halotolerant and halophilic microorganisms," *Saline Systems*, 1(5):1-30, 2005.

Sauer et al., "Bacterial Milking: A Novel Bioprocess for Production of Compatible Solutes," *Biotechnology and Bioengineering*, 57(3):306-313, 1998.

Slita et al., "DNA-polycation complexes Effect of polycation structure on physico-chemical and biological properties," *Journal of Biotechnology*, 127:679-693, 2007.

Sola-Penna et al., "Carbohydrate protection of enzyme structure and function against guanidinium chloride treatment depends on the nature of carbohydrate and enzyme," *Eur. J. Biochem.*, 248:24-29, 1997.

Timasheff, "Water as Ligand: Preferential Binding and Exclusion of Denaturants in Protein Unfolding," *Biochemistry*, 31(41):9857-9864, 1992.

Voziyan et al., "Chaperonin-assisted folding of glutamine synthetase under nonpermissive conditions: Off-pathway aggregation propensity does not determine the co-chaperonin requirement," *Protein Science*, 9:2405-2412, 2000.

Wang et al., "A Naturally Occurring Protective System in Urea-Rich Cells: Mechanism of Osmolyte Protection of Proteins against Urea Denaturation," *Biochemistry*, 36:9101-9108, 1997.

Yancey et al., "Living with Water Stress: Evolution of Osmolyte Systems," *Science*, 217:1214-1222, 1982.

Zhi et al., "Renaturation of citrate synthase: Influence of denaturant and folding assistants," *Protein Science*, 1:522-529, 1992.

COMPOSITIONS AND METHODS FOR BIOLOGICAL SAMPLE STORAGE

SEQUENCE LISTING

The instant application contains a Sequence Listing which has been submitted in ASCII format via EFS-Web and is hereby incorporated by reference in its entirety. Said ASCII copy, created on Jul. 1, 2013, is named 35147_706_201_seq.txt and is 864 bytes in size.

TECHNICAL FIELD

The present invention relates generally to improved compositions and methods for biological sample protection, storage, and retrieval. The invention also relates to the use, storage, retrieval and analysis of such biological materials and samples.

BACKGROUND OF THE INVENTION

Research in the life sciences field is based upon the analysis of biological materials and samples, such as DNA, RNA, blood, urine, feces, buccal swabs or samples, bacteria, archaebacteria, viruses, phage, plants, algae, yeast, microorganisms, PCR products, cloned DNA, proteins, enzymes, peptides, prions, eukaryotes (e.g. protoctisca, fungi, plantae and animalia), prokaryotes, cells and tissues, germ cells (e.g. sperm and oocytes), stem cells, vaccines, and of minerals or chemicals. Such samples are typically collected or obtained from appropriate sources and placed into storage and inventory for further processing and analysis. Oftentimes, transportation of samples is required, and attention is given to preserve their integrity, sterility and stability. Biological samples can be transported in a refrigerated environment using ice, dry ice or other freezing facility. However, adequate low temperatures often cannot conveniently be maintained for extended time periods such as those required for transportation within or between countries or continents, particularly where an energy source for the refrigeration device is lacking.

Storage containers or storage vessels for such samples include bottles, tubes, vials, bags, boxes, racks, multi-well dishes and multi-well plates, which are typically sealed by individual screw caps or snap caps, snap or seal closures, lids, adhesive strips or tape, multi-cap strips, or other means for containing such samples. The standard container format for medium to high throughput of sample storage, processing and automation of biological processes is a 96-, 384-, or 1536-well plate or array. The containers and the samples contained therein are stored at various temperatures, for example at ambient temperature or at 4° C. or at temperatures below 0° C., typically at about −20° C. or at −70° C. to −80° C. The samples that are placed and stored in the devices are most frequently contained in liquid medium or a buffer solution, and they require storage at such subzero temperatures (e.g., −20° C. or −70 to −80° C.). In some cases, samples are first dried and then stored at ambient temperature, or at 4° C., at −20° C. or at −70 to −80° C.

For example, presently, nucleic acids are stored in liquid form at low temperatures. For short term storage, nucleic acids can be stored at 4° C. For longterm storage the temperature is generally lowered to −20° C. to −70° C. to prevent degradation of the genetic material, particularly in the case of genomic DNA and RNA. Nucleic acids are also stored at room temperature on solid matrices such as cellulose membranes. Both storage systems are associated with disadvantages. Storage under low temperature requires costly equipment such as cold rooms, freezers, and/or electric generator back-up systems; such equipment can be unreliable in cases of unexpected power outage or may be difficult to use in areas without a ready source of electricity or having unreliable electric systems. The storage of nucleic acids on cellulose fibers also results in a substantial loss of material during the rehydration process, since the nucleic acid stays trapped by, and hence associated with, the cellulose fibers instead of being quantitatively recoverable. Nucleic acid dry storage on cellulose also requires the separation of the cellulose from the biological material, since the cellulose fibers otherwise contaminate the biological samples. The separation of the nucleic acids from cellulose filters requires additional handling, including steps of pipetting, transferring of the samples into new tubes or containers, and centrifugation, all of which can result in reduced recovery yields and increased opportunity for the introduction of unwanted contaminants or exposure to conditions that promote sample degradation, and which are also cost- and labor-intensive.

Proteins are presently handled primarily in liquid stages, in cooled or frozen environments typically ranging from −20° C. to storage in liquid nitrogen. In some exceptions proteins may be freeze-dried, or dried at room temperature, for example, in the presence of trehalose and applied directly to an untreated surface. (Garcia de Castro et al., 2000 *Appl. Environ. Microbiol.* 66:4142; Manzanera et al., 2002 *Appl. Environ. Microbiol.* 68:4328) Proteins often degrade and/or lose activity even when stored cooled (4° C.), or frozen (−20° C. or −80° C.). The freeze-thaw stress on proteins reduces bioactivity (e.g., enzymatic activity, specific binding to a cognate ligand, etc.) especially if repeated freeze-thawing of aliquots of a protein sample is required. The consequent loss of protein activity that may be needed for biological assays typically requires the readjustment of the protein concentration in order to obtain comparable assay results, or costly rejection of compromised protein reagents in favor of procuring new lots. The common practice of having multiple users of enzyme reagents stored in a laboratory, especially by different users at different times and employing non-standardized handling procedures, further reduces the reliability of experimental data generated with such reagents. As a result, the half-life of proteins is reduced and expensive reagents have to be replaced frequently, amounting to enormous financial costs to the user. For the supplier of the proteins, high costs are required to maintain an undisrupted frozen supply chain starting with initial cold room work-ups, for shipment, frozen storage of the sample, and frozen transport of the protein from production to the site of use. For example, delays during shipment can result in inactivation of proteins, which then have to be replaced at great cost to the supplier; receipt of inactive product can also result in dissatisfied customers.

Drying of proteins and nucleic acids has yet to be universally adopted by the research scientific, biomedical, biotechnology and other industrial business communities because of the lack of standard established and reliable processes, difficulties with recoveries of functional properties and with quantitative recoveries of biological sample material, variable buffer and solvent compatibilities and tolerances, and other difficulties arising from the demands of handling nucleic acids and proteins. The same problems apply to the handling, storage, and use of other biological materials, such as viruses, phage, bacteria, cells and multicellular organisms. See, e.g., Roberts, 2005 *Saline Systems* 1:5; Galinski et al., 1985 *Eur. J. Biochem.* 149:135; Malin et al., 1999 *J. Biol. Chem.* 274:6920; Mascellani et al., 2007 *BMC Biotechnol.* 7:82. Disaccharides such as trehalose or lactitol, for example, have been described as additives for dry storage of protein-containing samples (e.g., U.S. Pat. No. 4,891,319; U.S. Pat. No. 5,834,254; U.S. Pat. No. 6,896,894; U.S. Pat. No. 5,876,992; U.S. Pat. No. 5,240,843; WO 90/05182; WO 91/14773) but usefulness of such compounds in the described contexts has been compromised by their serving as energy sources for undesirable microbial contaminants, by their limited stabilizing effects when used as described, by their lack of general applicability across a wide array of biological samples, and by other factors.

The genomic age and the recent deciphering of the human and many other genomes, proteomes, transcriptomes, etc. have led to the industrialization of life sciences research. Millions of biological samples including genes and/or gene products from a multitude of organisms are being analyzed in order to advance scientific knowledge and develop commercial products. The development of high throughput technologies has resulted in a vast pool of information and samples, such that there is an increasing need to store these samples for analysis at a later timepoint. Typically samples that may be tested at later times are stored frozen in freezers at −20° C. to −80° C. However with the rapid expansion of demand and capability for analyzing samples by techniques such as polymerase chain reaction (PCR), nucleic acid sequencing, single nucleotide polymorphism (SNP) analyses and other biochemical and/or molecular biology techniques, the available space for storing these samples is rapidly diminishing. Also, universities and other research institutions, reference and diagnostic laboratories and the like are beginning to recognize that the electricity demands for such frozen storage capabilities are constantly growing. Hence, and as the energy pricing rates rise concomitantly, the long term sustainability of this approach is being questioned. It is apparent that a long term sustainable solution to sample storage is vital to the research and diagnostic communities. Clearly there is a need in the industry for convenient, low-cost, energy efficient and accessible life sciences sample storage and retrieval systems. The present disclosure addresses such needs by providing compositions and methods for stably and recoverably storing biological samples such as DNA, RNA and proteins obtained from various biological sources, under anhydrobiotic conditions at room temperature, and offers other related advantages.

SUMMARY OF THE INVENTION

According to certain embodiments of the present invention there is provided a matrix for substantially dry storage of a biological sample, comprising (a) a borate composition; and (b) at least one stabilizer that is selected from (i) a compound of formula I:

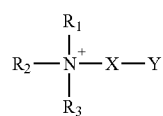

(I)

wherein $R_1$, $R_2$, $R_3$ are independently selected from aryl, arylalkyl, —H, —$CH_3$ and —$CH_2$—$CH_3$, wherein when $R_1$ and $R_2$ are $CH_3$ or $CH_2$—$CH_3$, $R_3$ is either H or absent, wherein X is selected from —$CH_2$—, —$CH_2CH_2$—, —$CH_2CH_2CH_2$—, —$CH_2CH_2CH_2CH_2$—,

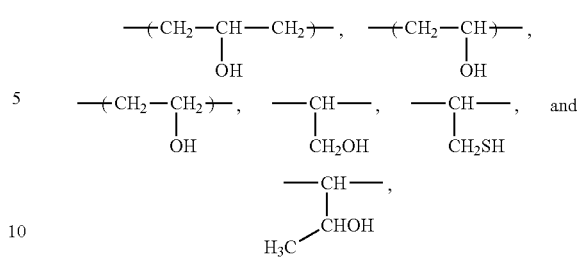

and wherein Y is selected from $COO^-$ and $SO_3^-$;

(ii) a compound of formula II:

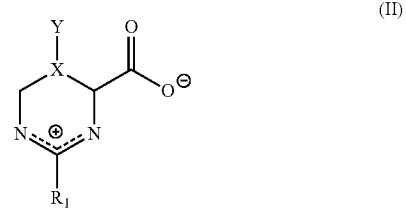

(II)

wherein $R_1$ is selected from $CH_3$ and $CH_2CH_3$, and wherein when X is CH, Y is selected from H and OH, and when X is $CH_2$—CH, Y is H;

(iii) a compound of formula III:

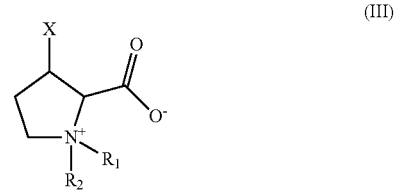

(III)

wherein $R_1$ and $R_2$ are independently selected from —H, —$CH_3$, and —$CH_2CH_3$, and wherein X is selected from H, OH and SH;

(iv) a compound of formula IV:

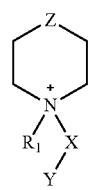

(IV)

wherein $R_1$ is selected from aryl, arylalkyl, —H, —$CH_3$— $CH_2$—$CH_3$, —$CH_2CH_2OH$, $CH_2CHOHCH_3$, $CH_2CHOHCH_2OH$, and $CH_2CH_2CH_2OH$, wherein X is selected from —$CH_2$—, —$CH_2CH_2$—, —$CH_2CHOH$, —$CH_2CH_2CH_2$—, $CH_2CH_2CH_2CH_2$, $CH_2CHOHCH_2$ and —$CH_2CHOHCHOHCH_2$—, wherein Y is selected from $COO^-$ and $SO_3^-$, and wherein Z is selected from —$CH_2$—, —CHOH—, O and S;

(v) a compound of formula V:

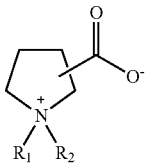

wherein $R_1$ and $R_2$ are each independently selected from aryl, arylalkyl, —H, —CH$_3$—CH$_2$—CH$_3$, —CH$_2$CH$_2$OH, CH$_2$CHOHCH$_3$, CH$_2$CHOHCH$_2$OH; and CH$_2$CH$_2$CH$_2$OH;

(vi) a compound of formula VI:

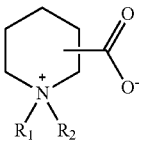

wherein $R_1$ and $R_2$ are each independently selected from aryl, arylalkyl, —H, —CH$_3$—CH$_2$—CH$_3$, —CH$_2$CH$_2$OH, CH$_2$CHOHCH$_3$, CH$_2$CHOHCH$_2$OH, and CH$_2$CH$_2$CH$_2$OH;

(vii) a compound of formula VII:

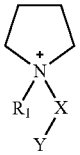

wherein $R_1$ is selected from aryl, arylalkyl, —H, —CH$_3$—CH$_2$—CH$_3$, —CH$_2$CH$_2$OH, CH$_2$CHOHCH$_3$, CH$_2$CHOHCH$_2$OH, and CH$_2$CH$_2$CH$_2$OH, wherein X is selected from —CH$_2$—, —CH$_2$CH$_2$—, —CH$_2$CHOH, —CH$_2$CH$_2$CH$_2$—, —CH$_2$CH$_2$CH$_2$CH$_2$—, —CH$_2$CHOHCH$_2$—, and —CH$_2$CHOHCHOHCH$_2$—, wherein Y is selected from CO$_2$ and SO$_3$—, and wherein Z is selected from CH$_2$, CHOH, O and S; and (viii) an osmoprotectant compound that is selected from trimethylammonium acetate, glycerol phosphate, diglycerol phosphate, N-(2-hydroxy-1,1-bis(hydroxymethyl)ethyl)glycine (tricine), 3-(N-morpholino)-2-hydroxypropanesulfonic acid (MOPSO), pentaerythritol, glyceric acid, malic acid, tartaric acid, lactic acid, glycolic acid, 2-hydroxybutyric acid, 3-hydroxybutyric acid, 4-amino-3-hydroxybutyric acid, 3-(1-azoniabicyclo[2.2.2]oct-1-yl)propane-1-sulfonate, and 1-(2-carboxylatoethyl)-1-azabicyclo[2.2.2]octan-1-ium, wherein the borate composition and the stabilizer are present at a molar ratio that is selected from a molar ratio of from about 10:1 to about 1:10, a molar ratio of from about 5:1 to about 1:5, and a molar ratio of from about 20:1 to about 1:20, and wherein the matrix is capable of preventing degradation of an isolated DNA fragment of at least 10 kilobases during substantially dry storage of the DNA fragment in the matrix at 85° C. for a time period of at least two weeks.

In certain embodiments the time period is selected from at least four weeks, at least eight weeks, at least 12 weeks, at least 16 weeks, at least 20 weeks, at least 24 weeks, at least 30 weeks, at least 36 weeks, at least 40 weeks, at least 48 weeks, and at least one year. In certain embodiments the borate composition comprises at least one compound selected from boric acid, dihydrogen borate, hydrogen borate, diborate, triborate, tetraborate, metaborate, hydroxoborate (borax), borate salt, boric acid-glycerol, boric anhydride (B$_2$O$_3$) and boric-acid-1,3 propanediol. In certain embodiments the stabilizer is selected from hydroxyectoine, ectoine, homoectoine, betaine, L-carnitine, sarcosine, N,N-dimethylglycine, triethylammonium acetate, glycerol phosphate, N-(2-Hydroxy-1,1-bis(hydroxymethyl)ethyl)glycine (tricine), 3-(N-Morpholino)-2-hydroxypropanesulfonic acid (MOPSO), pentaerythritol, N-ethyl-N,N-bis-(2-hydroxyethyl)ammonium-N-4-butyl sulfonate, glycolic acid, lactic acid, malic acid, tartaric acid, 2-hydroxybutyric acid, 3-hydroxybutyric acid, 4-amino-3-hydroxybutyric acid, pyridine 2,5-dicarboxylic acid, 3-(1-azoniabicyclo[2.2.2]oct-1-yl)propane-1-sulfonate, 1-(2-carboxylatoethyl)-1-azabicyclo[2.2.2]octan-1-ium, and 4-[benzyl(2-hydroxyethyl)methylazaniumyl]butane-1-sulfonate.

In certain embodiments the matrix further comprises a chelator, which in certain embodiments is selected from ethylenediaminetetraacetic acid (EDTA), ethylene glycol tetraacetic acid (EGTA), diethylenetriaminepentaacetic acid (DTPA), trans-1,2-diaminocyclohexane-N,N,N',N'-tetraacetic acid (CDTA), 1,2-bis(2-aminophenoxy)ethane-N,N,N',N'-tetraacetic acid (BAPTA), 1,4,7,10-tetraazacyclododecane-1,4,7,10-tetraacetic acid (DOTA), N-(2-hydroxyethyl)ethylenediamine-N,N',N'-triacetic acid, and nitrilotriacetic acid (NTA). In certain embodiments the matrix dissolves or dissociates in a biocompatible solvent. In certain embodiments the matrix dissolves in a biocompatible solvent. In certain embodiments the biocompatible solvent comprises water. In certain embodiments the biocompatible solvent comprises a pH buffer. In certain embodiments the pH buffer is selected from Tris, citrate, acetate, phosphate, borate, CAPS, CAPSO, HEPES, MES, MOPS, MOPSO, PIPES, carbonate and bicarbonate. In certain embodiments the matrix further comprises a biological inhibitor or a biochemical inhibitor.

In another embodiment there is provided a matrix for substantially dry storage of a biological sample, comprising (a) a borate composition which comprises at least one compound selected from boric acid, boric anhydride, dihydrogen borate, hydrogen borate, diborate, triborate, tetraborate, metaborate, hydroxoborate (borax), borate salt, boric acid-glycerol and boric-acid-1,3 propanediol; (b) at least one stabilizer that is selected from: (i) a compound of formula I:

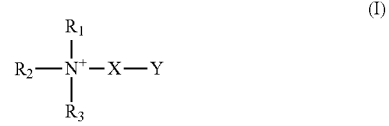

wherein $R_1$, $R_2$, $R_3$ are independently selected from aryl, arylalkyl, —H, —CH$_3$ and —CH$_2$—CH$_3$, wherein when $R_1$ and $R_2$ are CH$_3$ or CH$_2$—CH$_3$, $R_3$ is either H or absent, wherein X is selected from —CH$_2$—, —CH$_2$CH$_2$—, —CH$_2$CH$_2$CH$_2$—, —CH$_2$CH$_2$CH$_2$CH$_2$—,

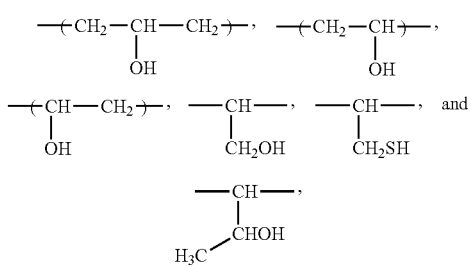

and wherein Y is selected from COO⁻ and SO₃⁻;

(ii) a compound of formula II:

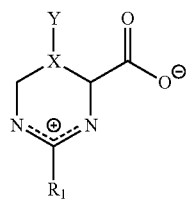

wherein $R_1$ is selected from $CH_3$ and $CH_2CH_3$, and wherein when X is CH, Y is selected from H and OH, and when X is $CH_2$—CH, Y is H;

(iii) a compound of formula III:

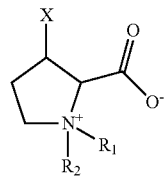

wherein $R_1$ and $R_2$ are independently selected from —H, —$CH_3$, and —$CH_2CH_3$, and wherein X is selected from H, OH and SH;

(iv) a compound of formula IV:

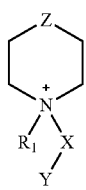

wherein $R_1$ is selected from aryl, arylalkyl, —H, —$CH_3$—$CH_2$—$CH_3$, —$CH_2CH_2OH$, $CH_2CHOHCH_3$, $CH_2CHOHCH_2OH$, and $CH_2CH_2CH_2OH$, wherein X is selected from —$CH_2$—, —$CH_2CH_2$—, —$CH_2CHOH$, —$CH_2CH_2CH_2$—, $CH_2CH_2CH_2CH_2$, $CH_2CHOHCH_2$ and —$CH_2CHOHCHOHCH_2$—, wherein Y is selected from COO⁻ and SO₃⁻, and wherein Z is selected from —$CH_2$—, —CHOH—, O and S;

(v) a compound of formula V:

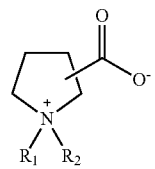

wherein $R_1$ and $R_2$ are each independently selected from aryl, arylalkyl, —H, —$CH_3$—$CH_2$—$CH_3$, —$CH_2CH_2OH$, $CH_2CHOHCH_3$, $CH_2CHOHCH_2OH$; and $CH_2CH_2CH_2OH$, (vi) a compound of formula VI:

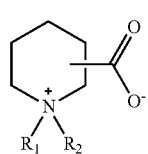

wherein $R_1$ and $R_2$ are each independently selected from aryl, arylalkyl, —H, —$CH_3$—$CH_2$—$CH_3$, —$CH_2CH_2OH$, $CH_2CHOHCH_3$, $CH_2CHOHCH_2OH$, and $CH_2CH_2CH_2OH$;

(vii) a compound of formula VII:

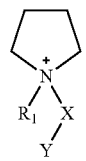

wherein $R_1$ is selected from aryl, arylalkyl, —H, —$CH_3$—$CH_2$—$CH_3$, —$CH_2CH_2OH$, $CH_2CHOHCH_3$, $CH_2CHOHCH_2OH$, and $CH_2CH_2CH_2OH$, wherein X is selected from —$CH_2$—, —$CH_2CH_2$—, —$CH_2CHOH$, —$CH_2CH_2CH_2$—, —$CH_2CH_2CH_2CH_2$—, —$CH_2CHOHCH_2$—, and —$CH_2CHOHCHOHCH_2$—, wherein Y is selected from $CO_2^-$ and $SO_3^-$, and wherein Z is selected from $CH_2$, CHOH, O and S; and (viii) an osmoprotectant compound that is selected from trimethylammonium acetate, glycerol phosphate, diglycerol phosphate, N-(2-hydroxy-1,1-bis(hydroxymethyl)ethyl)glycine (tricine), 3-(N-morpholino)-2-hydroxypropanesulfonic acid (MOPSO), pentaerythritol, glyceric acid, malic acid, tartaric acid, lactic acid, glycolic acid, 2-hydroxybutyric acid, 3-hydroxybutyric acid, 4-amino-3-hydroxybutyric acid, 3-(1-azoniabicyclo[2.2.2]oct-1-yl)propane-1-sulfonate, and 1-(2-carboxylatoethyl)-1-azabicyclo[2.2.2]octan-1-ium, wherein the borate composition and the stabilizer are present at a molar ratio that is selected from a molar ratio of from about 10:1 to about 1:10, a molar ratio of from about 5:1 to about 1:5, and a molar ratio of from about 20:1 to about 1:20, and wherein the matrix is capable of preventing degradation of an isolated DNA fragment of at least 10 kilobases during substantially dry storage of the DNA fragment in the matrix at 85° C. for a time period of at least two weeks.

According to certain further embodiments the biological sample comprises at least one of (i) an isolated biomolecule that is selected from the group consisting of a nucleic acid, a protein, a polypeptide, a lipid, a glycoconjugate, an oligosaccharide, and a polysaccharide, and (ii) a biological material that is selected from the group consisting of a mammalian cell, a bacterium, a yeast cell, a virus, a vaccine, blood, urine, a biological fluid, and a buccal swab. In certain embodiments the biological sample comprises at least one isolated nucleic acid that is selected from DNA and RNA. In certain embodiments the biological inhibitor or biochemical inhibitor is selected from the group consisting of a reducing agent, an alkylating agent, an antifungal agent and an antimicrobial agent. In certain embodiments the matrix comprises at least one detectable indicator, which in certain further embodiments comprises a dye or a colorimetric indicator, and in certain other further embodiments is selected from phenol red, ethidium bromide, a DNA polymerase, a restriction endonuclease, cobalt chloride, Reichardt's dye and a fluorogenic protease substrate.

In another embodiment the present invention provides a method of storing a biological sample, comprising contacting a biological sample with a matrix for substantially dry storage of a biological sample, the matrix comprising (a) a borate composition; and (b) at least one stabilizer that is selected from: (i) a compound of formula I:

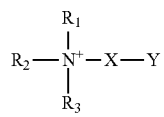
(I)

wherein $R_1$, $R_2$, $R_3$ are independently selected from aryl, arylalkyl, —H, —CH$_3$ and —CH$_2$—CH$_3$, wherein when $R_1$ and $R_2$ are CH$_3$ or CH$_2$—CH$_3$, $R_3$ is either H or absent, wherein X is selected from —CH$_2$—, —CH$_2$CH$_2$—, —CH$_2$CH$_2$CH$_2$—, —CH$_2$CH$_2$CH$_2$CH$_2$—,

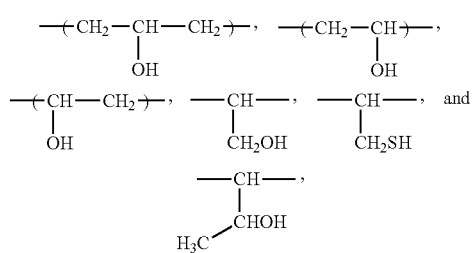

and wherein Y is selected from COO$^-$ and SO$_3^-$;

(ii) a compound of formula II:

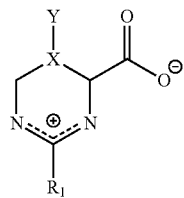
(II)

wherein $R_1$ is selected from CH$_3$ and CH$_2$CH$_3$, and wherein when X is CH, Y is selected from H and OH, and when X is CH$_2$—CH, Y is H;

(iii) a compound of formula III:

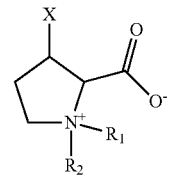
(III)

wherein $R_1$ and $R_2$ are independently selected from —H, —CH$_3$, and —CH$_2$CH$_3$, and wherein X is selected from H, OH and SH;

(iv) a compound of formula IV:

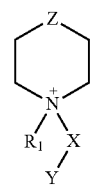
(IV)

wherein $R_1$ is selected from aryl, arylalkyl, —H, —CH$_3$—CH$_2$—CH$_3$, —CH$_2$CH$_2$OH, CH$_2$CHOHCH$_3$, CH$_2$CHOHCH$_2$OH, and CH$_2$CH$_2$CH$_2$OH, wherein X is selected from —CH$_2$—, —CH$_2$CH$_2$—, —CH$_2$CHOH, —CH$_2$CH$_2$CH$_2$—, CH$_2$CH$_2$CH$_2$CH$_2$, CH$_2$CHOHCH$_2$ and —CH$_2$CHOHCHOHCH$_2$—, wherein Y is selected from COO$^-$ and SO$_3^-$, and wherein Z is selected from —CH$_2$—, —CHOH—, O and S;

(v) a compound of formula V:

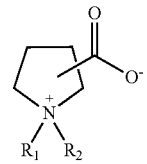
(V)

wherein $R_1$ and $R_2$ are each independently selected from aryl, arylalkyl, —H, —CH$_3$—CH$_2$—CH$_3$, —CH$_2$CH$_2$OH, CH$_2$CHOHCH$_3$, CH$_2$CHOHCH$_2$OH; and CH$_2$CH$_2$CH$_2$OH, (vi) a compound of formula VI:

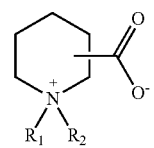
(VI)

wherein $R_1$ and $R_2$ are each independently selected from aryl, arylalkyl, —H, —CH$_3$—CH$_2$—CH$_3$, —CH$_2$CH$_2$OH, CH$_2$CHOHCH$_3$, CH$_2$CHOHCH$_2$OH, and CH$_2$CH$_2$CH$_2$OH;

(vii) a compound of formula VII:

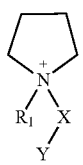

(VII)

wherein $R_1$ is selected from aryl, arylalkyl, —H, —$CH_3$—$CH_2$—$CH_3$, —$CH_2CH_2OH$, $CH_2CHOHCH_3$, $CH_2CHOHCH_2OH$, and $CH_2CH_2CH_2OH$, wherein X is selected from —$CH_2$—, —$CH_2CH_2$—, —$CH_2CHOH$, —$CH_2CH_2CH_2$—, —$CH_2CH_2CH_2CH_2$—, —$CH_2CHOHCH_2$—, and —$CH_2CHOHCHOHCH_2$—, wherein Y is selected from $CO_2^-$ and $SO_3^-$, and wherein Z is selected from $CH_2$, CHOH, O and S; and (viii) an osmoprotectant compound that is selected from trimethylammonium acetate, glycerol phosphate, diglycerol phosphate, N-(2-hydroxy-1,1-bis(hydroxymethyl)ethyl)glycine (tricine), 3-(N-morpholino)-2-hydroxypropanesulfonic acid (MOPSO), pentaerythritol, glyceric acid, malic acid, tartaric acid, lactic acid, glycolic acid, 2-hydroxybutyric acid, 3-hydroxybutyric acid, 4-amino-3-hydroxybutyric acid, 3-(1-azoniabicyclo[2.2.2]oct-1-yl)propane-1-sulfonate, and 1-(2-carboxylatoethyl)-1-azabicyclo[2.2.2]octan-1-ium, wherein the borate composition and the stabilizer are present at a molar ratio that is selected from a molar ratio of from about 10:1 to about 1:10, a molar ratio of from about 5:1 to about 1:5, and a molar ratio of from about 20:1 to about 1:20, and wherein the matrix is capable of preventing degradation of an isolated DNA fragment of at least 10 kilobases during substantially dry storage of the DNA fragment in the matrix at 85° C. for a time period of at least two weeks In certain embodiments the method comprises maintaining the matrix without refrigeration subsequent to the step of contacting. In certain embodiments the method comprises substantially drying the matrix, and thereby storing the biological sample. In certain further embodiments the method comprises maintaining the matrix without refrigeration subsequent to the steps of contacting and drying. In certain embodiments the time period is selected from at least four weeks, at least eight weeks, at least 12 weeks, at least 16 weeks, at least 20 weeks, at least 24 weeks, at least 30 weeks, at least 36 weeks, at least 40 weeks, at least 48 weeks, and at least one year. In certain embodiments the borate composition comprises at least one compound selected from boric acid, dihydrogen borate, hydrogen borate, diborate, triborate, tetraborate, metaborate, hydroxoborate (borax), borate salt, boric acid-glycerol, boric anhydride ($B_2O_3$) and boric-acid-1,3 propanediol. In certain embodiments the stabilizer is selected from hydroxyectoine, ectoine, homoectoine, betaine, L-carnitine, sarcosine, N,N-dimethylglycine, triethylammonium acetate, glycerol phosphate, N-(2-Hydroxy-1,1-bis(hydroxymethyl)ethyl)glycine (tricine), 3-(N-Morpholino)-2-hydroxypropanesulfonic acid (MOPSO), pentaerythritol, N-ethyl-N,N-bis-(2-hydroxyethyl)ammonium-N-4-butyl sulfonate, glycolic acid, lactic acid, malic acid, tartaric acid, 2-hydroxybutyric acid, 3-hydroxybutyric acid, 4-amino-3-hydroxybutyric acid, pyridine 2,5-dicarboxylic acid, 3-(1-azoniabicyclo[2.2.2]oct-1-yl)propane-1-sulfonate, 1-(2-carboxylatoethyl)-1-azabicyclo[2.2.2]octan-1-ium, and 4-[benzyl(2-hydroxyethyl)methylazaniumyl]butane-1-sulfonate. In certain embodiments the matrix further comprises a chelator, which in certain further embodiments is selected from EDTA, EGTA, DTPA, CDTA, BAPTA, DOTA, N-(2-hydroxyethyl)ethylenediamine-N,N', N'-triacetic acid, and NTA. In certain embodiments the matrix dissolves or dissociates in a biocompatible solvent. In certain embodiments the matrix dissolves in a biocompatible solvent. In certain embodiments the biocompatible solvent comprises water, and in certain further embodiments the biocompatible solvent comprises a pH buffer, which in certain further embodiments is selected from the Tris, citrate, acetate, phosphate, borate, CAPS, CAPSO, HEPES, MES, MOPS, MOPSO, PIPES, carbonate and bicarbonate. In certain embodiments of the herein described method, the matrix further comprises a biological inhibitor or a biochemical inhibitor.

In certain embodiments of the above described method, the matrix comprises (a) a borate composition which comprises at least one compound selected from boric acid, boric anhydride, dihydrogen borate, hydrogen borate, diborate, triborate, tetraborate, metaborate, hydroxoborate (borax), borate salt, boric acid-glycerol and boric-acid-1,3 propanediol; (b) at least one stabilizer that is selected from: (i) a compound of formula I:

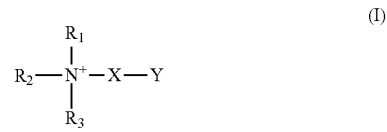

(I)

wherein $R_1$, $R_2$, $R_3$ are independently selected from aryl, arylalkyl, —H, —$CH_3$ and —$CH_2$—$CH_3$, wherein when $R_1$ and $R_2$ are $CH_3$ or $CH_2$—$CH_3$, $R_3$ is either H or absent, wherein X is selected from —$CH_2$—, —$CH_2CH_2$—, —$CH_2CH_2CH_2$—, —$CH_2CH_2CH_2CH_2$—,

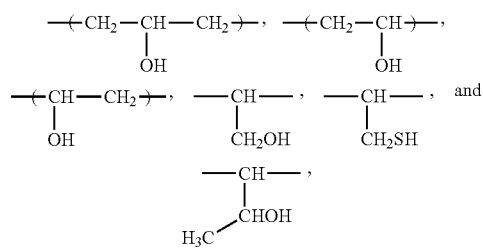

and wherein Y is selected from $COO^-$ and $SO_3^-$;
(ii) a compound of formula II:

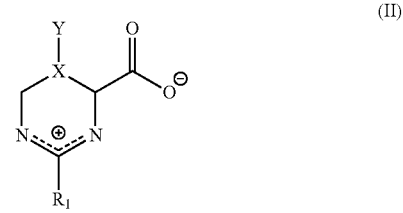

(II)

wherein $R_1$ is selected from $CH_3$ and $CH_2CH_3$, and wherein when X is CH, Y is selected from H and OH, and when X is $CH_2$—CH, Y is H;

(iii) a compound of formula III:

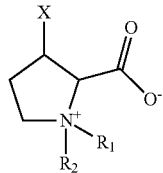

(III)

wherein $R_1$ and $R_2$ are independently selected from —H, —$CH_3$, and —$CH_2CH_3$, and wherein X is selected from H, OH and SH;

(iv) a compound of formula IV:

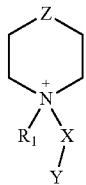

(IV)

wherein $R_1$ is selected from aryl, arylalkyl, —H, —$CH_3$—$CH_2$—$CH_3$, —$CH_2CH_2OH$, $CH_2CHOHCH_3$, $CH_2CHOHCH_2OH$, and $CH_2CH_2CH_2OH$, wherein X is selected from —$CH_2$—, —$CH_2CH_2$—, —$CH_2CHOH$, —$CH_2CH_2CH_2$—, $CH_2CH_2CH_2CH_2$, $CH_2CHOHCH_2$ and —$CH_2CHOHCHOHCH_2$—, wherein Y is selected from $COO^-$ and $SO_3^-$, and wherein Z is selected from —$CH_2$—, —CHOH—, O and S;

(v) a compound of formula V:

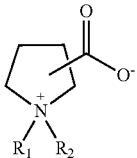

(V)

wherein $R_1$ and $R_2$ are each independently selected from aryl, arylalkyl, —H, —$CH_3$—$CH_2$—$CH_3$, —$CH_2CH_2OH$, $CH_2CHOHCH_3$, $CH_2CHOHCH_2OH$; and $CH_2CH_2CH_2OH$, (vi) a compound of formula VI:

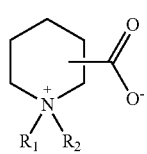

(VI)

wherein $R_1$ and $R_2$ are each independently selected from aryl, arylalkyl, —H, —$CH_3$—$CH_2$—$CH_3$, —$CH_2CH_2OH$, $CH_2CHOHCH_3$, $CH_2CHOHCH_2OH$, and $CH_2CH_2CH_2OH$;

(vii) a compound of formula VII:

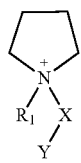

(VII)

wherein $R_1$ is selected from aryl, arylalkyl, —H, —$CH_3$—$CH_2$—$CH_3$, —$CH_2CH_2OH$, $CH_2CHOHCH_3$, $CH_2CHOHCH_2OH$, and $CH_2CH_2CH_2OH$, wherein X is selected from —$CH_2$—, —$CH_2CH_2$—, —$CH_2CHOH$, —$CH_2CH_2CH_2$—, —$CH_2CH_2CH_2CH_2$—, —$CH_2CHOHCH_2$—, and —$CH_2CHOHCHOHCH_2$—, wherein Y is selected from $CO_2^-$ and $SO_3^-$, and wherein Z is selected from $CH_2$, CHOH, O and S; and (viii) an osmoprotectant compound that is selected trimethylammonium acetate, glycerol phosphate, diglycerol phosphate, N-(2-hydroxy-1,1-bis(hydroxymethyl)ethyl)glycine (tricine), 3-(N-morpholino)-2-hydroxypropanesulfonic acid (MOPSO), pentaerythritol, glyceric acid, malic acid, tartaric acid, lactic acid, glycolic acid, 2-hydroxybutyric acid, 3-hydroxybutyric acid, 4-amino-3-hydroxybutyric acid, 3-(1-azoniabicyclo [2.2.2]oct-1-yl)propane-1-sulfonate, and 1-(2-carboxylatoethyl)-1-azabicyclo[2.2.2]octan-1-ium, wherein the borate composition and the stabilizer are present at a molar ratio that is selected from a molar ratio of from about 10:1 to about 1:10, a molar ratio of from about 5:1 to about 1:5, and a molar ratio of from about 20:1 to about 1:20, and wherein the matrix is capable of preventing degradation of an isolated DNA fragment of at least 10 kilobases during substantially dry storage of the DNA fragment in the matrix at 85° C. for a time period of at least two weeks. In certain embodiments the biological sample comprises at least one of (i) an isolated biomolecule that is selected from a nucleic acid, a protein, a polypeptide, a lipid, a glycoconjugate, an oligosaccharide, and a polysaccharide, and (ii) a biological material that is selected from a mammalian cell, a bacterium, a yeast cell, a virus, a vaccine, blood, urine, a biological fluid, and a buccal swab. In certain embodiments the biological sample comprises at least one isolated nucleic acid that is selected from DNA and RNA. In certain embodiments the biological inhibitor or biochemical inhibitor is selected from a reducing agent, an alkylating agent, an antifungal agent and an antimicrobial agent. In certain embodiments the matrix further comprises at least one detectable indicator, which in certain further embodiments comprises a dye or a colorimetric indicator. In certain embodiments the detectable indicator is selected from phenol red, ethidium bromide, a DNA polymerase, a restriction endonuclease, cobalt chloride, Reichardt's dye and a fluorogenic protease substrate.

In certain embodiments of the above described methods, biological activity of the sample subsequent to the step of maintaining is substantially the same as biological activity of the sample prior to the step of contacting. In certain embodiments of the above described methods, degradation of the biological sample is decreased relative to degradation of a control biological sample maintained without refrigeration in the absence of the matrix material. In certain embodiments of the above described methods, the method is selected from (i) the method wherein the step of contacting comprises simultaneously dissolving or dissociating the matrix material in a solvent, (ii) the method wherein the step of contacting is preceded by dissolving or dissociating the matrix material in a solvent, and (iii) the method wherein the step of contacting is followed by dissolving or dissociating the matrix material in a solvent.

In another embodiment of the present invention, there is provided a method of preparing a biological sample storage device for one or a plurality of biological samples, comprising (a) administering a matrix to one or a plurality of sample wells of a biological sample storage device, wherein (1) said biological sample storage device comprises a sample plate comprising one or a plurality of sample wells that are capable of containing a biological sample, and wherein (2) the matrix comprises (a) a borate composition; and (b) at least one stabilizer that is selected from: (i) a compound of formula I:

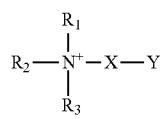
(I)

wherein $R_1$, $R_2$, $R_3$ are independently selected from aryl, arylalkyl, —H, —$CH_3$ and —$CH_2$—$CH_3$, wherein when $R_1$ and $R_2$ are $CH_3$ or $CH_2$—$CH_3$, $R_3$ is either H or absent, wherein X is selected from —$CH_2$—, —$CH_2CH_2$—, —$CH_2CH_2CH_2$—, —$CH_2CH_2CH_2CH_2$—,

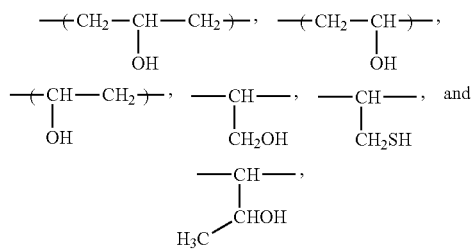

and wherein Y is selected from $COO^-$ and $SO_3^-$;

(ii) a compound of formula II:

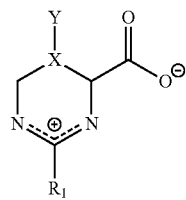
(II)

wherein $R_1$ is selected from $CH_3$ and $CH_2CH_3$, and wherein when X is CH, Y is selected from H and OH, and when X is $CH_2$—CH, Y is H;

(iii) a compound of formula III:

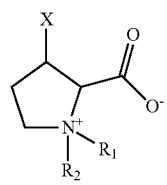
(III)

wherein $R_1$ and $R_2$ are independently selected from —H, —$CH_3$, and —$CH_2CH_3$, and wherein X is selected from H, OH and SH;

(iv) a compound of formula IV:

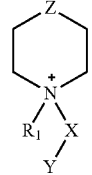
(IV)

wherein $R_1$ is selected from aryl, arylalkyl, —H, —$CH_3$—$CH_2$—$CH_3$, —$CH_2CH_2OH$, $CH_2CHOHCH_3$, $CH_2CHOHCH_2OH$, and $CH_2CH_2CH_2OH$, wherein X is selected from —$CH_2$—, —$CH_2CH_2$—, —$CH_2CHOH$, —$CH_2CH_2CH_2$—, $CH_2CH_2CH_2CH_2$, $CH_2CHOHCH_2$ and —$CH_2CHOHCHOHCH_2$—, wherein Y is selected from $COO^-$ and $SO_3^-$, and wherein Z is selected from —$CH_2$—, —CHOH—, O and S;

(v) a compound of formula V:

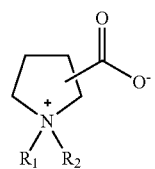
(V)

wherein $R_1$ and $R_2$ are each independently selected from aryl, arylalkyl, —H, —$CH_3$—$CH_2$—$CH_3$, —$CH_2CH_2OH$, $CH_2CHOHCH_3$, $CH_2CHOHCH_2OH$; and $CH_2CH_2CH_2OH$, (vi) a compound of formula VI:

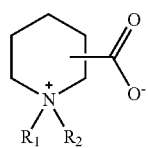
(VI)

wherein $R_1$ and $R_2$ are each independently selected from aryl, arylalkyl, —H, —$CH_3$—$CH_2$—$CH_3$, —$CH_2CH_2OH$, $CH_2CHOHCH_3$, $CH_2CHOHCH_2OH$, and $CH_2CH_2CH_2OH$;

(vii) a compound of formula VII:

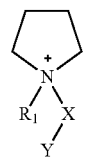
(VII)

wherein $R_1$ is selected from aryl, arylalkyl, —H, —$CH_3$—$CH_2$—$CH_3$, —$CH_2CH_2OH$, $CH_2CHOHCH_3$, $CH_2CHOHCH_2OH$, and $CH_2CH_2CH_2OH$, wherein X is selected from —$CH_2$—, —$CH_2CH_2$—, —$CH_2CHOH$, —$CH_2CH_2CH_2$—, —$CH_2CH_2CH_2CH_2$—, —$CH_2CHOHCH_2$—, and —$CH_2CHOHCHOHCH_2$—, wherein Y is selected from $CO_2^-$ and $SO_3^-$, and wherein Z is selected from $CH_2$, CHOH, O and S; and (viii) an osmoprotectant compound that is selected from trimethylammonium acetate, glycerol phosphate, diglycerol phosphate, N-(2-hydroxy-1,1-bis(hydroxymethyl)ethyl)glycine (tricine), 3-(N-morpholino)-2-hydroxypropanesulfonic acid (MOPSO), pentaerythritol, glyceric acid, malic acid, tartaric acid, lactic acid, glycolic acid, 2-hydroxybutyric acid, 3-hydroxybutyric acid, 4-amino-3-hydroxybutyric acid, 3-(1-azoniabicyclo[2.2.2]oct-1-yl)propane-1-sulfonate, and 1-(2-carboxylatoethyl)-1-azabicyclo[2.2.2]octan-1-ium, wherein the borate composition and the stabilizer are present at a molar ratio that is selected from a molar ratio of from about 10:1 to about 1:10, a molar ratio of from about 5:1 to about 1:5, and a molar ratio of from about 20:1 to about 1:20, and wherein the matrix is capable of preventing degradation of an isolated DNA fragment of at least 10 kilobases during substantially dry storage of the DNA fragment in the matrix at 85° C. for a time period of at least two weeks; and (b) substantially drying one or more of the sample wells, and thereby preparing the biological sample storage device. In a further embodiment the step of administering comprises administering a liquid solution or a liquid suspension that contains the matrix and a solvent. In another further embodiment at least one well comprises at least one detectable indicator, which in a still further embodiment comprises a dye or colorimetric indicator. In another further embodiment the detectable indicator is selected from phenol red, a food dye, ethidium bromide, a dye compatible with qPCR, a DNA polymerase, a restriction endonuclease, cobalt chloride, Reichardt's dye and a fluorogenic protease substrate.

In another embodiment of the present invention there is provided a method of recovering a stored biological sample, comprising (a) contacting, simultaneously or sequentially and in either order in a biological sample storage device, one or a plurality of biological samples with a matrix for substantially dry storage of a biological sample, wherein (1) said biological sample storage device comprises a sample plate comprising one or a plurality of sample wells that are capable of containing the biological sample, wherein one or more of said wells comprises the matrix, and wherein (2) the matrix comprises (a) a borate composition; and (b) at least one stabilizer that is selected from: (i) a compound of formula I:

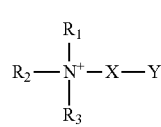

wherein $R_1$, $R_2$, $R_3$ are independently selected from aryl, arylalkyl, —H, —CH$_3$ and —CH$_2$—CH$_3$, wherein when $R_1$ and $R_2$ are CH$_3$ or CH$_2$—CH$_3$, $R_3$ is either H or absent, wherein X is selected from —CH$_2$—, —CH$_2$CH$_2$—, —CH$_2$CH$_2$CH$_2$—, —CH$_2$CH$_2$CH$_2$CH$_2$—,

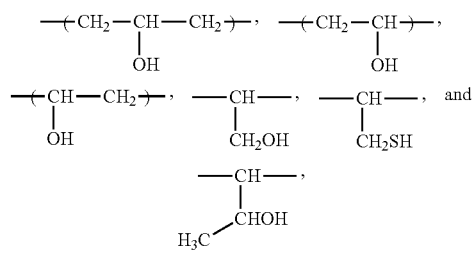

and wherein Y is selected from COO$^-$ and SO$_3^-$;

(ii) a compound of formula II:

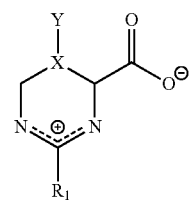

wherein $R_1$ is selected from CH$_3$ and CH$_2$CH$_3$, and wherein when X is CH, Y is selected from H and OH, and when X is CH$_2$—CH, Y is H;

(iii) a compound of formula III:

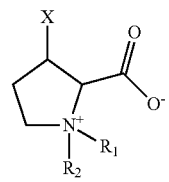

wherein $R_1$ and $R_2$ are independently selected from —H, —CH$_3$, and —CH$_2$CH$_3$, and wherein X is selected from H, OH and SH;

(iv) a compound of formula IV:

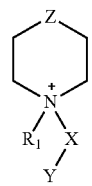

wherein $R_1$ is selected from aryl, arylalkyl, —H, —CH$_3$—CH$_2$—CH$_3$, —CH$_2$CH$_2$OH, CH$_2$CHOHCH$_3$, CH$_2$CHOHCH$_2$OH, and CH$_2$CH$_2$CH$_2$OH, wherein X is selected from —CH$_2$—, —CH$_2$CH$_2$—, —CH$_2$CHOH, —CH$_2$CH$_2$CH$_2$—, CH$_2$CH$_2$CH$_2$CH$_2$, CH$_2$CHOHCH$_2$ and —CH$_2$CHOHCHOHCH$_2$—, wherein Y is selected from COO$^-$ and SO$_3^-$, and wherein Z is selected from —CH$_2$—, —CHOH—, O and S;

(v) a compound of formula V:

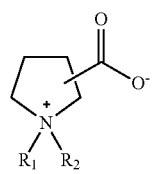

wherein $R_1$ and $R_2$ are each independently selected from aryl, arylalkyl, —H, —CH$_3$—CH$_2$—CH$_3$, —CH$_2$CH$_2$OH, CH$_2$CHOHCH$_3$, CH$_2$CHOHCH$_2$OH; and CH$_2$CH$_2$CH$_2$OH, (vi) a compound of formula VI:

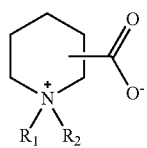

(VI)

wherein $R_1$ and $R_2$ are each independently selected from aryl, arylalkyl, —H, —$CH_3$—$CH_2$—$CH_3$, —$CH_2CH_2OH$, $CH_2CHOHCH_3$, $CH_2CHOHCH_2OH$, and $CH_2CH_2CH_2OH$;

(vii) a compound of formula VII:

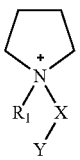

(VII)

wherein $R_1$ is selected from aryl, arylalkyl, —H, —$CH_3$—$CH_2$—$CH_3$, —$CH_2CH_2OH$, $CH_2CHOHCH_3$, $CH_2CHOHCH_2OH$, and $CH_2CH_2CH_2OH$, wherein X is selected from —$CH_2$—, —$CH_2CH_2$—, —$CH_2CHOH$, —$CH_2CH_2CH_2$—, —$CH_2CH_2CH_2CH_2$—, —$CH_2CHOHCH_2$—, and —$CH_2CHOHCHOHCH_2$—, wherein Y is selected from $CO_2^-$ and $SO_3^-$, and wherein Z is selected from $CH_2$, CHOH, O and S; and (viii) an osmoprotectant compound that is selected from trimethylammonium acetate, glycerol phosphate, diglycerol phosphate, N-(2-hydroxy-1,1-bis(hydroxymethyl)ethyl)glycine (tricine), 3-(N-morpholino)-2-hydroxypropanesulfonic acid (MOPSO), pentaerythritol, glyceric acid, malic acid, tartaric acid, lactic acid, glycolic acid, 2-hydroxybutyric acid, 3-hydroxybutyric acid, 4-amino-3-hydroxybutyric acid, 3-(1-azoniabicyclo[2.2.2]oct-1-yl)propane-1-sulfonate, and 1-(2-carboxylatoethyl)-1-azabicyclo[2.2.2]octan-1-ium, wherein the borate composition and the stabilizer are present at a molar ratio that is selected from a molar ratio of from about 10:1 to about 1:10, a molar ratio of from about 5:1 to about 1:5, and a molar ratio of from about 20:1 to about 1:20, and wherein the matrix is capable of preventing degradation of an isolated DNA fragment of at least 10 kilobases during substantially dry storage of the DNA fragment in the matrix at 85° C. for a time period of at least two weeks; (b) substantially drying one or more of the sample wells; (c) maintaining the biological sample storage device without refrigeration subsequent to the steps of contacting and drying; and (d) resuspending or redissolving the biological sample in a biocompatible solvent, and therefrom recovering the stored biological sample. In certain further embodiments the biological activity of the sample subsequent to the step of maintaining is substantially the same as biological activity of the sample prior to the step of contacting.

In another embodiment of the present invention there is provided a matrix for substantially dry storage of a biological sample, comprising (a) a borate composition which comprises at least one compound selected from the group consisting of boric acid, dihydrogen borate, hydrogen borate, diborate, triborate, tetraborate, metaborate, hydroxoborate (borax), borate salt, boric acid-glycerol, boric anhydride ($B_2O_3$) and boric-acid-1,3 propanediol; (b) at least one stabilizer selected from the group consisting of hydroxyectoine, ectoine, homoectoine, betaine, L-carnitine, sarcosine, N,N-dimethylglycine, triethylammonium acetate, glycerol phosphate, tricine, MOPSO, pentaerythritol and N-ethyl-N,N-bis-(2-hydroxyethyl)ammonium-N-4-butyl sulfonate, glycolic acid, lactic acid, malic acid and tartaric acid; and (c) a sample treatment composition, wherein the borate composition and the stabilizer are present at a molar ratio of from about 10:1 to about 1:10, and wherein the matrix is capable of preventing degradation of an isolated DNA fragment of at least 10 kilobases during substantially dry storage of the DNA fragment in the matrix at 85° C. for a time period of at least two weeks. In certain further embodiments the sample treatment composition comprises a composition that is selected from an activity buffer, a cell lysis buffer, a free radical trapping agent, a sample denaturant and a pathogen-neutralizing agent.

These and other aspects of the present invention will become apparent upon reference to the following detailed description and attached drawings. All references disclosed herein are hereby incorporated by reference in their entirety as if each was incorporated individually. Background information pertaining to storage and stabilization of biological samples, including compositions and methods for unrefrigerated dry storage, may be found, for example, in US 2005/0276728, WO 2005/113147, US 2006/0099567, WO 2007/075253, US 2008/0176209, US 2008/0268514, US 2008/0307117, US 2009/0291427, US 2009/0298132, WO 2009/009210, and WO 2009/038853.

DETAILED DESCRIPTION

Figure 1:
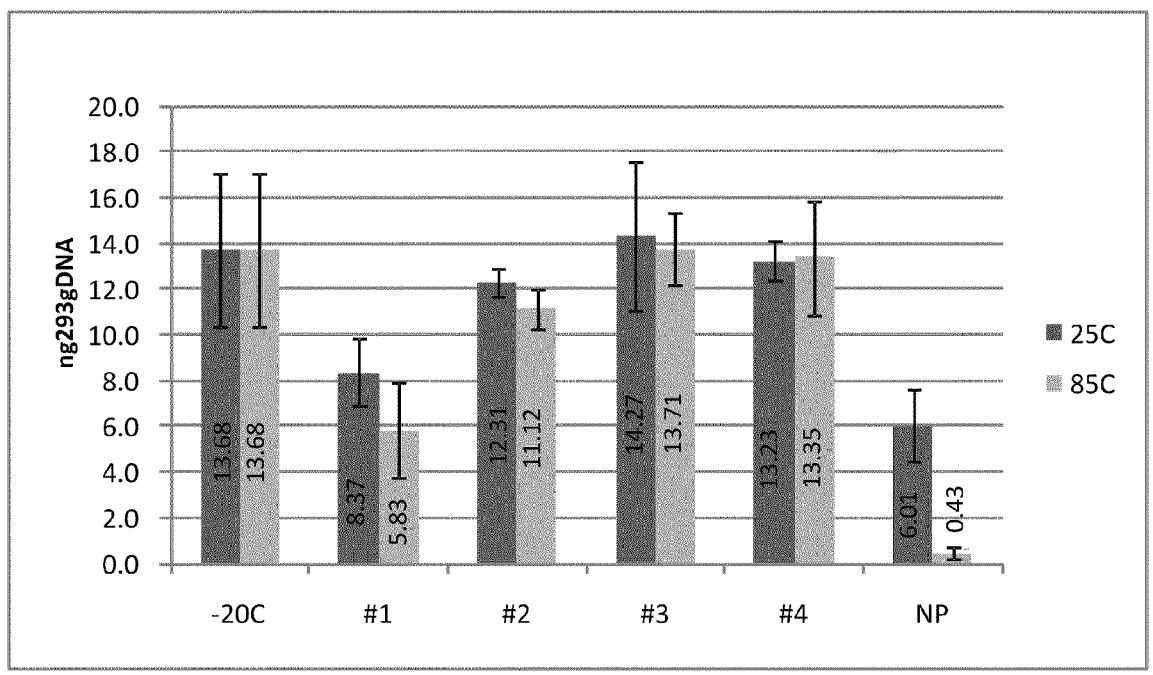
FIG. 1 summarizes DNA recoveries determined by quantitative PCR. Data were obtained using as PCR templates for each PCR reaction the DNA recovered following dry storage on the indicated dry storage matrix of 10 nanograms of DNA from HEK-293T cells at ambient temperature (25° C.) for 10 days, or for seven days at elevated temperature (85° C.). Set #1, dry storage matrix was prepared from 50 mM hydroxyectoine, mM boric acid, 0.4 mM DTPA, pH 8.3; Set #2, 50 mM hydroxyectoine, 10 mM boric acid, 1 mM sodium tetraborate, 0.4 mM DTPA, pH 8.3; Set #3, 25 mM hydroxyectoine, 10 mM boric acid, 0.4 mM DTPA, pH 8.3; Set #4, 25 mM hydroxyectoine, 10 mM boric acid, 1 mM sodium tetraborate, 0.4 mM DTPA, pH 8.3; NP, dry storage with no matrix material present; −20° C., data from control DNA samples analyzed after −20° C. storage for comparable time periods.

The present invention is directed in certain embodiments as described herein to compositions and methods for substantially dry storage of a biological sample, based on the surprising discovery that in the presence of certain matrix compositions that comprise a borate composition and a stabilizer as provided herein, a biological sample can be dried and stored at ambient or elevated temperatures for extended periods of time, such that upon subsequent restoration of solvent conditions substantially all of the biological activity of the sample can be recovered.

As described herein, certain invention embodiments relate in part to unexpected advantages provided by selection of a matrix that dissolves or dissociates in a biocompatible solvent (e.g., a solvent which is compatible with preserving structure and/or activity of a biological sample), and in part to unexpected advantages provided by the selection of the combination of a borate composition with a stabilizer such as a stabilizer of at least one of formulae (I)-(VII) or another stabilizer disclosed herein, from which combination certain particularly useful dry storage matrices may be comprised.

Certain embodiments described herein advantageously combine a borate composition, such as one or more of boric acid, dihydrogen borate, hydrogen borate, diborate, triborate, tetraborate, metaborate, hydroxoborate (borax), borate salt, boric acid-glycerol, boric anhydride ($B_2O_3$) and boric-acid-1,3 propanediol, with a stabilizer as provided herein such as a stabilizer of formula (I)-(VII), including in certain preferred embodiments a stabilizer that comprises a zwitterion (e.g., a typically water-soluble compound having charged and typically non-adjacent atoms but a net neutral, i.e., zero, charge) wherein the borate composition and the stabilizer are present at a molar ratio that is selected from a molar ratio of from about 10:1 to about 1:10, a molar ratio of from about 5:1 to about 1:5, and a molar ratio of from about 20:1 to about 1:20, including any intermediate molar ratios therein.

These and related embodiments permit efficient, convenient and economical storage of a wide variety of biological samples including polynucleotides (e.g., nucleic acids such as DNA, RNA, oligonucleotides and other naturally or artificially produced nucleic acids), enzymes and other proteins, and cells, without refrigeration or frozen storage. Samples may be dried without lyophilization (although lyophilization may be employed if desired), and following dry storage the samples may be used immediately upon solvent reconstitution without a need for separating the sample from the matrix material, which dissolves or dissociates in the solvent and does not interfere with biological activity of the sample.

Certain invention embodiments offer advantageously superior recoveries of stored biological samples, including enhanced detection sensitivity for interrogating samples containing minute quantities of biomolecules of interest, and may find uses in clinical, healthcare and diagnostic contexts, in biomedical research, biological research and forensic science, and in biological products and other settings where sample storage for life sciences may be desired. Of particular note, the compositions and methods described herein afford preservation and protection of biological samples under conditions typically regarded as inhospitable to biological sample storage, such as elevated temperatures (e.g., increased in a statistically significant manner over common ambient or room temperature ranges, such as sustained temperatures in excess of 25° C., 30° C., 35° C., 40° C., 45° C., 50° C., 55° C., 60° C., 65° C., 70° C. and significantly higher), without any need for expensive, cumbersome and energy-demanding refrigeration or freezing equipment. For example, these and related embodiments may be particularly attractive for collection, shipping, storage and retrieval of biological samples in undeveloped or underdeveloped regions of the world, as well as in highly developed areas.

Certain embodiments of the present invention thus relate to storage of dry samples including storage at ambient temperature, and also may have use for the storage of diverse biological materials and biological samples, such as but not limited to DNA, RNA, blood, urine, feces, other biological fluids (e.g., serum, serosal fluids, plasma, lymph, cerebrospinal fluid, saliva, mucosal secretions of the secretory tissues and organs, vaginal secretions, ascites fluids, fluids of the pleural, pericardial, peritoneal, abdominal and other body cavities, cell and organ culture medium including cell or organ conditioned medium, lavage fluids and the like, etc.), buccal cells from the inner lining of the cheek present in a buccal swab or sample, bacteria, viruses, yeast cells, PCR products, cloned DNA, genomic DNA, oligonucleotides, plasmid DNA, mRNA, tRNA, rRNA, siRNA, micro RNA, hnRNA, cDNA, proteins, polypeptides, lipids, glycoconjugates (e.g., glycolipids, glycoproteins), oligosaccharides, polysaccharides, vaccines (e.g., natural or synthetic, live or attenuated in the case of intact biological particles such as viral or other microbial vaccines, or extracts of natural, synthetic or artificial materials including products of genetic engineering), cells and tissues, cell or tissue lysates, cell or tissue homogenates or extracts, and the like, or other biological samples.

Biological samples may therefore also include a blood sample, biopsy specimen, tissue explant, organ culture, biological fluid or any other tissue or cell preparation, or fraction or derivative thereof or isolated therefrom, from a subject or a biological source. The subject or biological source may be a human or non-human animal, including mammals and non-mammals, vertebrates and invertebrates, and may also be any other multicellular organism or single-celled organism such as a eukaryotic (including plants and algae) or prokaryotic organism archaeon, microorganisms (e.g. bacteria, archaea, fungi, protists, viruses), aquatic plankton, a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, stem cells, germ cells (e.g. sperm, oocytes), transformed cell lines and the like.

According to certain embodiments described herein there are provided methods and compositions related to isolating nucleic acids from a biological sample such as, but not limited to, cells (e.g. eukaryotic, prokaryotic, bacteria, yeast) or viruses after dry storage in a dry storage matrix and subsequent rehydration of the sample. An unexpected advantage of the presently disclosed embodiments is the ability to isolate and extract nucleic acids from intact cells or viruses upon rehydration following dry storage without refrigeration in a storage matrix. The simple one-step addition of solvent, which in certain preferred embodiments may comprise water, to rehydrate samples stored dry in the matrix results, surprisingly, in isolation of nucleic acids that are ready for use in downstream applications; further purification of such extracted nucleic acids is unnecessary, but may be optionally performed.

As disclosed herein, the steps for sample preparation, dry storage and subsequent nucleic acid isolation by simple rehydration can all be performed under ambient conditions (e.g., at room temperature), thus eliminating the need for cold-storage and also eliminating the need for the use of any heating sources as part of the nucleic acid extraction procedure. A further advantage afforded by certain embodiments based on the present disclosure that will be appreciated by those skilled in the art is that the conditions optimized for the isolation of nucleic acids after dry storage in the matrix (e.g., the dry-storage matrix) render cells and viruses non-viable, thus significantly increasing biosafety levels, and further offering added convenience to many operations that may be involved in the handling of potentially pathogenic biological samples.

According to non-limiting theory, cells or viruses stored dry as described herein, in a dry-storage matrix for appropriate time periods at room temperature, are no longer viable due to breakdown of cell membranes and viral envelopes. Presumably (and further according to non-limiting theory) storage in the matrix renders the cell membranes or viral envelope remnants passive and completely penetrable to the matrix materials. Consequently, the nucleic acids contained within the cell or virus are protected from degradation by the storage matrix. Simple rehydration of the sample results in isolation and recovery of nucleic acid, thus eliminating the need for time-consuming and labor intensive purification methods, as well as reducing or eliminating dangers associated with handling suspected pathogens.

A further advantage that will be appreciated by one skilled in the art is the usefulness of the herein disclosed methods and compositions for replacing or augmenting costly freezer stocks of precious, and oftentimes numerous, biological samples. For example, bacterial cultures (from as little as a few microliters) can be applied directly into the storage matrix for long-term dry, room temperature storage and subsequent isolation of bacterial nucleic acids (e.g. plasmid or genomic DNA). The presently described compositions and methods thus provide an attractive and convenient alternative to maintaining glycerol stocks that are extremely labile to temperature fluctuations and that rely on costly and potentially vulnerable freezer equipment, particularly if numerous samples are involved. Hence, from as little as a few microliters of a typical suspension of cells or viruses, rapid and safe collection and processing of a large number of samples is possible. As disclosed herein, cell-based isolation of nucleic acids from samples stored dry in a dry-storage matrix as described below has the additional utility in that long-term cataloging, storage and processing of samples is possible via the simple addition of water (or another solvent such as a biocompatible solvent that comprises water) to isolate and recover nucleic acids. Sample processing (e.g., nucleic acid isolation) can be performed at the user's convenience, after collection of the biological sample, and can be delayed indefinitely.

As disclosed herein, the duration of the period for unrefrigerated dry storage of biological samples such as nucleic acids, proteins, cells or viruses on a dry-storage matrix, the particular biological source material such as the cells or viruses used (e.g., strains, substrains, variants, types, subtypes, isolates, quasi-species, and the like), and other factors may be varied to affect the nucleic acid storage, isolation and recovery methods. As will be appreciated by those skilled in the art and based on the present disclosure, preliminary studies may be done routinely to determine the optimal length of time for dry storage of, e.g., isolated nucleic acids or of intact cells or viruses in the matrix for protection and subsequent recovery of isolated nucleic acids. Conditions for substantially dry storage of a cell sample for purposes of recovering cellular nucleic acid from the sample are distinct from conditions that may permit recovery of viable cells (or of infective viral particles) following substantially dry storage on a matrix such as those described in US 2006/0099567, according to which viable cell recovery typically will involve storage periods of shorter duration than may be employed for recovering cellular nucleic acid. Thus, for example, in a preliminary study to determine a storage period beyond which few or no detectable viable cells may be recovered, the viability of a given preparation of bacterial cells, after rehydration following dry storage at room temperature in the storage matrix, can be determined by inoculating growth media directly with an aliquot of the rehydrated sample and growing or attempting to grow the culture under appropriate conditions (e.g. overnight at 37° C.).

Isolation and recovery of nucleic acids following dry storage of previously isolated nucleic acids, or of cells or viruses on a dry-storage matrix as described herein, can be determined using any of a number of assays practiced by those skilled in the relevant art, including those described herein (see for example, Maniatis, T. et al. 1982. *Molecular Cloning: A Laboratory Manual*, Cold Spring Harbor University Press, Cold Spring Harbor, N.Y.; Ausubel et al., 1993 *Current Protocols in Molecular Biology*, Greene Publ. Assoc. Inc. & John Wiley & Sons, Inc., Boston, Mass.). For example, to determine if plasmid DNA has been successfully isolated from bacterial cells after dry storage in the matrix at room temperature, rehydrated samples can be directly transformed into competent bacteria. Growth of bacterial colonies in the appropriate selection medium indicates successful incorporation of plasmid DNA, and colony counts provide an easy assay to determine transfection efficiency. Restriction enzyme analysis can also be performed to verify successful isolation of the appropriate plasmid DNA as recovered according to the presently described methods from bacterial cells that have been stored dry without refrigeration in the storage matrix.

Isolation and recovery of genomic DNA (or RNA) following dry storage without refrigeration on a dry-storage matrix as herein described can be determined using nucleic acid hybridization analysis (such as PCR, real-time PCR, reverse transcription PCR, quantitative PCR, etc.) with oligonucleotide primers that are specific for target genomic nucleic acid sequences that may be present in a dry-stored cell or virus. For example, PCR ribotyping can be used to identify bacterial strains (Kostman et al. 1995. *J. Infect. Dis.* 171:204-208). Other assays used for genomic phenotyping analysis include, for example, but are not intended to be limited to, restriction fragment length polymorphism analysis of PCR products, randomly amplified polymorphic DNA, repetitive element-based PCR, pulse-field gel electrophoresis, sequencing of individual genes that may be related to virulence, and multilocus enzyme electrophoresis, (see for example, Baumforth, K. R. N. et al. 1999. *J Clin Pathol: Mol. Pathol.* 52:112-10; Becker Y, Darai G. 1995. *PCR: protocols for diagnosis of human and animal virus diseases*, Springer Lab Manual. Berlin: Springer-Verlag; Read, S. J. 2000. *J. Clinical Path.* 53(7):502-506; Shaw, K. J. (ed). 2002. *Pathogen Genomics: Impact on Human Health*, Humana Press, Inc., Totowa, N.J.; Maiden, M. C. et al. 1998. *Proc. Natl. Acad. Sci. USA* 95:3140-3145; Lindstedt, B. A. et al. 2003. *J. Clin. Microbiol.* 41:1469-1479; Klevytska, A. M. et al. 2001. *J. Clin. Microbiol.* 39:3179-3185; and Yazdankhah, S. P. et al. 2005. *J. Clin. Microbiol.* 43(4):1699-1705).

As described herein, a nucleic acid refers to a polymer of two or more modified and/or unmodified deoxyribonucleotides or ribonucleotides, either in the form of a separate fragment or as a component of a larger construction. Examples of polynucleotides include, but are not limited to, DNA, RNA, or DNA analogs such as PNA (peptide nucleic acid), and any chemical modifications thereof. The DNA may be a single- or double-stranded DNA, cDNA, or a DNA amplified by any amplification technique, or any DNA polymer. The RNA may be mRNA, rRNA, tRNA, siRNA, total RNA, small nuclear RNA (snRNA), RNAi, micro RNA, genomic RNA, RNA isolated from cells or tissues, a ribozyme, or any RNA polymer. Encompassed are not only native nucleic acid molecules, such as those that can be isolated from natural sources, but also forms, fragments and derivatives derived therefrom, as well as recombinant forms and artificial molecules, as long as at least one property of the native molecules is present. Preferred biological samples are those that can be applied to analytical, diagnostic and/or pharmaceutical purposes, such as, but not limited to, nucleic acids and their derivatives (e.g. oligonucleotides, DNA, cDNA, PCR products, genomic DNA, plasmids, chromosomes, artificial chromosomes, gene transfer vectors, RNA, mRNA, tRNA, siRNA, miRNA, hnRNA, ribozymes, genomic RNA, peptide nucleic acid (PNA), and bacterial artificial chromosomes (BACs)).

Nucleic acid molecule(s), oligonucleotide(s), and polynucleotide(s), include RNA or DNA (either single or double stranded, coding, complementary or antisense), or RNA/DNA hybrid sequences of more than one nucleotide in either single chain or duplex form (although each of the above species may be particularly specified). The term "nucleotide" may be used herein as an adjective to describe molecules comprising RNA, DNA, or RNA/DNA hybrid sequences of any length in single-stranded or duplex form. More precisely, the expression "nucleotide sequence" encompasses the nucleic material itself and is thus not restricted to the sequence information (i.e., the succession of letters chosen among the four base letters) that biochemically characterizes a specific DNA or RNA molecule. The term "nucleotide" is also used herein as a noun to refer to individual nucleotides or varieties of nucleotides, meaning, e.g., a molecule, or individual subunit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" which comprise at least one modification such as (a) an alternative linking group, (b) an analogous form of purine, (c) an analogous form of pyrimidine, or (d) an analogous sugar.

Certain embodiments of the present invention relate to the preservation, storage, retrieval, and/or analysis of nucleic acids isolated from intact cells or viruses. An intact cell preferably has an intact plasma membrane that is capable of selectively excluding solutes and/or of retaining cellular cytoplasmic components such as organelles (e.g., nuclei, ribosomes, mitochondria, endoplasmic reticulum, vacuoles) vesicles and other membrane-bound compartments, intracellular biomolecules (polynucleotides, polypeptides, lipids, carbohydrates, intracellular mediators, co-factors and the like), macromolecular structures and/or assemblies (e.g., cytoskeletal elements, centrioles, chromatin), cytosol, etc. Preferably and in certain non-limiting embodiments, an intact cell is viable, but the invention need not be so limited. Certain embodiments are provided for the isolation and/or extraction from cells and/or viruses, and storage of cellular nucleic acids at ambient temperature, that are obtained or derived from biological samples that may include but are not limited to blood and cells contained therein (e.g., lymphocytes, polymorphonuclear leukocytes, monocytes, granulocytes, platelets, erythrocytes and other circulating cells including cells of hematopoietic origin), urine, other biological fluids (e.g., serum, serosal fluids, plasma, lymph, cerebrospinal fluid, saliva, mucosal secretions of the secretory tissues and organs, vaginal secretions, ascites fluids, fluids of the pleural, pericardial, peritoneal, abdominal and other body cavities, cell and organ culture medium including cell or organ conditioned medium, lavage fluids and the like, etc.), cells from the inner lining of the cheek present in a buccal swab or sample, bacteria, biofilms, viruses, yeast cells, cells and tissues, cell or tissue lysates, cell or tissue homogenates or extracts, and the like, or other biological samples.

Other sources of intact cells for isolation or extraction of nucleic acids that are contemplated herein may also include a blood sample, biopsy specimen (including tumor specimens), tissue explant, organ culture, cancer cell, biological fluid or any other tissue or cell preparation, or fraction or derivative thereof or isolated therefrom, from a subject or a biological source. The subject or biological source may be a human or non-human animal, including mammals and non-mammals, vertebrates and invertebrates, and may also be any other multicellular organism or single-celled organism or biofilm such as a eukaryotic (including plants) or prokaryotic organism or archaea, a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines and the like.

Bacterial cells according to certain embodiments described herein may include bacteria that belong to a genus selected from *Caulobacter, Staphylococcus, Bacillus, Salmonella, Campylobacter, Aerobacter, Rhizobium, Agrobacterium, Clostridium, Nostoc, Tricodesium, Pseudomonas, Xanthomonas, Nitrobacteriaceae, Nitrobacter, Nitrosomonas, Thiobacillus, Spririllum, Vibrio, Baceroides, Kelbsilla, Escherichia, Klebsiella, Shigella, Erwinia, Rickettsia, Chlamydia, Mycobacterium, Polyangium, Micrococcus, Lactobacillus, Diplococcus, Streptococcus, Spirochaeta, Treponema, Borrelia, Leptospira,* or *Streptomyces*.

Certain embodiments relate to a biological sample that may comprise an isolated biomolecule, where the term "isolated" means that the material is removed from its original environment (e.g., the natural environment if it is naturally occurring). For example, a naturally occurring nucleic acid or polypeptide present in an intact cell or in a living animal is not isolated, but the same nucleic acid or polypeptide, separated from some or all of the co-existing materials in the natural system, is isolated. Such nucleic acids could be part of a vector and/or such nucleic acids or polypeptides could be part of a composition, and still be isolated in that such vector or composition is not part of its natural environment.

Certain other embodiments relate to a biological sample that may comprise an intact cell or a living animal or organism that has not been depleted of, or from which has not been removed, a cell-derived molecular component such as a protein or peptide, lipid (including phospholipids, glycolipids and other lipids), nucleic acid (including DNA and RNA), carbohydrate (including oligosaccharides and polysaccharides and their derivatives), metabolite, intermediate, cofactor or the like, or any covalently or non-covalently complexed combination of these components and any other biological molecule that is a stable or transient constituent of a viable cell.

Techniques for isolating and/or purifying a cellular molecular component may include any biological and/or biochemical methods useful for separating the component from its biological source, and subsequent characterization may be performed according to standard biochemical and molecular biology procedures. Those familiar with the art will be able to select an appropriate method depending on the biological starting material and other factors. Such methods may include, but need not be limited to, radiolabeling or otherwise detectably labeling cellular and subcellular components in a biological sample, cell fractionation, density sedimentation, differential extraction, salt precipitation, ultrafiltration, gel filtration, ion-exchange chromatography, partition chromatography, hydrophobic chromatography, electrophoresis, affinity techniques or any other suitable separation method that can be adapted for use with the agent with which the cellular molecular component interacts. Antibodies to partially purified components may be developed according to methods known in the art and may be used to detect and/or to isolate such components.

Certain other embodiments relate to a biological sample that may comprise a purified biomolecule, such as but not limited to a nucleic acid, where the terms "purified" or "substantially purified" refer to recovery of a biomolecule (such as a nucleic acid) which is at least 50-55%, 55-60%, 60-65%, 65-70%, 70-75%, 75-80%, 80-85%, 85-90%, 90-95%, 92%, 94%, 96%, 98%, 95-100% or 98-100% purified with respect to removal of a contaminant, e.g., cellular components such as protein, lipid or salt; thus, the term "substantially purified" generally refers to separation of a majority of cellular proteins or reaction contaminants from the biological sample, so that compounds capable of interfering with the subsequent use of the isolated biomolecule (such as a nucleic acid) are removed.

Certain herein described embodiments relate to stabilization and/or preservation of a biological sample, which involves maintenance, retention or reconstitution of the structural and/or functional integrity of biological samples (including of molecular, multimolecular or oligomeric, organellar, subcellular, cellular, multicellular, or higher organizational levels of biological structure and/or function) and of the biological properties based thereupon. The biological activity of a biological sample that comprises, in a particular embodiment, a macromolecule or biopolymer or the like such as a polypeptide or polynucleotide, may involve, for example, the extensive maintenance of its primary, secondary and/or tertiary structure. The biological activity of a nucleic acid probe comprises, for example, its property of forming in a sequence-specific manner a hybridization complex (e.g., a duplex) with a nucleic acid target which is complementary to the probe. The biological activity of a nucleic acid, for example, may comprise a DNA encoding a cytocide, a prodrug, a therapeutic molecule, or another nucleic acid molecule or encoded product that has a discernible or detectable effect upon or within cells. Such biological activity may be assayed by any method known to those of skill in the art, including, but not limited to, in vitro and/or in vivo assays that assess efficacy by measuring the effect on cell proliferation or on protein synthesis (see for example, Sambrook et al., 1989; Current Protocols, Nucleic Acid Chemistry, Molecular Biology, Wiley and Sons, 2003; and Asubel, F M et al. (Eds.). 2007. *Current Protocols in Molecular Biology*, Wiley and Sons, Inc. Hoboken, N.J.). Additional non-limiting examples of the biological activity of nucleic acids and polynucleotides include transfection, transformation, amplification, enzymatic reaction, gene expression, translation, transcription, and hybridization. The biological activity of an antibody comprises, for example, a specific binding interaction with its cognate antigen.

As described herein, the biological activity of a substance means any activity which can affect any physical or biochemical properties of a biological system, pathway, molecule, or interaction relating to an organism, including for example but not limited to, viruses, bacteria, bacteriophage, prions, insects, fungi, plants, animals, and humans. Examples of substances with biological activity include, but are not limited to, polynucleotides, peptides, proteins, enzymes, antibodies, small molecules (e.g. a bioactive small molecule, whether naturally occurring or artificial, preferably of less than $10^5$ daltons molecular mass, more preferably less than $10^4$ daltons, and more preferably less than $10^3$ daltons, as provided herein), pharmaceutical compositions (e.g., drugs), vaccines, carbohydrates, lipids, steroids, hormones, chemokines, growth factors, cytokines, liposomes, and toxins, liposomes. Persons familiar with the relevant art will recognize appropriate assays and methods for determining the biological activity of substances that affect the physical or biochemical properties of a biological system, including for example but not limited to, gene expression (see for example, Asubel, F M et al. (Eds.). 2007. *Current Protocols in Molecular Biology*, Wiley and Sons, Inc. Hoboken, N.J.), receptor-ligand interactions (see for example, Coligan et al. (Eds.).

2007. *Current Protocols in Immunology*, Wiley and Sons, Inc. Hoboken, N.J.), enzymatic activity (see for example, Eisenthal and Hanson (Eds.), 2002 *Enzyme Assays*. Second Edition. Practical Approaches series, no 257. Oxford University Press, Oxford, UK; Kaplan and Colowick (Eds.), 1955 and 1961 *Preparation and Assay of Enzymes, Methods in Enzymology*, (vols. 1, 2 and 6). Academic Press, Ltd., Oxford, UK), cytokine and cell proliferation and/or differentiation activities (see for example, Coligan et al. (Eds.). 2007. *Current Protocols in Immunology*, Wiley and Sons, Inc. Hoboken, N.J.), signal transduction (see for example, Bonifacino et al. (Eds.). 2007. *Current Protocols in Cell Biology*, Wiley and Sons, Inc. Hoboken, N.J.) and cell toxicity (see for example, Bus J S et al. (Eds). 2007. *Current Protocols in Toxicology*, Wiley and Sons, Inc. Hoboken, N.J.), apoptosis and necrosis (Green, D R and Reed, J C. 1998 *Science* August 28; 281 (5381):1309-12; Green, D R. 1998. *Nature* December 17: 629; Green D R. 1998 *Cell* 94(6):695-69; Reed, J C (Ed.), 2000 *Apoptosis, Methods in Enzymology* (vol. 322). Academic Press Ltd., Oxford, UK).

As described herein, recovery, following storage, of substantially all biological activity refers to recovery of at least 70-75%, 75-80%, 80-85%, 85-90%, 90-95%, 92%, 94%, 96%, 98%, 99%, 95-100% or 98-100% of the biological activity of a sample as compared to the biological activity of the sample as determined prior to storage according to the methods and compositions as provided herein. In other embodiments as described herein, substantial loss of the biological activity of a sample may be apparent when, for instance, following unrefrigerated substantially dry storage of an isolated nucleic acid sample or of a dry-storable cell sample, the biological activity after storage decreases in a statistically significant manner compared to the biological activity present in the sample prior to storage, which decrease may in some embodiments refer to any decrease in activity having statistical significance relative to an appropriate control sample as will be familiar to those skilled in the art, but which may in some other embodiments refer to a decrease having statistical significance that is more than a decrease of 1%, 2%, 3%, 4%, 5%, 6%, 7%, 8%, 9%, 10%, 10-12%, 12-15%, 15-20%, 20-25% or 25-30% of the biological activity present in the sample prior to storage.

For example, and remarkably, according to certain herein disclosed embodiments, dry storage of isolated intact cells comprising, as provided herein, contacting one or a plurality of isolated intact cells that contain nucleic acid with the presently disclosed dry-storage matrix that dissolves in a biocompatible solvent, drying the matrix to substantially remove the solvent, maintaining without refrigeration for one or more days the dry-storable cell sample so obtained, and resuspending or redissolving the sample in a biocompatible solvent, permits simple and efficient recovery of substantially purified cellular nucleic acid having substantially all of the biological activity present in the cellular nucleic acid prior to dry storage. Preferably in such embodiments the cell is a bacterial cell. For example, and according to non-limiting theory, substantially dry storage of a bacterial cell sample on a dry-storage matrix followed by solvent reconstitution (e.g., rehydration) under conditions and for a time sufficient as described herein, is believed to release gently and efficiently the cellular nucleic acid from the bacterial cell, such that the simple resuspension or resolubilization of the dried cell sample in a biocompatible solvent permits ready recovery of isolated cellular nucleic acid. In other related embodiments wherein the cell is a non-bacterial cell, the step of recovering isolated nucleic acid from a dry-stored cell sample preferably includes purifying the nucleic acid according to any of a number of methodologies for nucleic acid extraction, separation, differential solubilization, isolation, etc. such as those described herein and known to the art.

In certain embodiments, the invention thus relates to the long-term storage of biological, chemical and biochemical material under dry conditions, and in a manner ready for immediate use after hydration (e.g., upon rehydration). As described herein, there are provided embodiments which include a) the specific dissolvable (or dissociatable) storage matrix comprising a borate composition and a stabilizer (which in certain embodiments may be a zwitterionic compound) as provided herein, and optionally comprising additional components as described herein, such as one or more of a chelator, a pH buffer, a biological or biochemical inhibitor and/or a detectable indicator, b) preparation and optimization of the storage matrix with chemicals that increase the durability of the longterm storage conditions, including in certain embodiments, e.g., the use of a stabilizer which may comprise a compound of formula (I)-(VII) and/or another osmoprotectant compound, c) preparation of different biological materials prior to the drying process that allow immediate activity and usability of the materials after rehydration, and d) the process of simplifying complex biochemical processes through the use of dry stored biologically active materials.

These and related embodiments thus provide surprising advantages associated with unrefrigerated dry storage of biologicals, including improved stabilization and preservation of biological activity in biological samples, reduced degradation of biological samples during storage at room temperature in dried form (and in particular through the use of a protective matrix), and simplification of the processes for preparing biological samples for further use by reducing or eliminating the need for time-consuming re-calibration and aliquoting of such samples, and by eliminating the need for physically separating a sample from the storage medium. Invention embodiments as described herein additionally provide unexpectedly superior biological sample recoveries by reducing or eliminating factors that can otherwise reduce sample recovery yields, such as undesirable sample denaturation and/or sample loss due to adsorption of the sample on sample container surfaces.

According to certain embodiments the invention allows for purification and optionally size fractionation of DNA, RNA, proteins and other biomolecules, cells, cellular components and other biological materials, minerals, chemicals, or compositions derived from a biological sample or other life sciences related sample. In certain embodiments the invention thus readily permits, for example, the use of one or a plurality of biological materials and/or biological samples in the performance of molecular biology procedures, including but not limited to polymerase chain reaction or PCR (including RT-PCR), biopolymer (e.g., polynucleotide, polypeptide, oligosaccharide or other biopolymer) sequencing, oligonucleotide primer extension, haplotyping (e.g., DNA haplotyping) and restriction mapping in one unified, integrated and easy-to-use platform. The invention also readily permits, for example and in certain embodiments, the use of one or a plurality of biological samples and/or biological materials for the performance of protein crystallography. In other embodiments there is provided a platform for use, testing or detection (including diagnostic applications) of an antibody or small molecule (whether naturally occurring or artificial) or other biological molecule (e.g., a "biomolecule"), for example, a protein, polypeptide, peptide, amino acid, or derivative thereof; a lipid, fatty acid or the like, or derivative thereof; a carbohydrate, saccharide or the like or derivative thereof, a nucleic acid, nucleotide, nucleoside, purine, pyrimidine or related molecule, or derivative thereof, or the like; or another biological molecule that is a constituent of a biological sample.

Dry Storage of a Biological Sample

Compositions and methods described herein relate to dry and/or substantially dry storage of a biological sample, and may include the use of any suitable container, including, for example, a dry storage device. The dry storage device is an application of the biological sample storage device as herein disclosed, which contains a matrix material for use as a dry storage matrix, including in certain preferred embodiments a matrix material that dissolves or dissociates in a solvent comprising borate and at least one stabilizer that comprises a compound of formula (I)-(VII) and/or an osmoprotectant compound as disclosed herein, preferably selected according to certain embodiments from the group consisting of hydroxyectoine, ectoine, homoectoine, betaine, L-carnitine, sarcosine, N,N-Dimethylglycine, triethylammonium acetate, glycerol phosphate, tricine, MOPSO, pentaerythritol and N-ethyl-N,N-bis-(2-hydroxyethyl)ammonium-N-4-butyl sulfonate as described herein, for long-term storage of a biological sample or a biological material, such as but not limited to blood, bacteria, cells, viruses, chemical compounds (whether naturally occurring or artificially produced), plasmid DNA, DNA fragments, oligonucleotides, peptides, fluorogenic substrates, genomic DNA, PCR products, cloned DNA, proteins, RNA, vaccines, minerals and chemicals, and other biological samples as disclosed herein.

These and related embodiments derive from the surprising observation that stable, long-term dry storage of biological samples or biological materials may be effected without refrigeration when such samples or materials are loaded onto a suitable matrix material such as those described herein, including a dissolvable (or dissociable) matrix material that comprises a borate composition and a stabilizer. According to non-limiting theory, biological materials present in a biological sample may interact with the matrix material by absorption, adsorption, specific or non-specific binding or other mechanism of attachment, including those involving formation of non-covalent and/or covalent chemical bonds and or intermolecular associative interactions such as hydrophobic and/or hydrophilic interactions, hydrogen bond formation, electrostatic interactions, and the like. Accordingly, the present invention provides devices for stable, long-term dry storage of biological samples at common indoor ambient room temperatures (e.g., typically 20-27° C. but varying as a function of geography, season and physical plant from about 15-19° C. or about 18-23° C. to about 22-29° C. or about 28-32° C.) for use in the sample storage and processing methods and systems described herein.

Preferred embodiments employ the dissolvable matrix material (e.g., borate composition/stabilizer matrix) or a dissociable matrix material that may be dried before, during, or after being contacted with the sample to provide dry storage, wherein in some preferred embodiments such contact involves contacting the matrix material and the sample in a fluid or liquid (e.g., fluidly contacting), to provide substantially dry storage. Related preferred embodiments thus involve the use of sample storage devices as described herein that comprise a matrix material which is capable of dry storage of a biological sample or a biological material without refrigeration, for example, at ambient room temperature. In certain related embodiments a drying step may be performed to effect loading of the sample onto the matrix material for dry storage, for example by air drying, drying at elevated temperature or by the volatilization of solvent through exposure of the sample loaded matrix material to reduced atmospheric pressure (e.g., lyophilization or other vacuum drying method) or to a gentle flowstream of a compatible gas such as nitrogen. The samples are preferably stored dry under conditions that stabilize the sample, i.e., little or no detectable (e.g., with statistical significance) degradation or undesirable chemical or physical modification of the sample occurs, according to criteria that will vary as a factor of the nature of the sample being stored and that will in any event be familiar to those having skill in the relevant art. In other embodiments using the dry storage device, sample loading results in dry storage, for example, whereby a liquid sample is absorbed by, adsorbed to or otherwise entrapped by the matrix material such that after loading no free liquid is readily discernible in or on, or easily dislodged from, the matrix material, which may be dried as just described.

Certain preferred embodiments provide compositions and methods for storing biological material (e.g., polynucleotides, genomic DNA, plasmid DNA, DNA fragments, RNA, oligonucleotides, proteins, peptides, fluorogenic substances, cells, viruses, chemical compounds, vaccines, etc.) or other biological samples as provided herein on a matrix comprised of a material that dissolves or dissociates, the matrix comprising a borate composition and at least one stabilizer comprising a compound of formula (I)-(VII) and/or an osmoprotectant compound as provided herein, in a solvent that allows complete recovery or substantial recovery (e.g., recovery of at least 50 percent, preferably at least 60 percent, more preferably at least 70 percent, more preferably at least 80 percent, and typically in more preferred embodiments at least 85 percent, more preferably at least 90, 91, 92, 93 or 94 percent, more preferably at least 95 percent, still more preferably greater than 96, 97, 98 or 99 percent) of the dried sample material after hydration, rehydration or other solvent reconstitution of the sample.

For example, a dissolvable matrix comprising a borate composition and at least one stabilizer of formula (I)-(VII) and/or an osmoprotectant may be capable of being solubilized in a suitable solvent that can be selected based on the properties of the matrix material and/or of the sample depending on the particular methodology being employed and in a manner that permits recovery of one or more desired structural or functional properties of the sample (e.g., biological activity). Similarly, as another example, the matrix comprising a borate composition and at least one stabilizer of formula (I)-(VII) and/or an osmoprotectant may dissociate in a solvent and may, but need not, become fully solubilized, such that a dispersion, suspension, colloid, gel, sap, slurry, syrup, or the like may be obtained. In other embodiments a matrix comprising borate composition and at least one stabilizer of formula (I)-(VII) and/or an osmoprotectant may further include, in addition to the dissolvable/dissociable borate/stabilizer matrix components, one or more additional components such as, but not limited to, a sponge-like material, silica, silica powder, silica filter paper, absorbent powder, cotton, wool, linen, polyvinyl alcohol (PVA), polyvinylpyrrolidone (PVP), polyacrylamide, poly(N-vinylacetamide), polyester, nylon, positively charged nylon or filter paper, any of which may influence physicochemical properties, including solubility properties, of the storage matrix, as will be appreciated by those familiar with the art.

In certain of these and related embodiments, the first solvent which is used to introduce the matrix material and/or the biological sample to the biological sample storage device prior to a drying step for dry sample storage may be the same as the second solvent that is subsequently used to hydrate, rehydrate, reconstitute or resuspend the dried sample/matrix combination, and in other embodiments the second solvent may be different from the first. Criteria for selection of a suitable solvent for dissolving or dissociating the matrix material and/or the biological sample will be known to those familiar with the relevant art based, for example, on physicochemical properties of the particular matrix material and sample being used, and on the structural or functional properties (e.g., bioactivity) that are desirably retained during dry storage and subsequent reconstitution, as well as on other factors (e.g., compatibility with other storage device materials, or liquid handling equipment, safety, etc.).

In certain preferred embodiments at least one solvent for use in compositions and methods disclosed herein will be aqueous, for example, a biocompatible solvent such as a biological fluid, a physiological solution or an aqueous biological buffer solution selected to support a biological structure and/or function of a biomolecule by preserving for that biomolecule a favorable chemical milieu that is conducive to the structure and/or function. Non-limiting examples of such biocompatible solvents include physiological saline (e.g., approximately 145 mM NaCl), Ringer's solution, Hanks' balanced salt solution, Dulbecco's phosphate buffered saline, Erle's balanced salt solution, and other buffers and solutions and the like as will be known to those familiar with the art, including those containing additives as may be desired for particular biomolecules of interest.

According to other embodiments, however, the invention need not be so limited and other solvents may be selected, for instance, based on the solvent polarity/polarizability (SPP) scale value using the system of Catalan et al. (e.g., 1995 Liebigs Ann. 241; see also Catalan, 2001 In: Handbook of Solvents, Wypych (Ed.), Andrew Publ., NY, and references cited therein), according to which, for example, water has a SPP value of 0.962, toluene a SPP value of 0.655, and 2-propanol a SPP value of 0.848. Methods for determining the SPP value of a solvent based on ultraviolet measurements of the 2-N,N-dimethyl-7-nitrofluorene/2-fluoro-7-nitrofluorene probe/homomorph pair have been described (Catalan et al., 1995). Solvents with desired SPP values (whether as pure single-component solvents or as solvent mixtures of two, three, four or more solvents; for solvent miscibility see, e.g., Godfrey 1972 Chem. Technol. 2:359) based on the solubility properties of a particular matrix material can be readily identified by those having familiarity with the art in view of the instant disclosure.

Borate Compositions in the Dissolvable/Dissociatable Dry Storage Matrix

According to non-limiting theory, the dissolvable or dissociable matrix material may therefore comprise a borate composition and at least one stabilizer as provided herein (e.g., a compound of formula (I)-(VII) and/or an osmoprotectant compound, which may include a compound in one of formulae (I)-(VII)) which, by forming a matrix, creates a three dimensional space which allows biological material of the biological sample to associate with the matrix. The dissolvable or dissociable matrix material may be used to introduce additional stabilizing agents such as salts and buffers (e.g., pH buffers) under dehydrated (e.g., dried or substantially solvent-free) conditions. By way of example but without limitation, exemplary stabilizers include zwitterionic compounds in certain preferred embodiments and may also include non-zwitterionic compounds, and may in certain other preferred embodiments be selected from hydroxyectoine, ectoine, homoectoine, betaine, L-carnitine, sarcosine, N,N-Dimethylglycine, triethylammonium acetate, glycerol phosphate, tricine, MOPSO, pentaerythritol and N-ethyl-N,N-bis-(2-hydroxyethyl)ammonium-N-4-butyl sulfonate and the like. The matrix also allows inclusion of components (e.g., buffers) for the adjustment of pH and other parameters for optimal drying and storage conditions, and may optionally comprise one or a plurality of detectable indicators as provided herein, such as color-based pH indicators, and/or moisture indicators. According to certain other embodiments, the dissolvable or dissociable matrix material may be any suitable material having the compatible characteristics for storing a particular type of biological sample in a manner that satisfactorily preserves the desired structural and/or functional properties, said characteristics including the ability to dry in a manner that forms a matrix within the interstices of which the biological molecules of interest are deposited, and also including appropriate solvent (e.g., biological buffer) compatibility further including an ability to be redissolved or resuspended subsequent to dry storage in a manner whereby the matrix molecules do not interfere with one or more biological activities of interest in the sample.

Non-limiting examples of a borate compositions for use according to certain presently contemplated embodiments include sodium tetraborate (borax), boric acid, combinations of borate with citrate, boric acid-glycerol, boric acid-1,3 propanediol and the like, including dihydrogen borate, hydrogen borate, diborate, triborate, tetraborate, metaborate, hydroxoborate (borax), borate salt, boric acid-glycerol, boric anhydride ($B_2O_3$) and boric-acid-1,3 propanediol. As used herein, boric acid salt and borate salt are used interchangeably to refer to a salt such as potassium borate, monoethanolamine borate, or another salt obtained by, or that can be visualized as being obtained by, neutralization of boric acid. The weight percent of a boric acid salt or borate salt in a composition of these and related embodiments can be expressed either as the weight percent of either the negatively charged boron containing ion, e.g. the borate and/or boric acid moieties, or as the weight percent of the entire boric acid salt, e.g. both the negatively charged moiety and the positively charged moiety. Preferably, the weight percent refers to the entire boric acid salt. Weight percents of citric acid salts, or other acid salts, can also be expressed in this manner, preferably with reference to the entire acid salt. As used herein, the term "total boron compound" refers to the sum of borate and boric acid moieties. The borate salt may also include any of a variety of salts of boric acid, for example, alkali metal salts or alkanol amine salts. Examples of the use of borate as a stabilizing agent for biological molecules include those found, for example, in US Patent Publications 2006/0293212, 2006/0193968, 2007/0073039, and 2006/0177855, and in WO 2009/002568. Certain borate compositions as disclosed herein may also possess functional attributes of pH buffers and/or of biological or biochemical inhibitors as described herein. For example, borate is known to inhibit nuclease digestion reactions. (Maniatis, T. et al. 1982. Molecular Cloning: A Laboratory Manual, Cold Spring Harbor University Press, Cold Spring Harbor, N.Y.)

Certain embodiments of the present invention are contemplated that include the use of such combinations of a dissolvable or dissociatable matrix material comprising a borate composition and at least one such stabilizer of formula (I)_(VII) (or an osmoprotectant compound as provided herein), along with a second stabilizer that may or may not comprise a biological or biochemical inhibitor. Certain other embodiments of the present invention contemplate the use of such combinations of a dissolvable or dissociatable matrix material comprising borate and at least one stabilizer for substantially dry storage of biological samples such as proteins, cells, viruses, bacteria, blood, tissues and polynucleotides such as DNA, RNA, synthetic oligonucleotides, genomic DNA, natural and recombinant nucleic acid plasmids and constructs, and the like.

As described herein, according to certain embodiments, the borate composition of the herein described dry storage matrix is capable of non-covalent association with one or more stabilizers that is a compound of formula (I)-(VII) or an osmoprotectant compound, and that may be preferably hydroxyectoine, ectoine, homoectoine, betaine, L-carnitine, sarcosine, N,N-dimethylglycine, triethylammonium acetate, glycerol phosphate, tricine, MOPSO, pentaerythritol and/or N-ethyl-N,N-bis-(2-hydroxyethyl)ammonium-N-4-butyl sulfonate, and according to certain other non-limiting embodiments, the stabilizer is capable of non-covalent association with one or more molecular species present in the liquid-storable biological sample and having origins in the subject or biological source (e.g., biomolecules such as polypeptides, polynucleotides, naturally occurring oligosaccharides, naturally occurring lipids, and the like).

Methodologies and instrumentation for the determination of non-covalent associations between such components will be known to those familiar with the art in view of the present disclosure, and may include techniques such as electrospray ionization mass spectrometry (Loo et al., 1989 *Anal. Biochem. June;* 179(2):404-412; Di Tullio et al. 2005 *J. Mass Spectrom.* July; 40(7):845-865), diffusion NMR spectroscopy (Cohen et al., 2005 *Angew Chem Int Ed Engl.* January 14; 44(4):520-554), or other approaches by which non-covalent associations between molecular species of interest can be demonstrated readily and without undue experimentation (for example, circular dichroism spectroscopy, scanning probe microscopy, spectrophotometry and spectrofluorometry, and nuclear magnetic resonance of biological macromolecules; see e.g., Schalley C A et al. (Eds.) 2007 *Analytical Methods in Supramolecular Chemistry* Wiley Publishers, Hoboken, N.J.; Sauvage and Hosseini (Eds.). 1996. *Comprehensiva Fe Supramolecular Chemistry.* Elsevier Science, Inc. New York, London, Tokyo; Cragg, P J (Ed.). 2005 *A Practical Guide to Supramolecular Chemistry* Wiley & Sons, Ltd., West Sussex, UK; James et al. (Eds.), 2001 and 2005 *Nuclear Magnetic Resonance of Macromolecules: Methods in Enzymology* (vols. 338, 399 and 394) Academic Press, Ltd., London, UK).

Stabilizer

According to certain preferred embodiments described herein there are provided compositions and methods that include a dry storage matrix comprising a borate composition and at least one stabilizer as provided herein. Exemplary and preferred stabilizers may include a stabilizer compound according to any one or more of structural formulae (I)-(VII), and/or an osmoprotectant compound such as trimethylammonium acetate, glycerol phosphate, diglycerol phosphate, N-(2-hydroxy-1,1-bis(hydroxymethyl)ethyl)glycine (tricine), 3-(N-morpholino)-2-hydroxypropanesulfonic acid (MOPSO), pentaerythritol, glyceric acid, malic acid, tartaric acid, lactic acid, glycolic acid, 2-hydroxybutyric acid, 3-hydroxybutyric acid, 4-amino-3-hydroxybutyric acid, 3-(1-azoniabicyclo[2.2.2]oct-1-yl)propane-1-sulfonate, and/or 1-(2-carboxylatoethyl)-1-azabicyclo[2.2.2]octan-1-ium. Certain presently preferred embodiments contemplate inclusion in the matrix of at least one stabilizer such as hydroxyectoine, ectoine, homoectoine, betaine, L-carnitine, sarcosine, N,N-dimethylglycine, triethylammonium acetate, glycerol phosphate, N-(2-Hydroxy-1,1-bis(hydroxymethyl)ethyl)glycine (tricine), 3-(N-Morpholino)-2-hydroxypropanesulfonic acid (MOPSO), pentaerythritol, N-ethyl-N,N-bis-(2-hydroxyethyl)ammonium-N-4-butyl sulfonate, glycolic acid, lactic acid, malic acid, tartaric acid, 2-hydroxybutyric acid, 3-hy-droxybutyric acid, 4-amino-3-hydroxybutyric acid, pyridine 2,5-dicarboxylic acid, 3-(1-azoniabicyclo[2.2.2]oct-1-yl)propane-1-sulfonate, 1-(2-carboxylatoethyl)-1-azabicyclo[2.2.2]octan-1-ium, and 4-[benzyl(2-hydroxyethyl)methylazaniumyl]butane-1-sulfonate, and/or stabilizers such as those described in US/2008/0176209.

Stabilizers according to formulae (I)-(VII) include compounds of the following formulae:

(i) a compound of formula I:

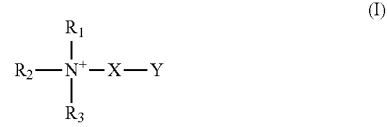

wherein $R_1$, $R_2$, $R_3$ are independently selected from —H, —$CH_3$ and —$CH_2$—$CH_3$, wherein when $R_1$ and $R_2$ are $CH_3$ or $CH_2$—$CH_3$, $R_3$ is either H or absent, wherein X is selected from —$CH_2$—, —$CH_2CH_2$—, —$CH_2CH_2CH_2$—, —$CH_2CH_2CH_2CH_2$—,

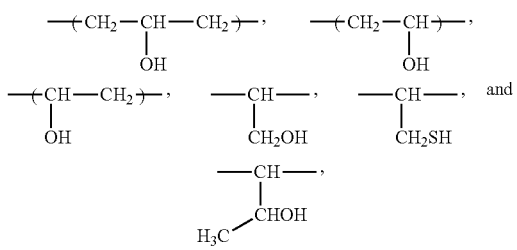

and wherein Y is selected from $COO^-$ and $SO_3^-$;

(ii) a compound of formula II:

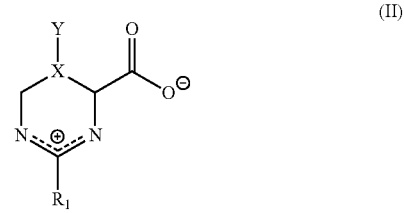

wherein $R_1$ is selected from $CH_3$ and $CH_2CH_3$, and wherein when X is CH, Y is selected from H and OH, and when X is $CH_2$—CH, Y is H;

(iii) a compound of formula III:

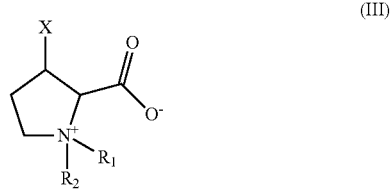

wherein $R_1$ and $R_2$ are independently selected from —H, —$CH_3$, and —$CH_2CH_3$, and wherein X is selected from H, OH and SH;

(iv) a compound of formula IV:

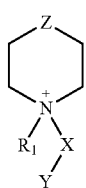

(IV)

wherein $R_1$ is selected from aryl, arylalkyl, —H, —CH$_3$—CH$_2$—CH$_3$, —CH$_2$CH$_2$OH, CH$_2$CHOHCH$_3$, CH$_2$CHOHCH$_2$OH, and CH$_2$CH$_2$CH$_2$OH, wherein X is selected from —CH$_2$—, —CH$_2$CH$_2$—, —CH$_2$CHOH, —CH$_2$CH$_2$CH$_2$—, CH$_2$CH$_2$CH$_2$CH$_2$, CH$_2$CHOHCH$_2$ and —CH$_2$CHOHCHOHCH$_2$—, wherein Y is selected from COO$^-$ and SO$_3^-$, and wherein Z is selected from —CH$_2$—, —CHOH—, O and S;

(v) a compound of formula V:

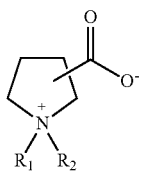

(V)

wherein $R_1$ and $R_2$ are each independently selected from aryl, arylalkyl, —H, —CH$_3$—CH$_2$—CH$_3$, —CH$_2$CH$_2$OH, CH$_2$CHOHCH$_3$, CH$_2$CHOHCH$_2$OH; and CH$_2$CH$_2$CH$_2$OH, (vi) a compound of formula VI:

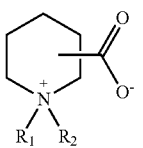

(VI)

wherein $R_1$ and $R_2$ are each independently selected from aryl, arylalkyl, —H, —CH$_3$—CH$_2$—CH$_3$, —CH$_2$CH$_2$OH, CH$_2$CHOHCH$_3$, CH$_2$CHOHCH$_2$OH, and CH$_2$CH$_2$CH$_2$OH;

(vii) a compound of formula VII:

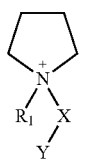

(VII)

wherein $R_1$ is selected from aryl, arylalkyl, —H, —CH$_3$—CH$_2$—CH$_3$, —CH$_2$CH$_2$OH, CH$_2$CHOHCH$_3$, CH$_2$CHOHCH$_2$OH, and CH$_2$CH$_2$CH$_2$OH, wherein X is selected from —CH$_2$—, —CH$_2$CH$_2$—, —CH$_2$CHOH, —CH$_2$CH$_2$CH$_2$—, —CH$_2$CH$_2$CH$_2$CH$_2$—, —CH$_2$CHOHCH$_2$—, and —CH$_2$CHOHCHOHCH$_2$—, wherein Y is selected from CO$_2^-$ and SO$_3^-$, and wherein Z is selected from CH$_2$, CHOH, O and S.

Syntheses of such stabilizers may be accomplished as disclosed herein using reagents that are commercially available (e.g., as described herein including in the Examples below, or using other reagents from SigmaAldrich or Fluka, or Carbopol® polymers from Noveon, Inc., Cleveland, Ohio, etc.) and/or according to established procedures, such as those found in *Fiesers' Reagents for Organic Synthesis* (T.-L. Ho (Ed.), Fieser, L. F. and Fieser, M., 1999 John Wiley & Sons, NY). A number of stabilizers as disclosed herein are commercially available, as will be appreciated by those familiar with the relevant art.

Certain embodiments disclosed herein contemplate as a stabilizer a zwitterionic compound that may be a betaine or betaine analogue or other zwitterionic compound including carboxylates and/or sulfonates, the preparation of which is described in "Betaine Analogues and Related Compounds for Biomedical Applications" (M. Vasudevamurthy, 2006 Doctoral Thesis, University of Canterbury, Christchurch, New Zealand). Certain other embodiments disclosed herein contemplate as a stabilizer a compound that may be a quinuclidine derivative or a 3-quinuclidinol derivative, for example, 3-(1-azoniabicyclo[2.2.2]oct-1-yl)propane-1-sulfonate and 1-(2-carboxylatoethyl)-1-azabicyclo[2.2.2]octan-1-ium, or other quinuclidine or quinuclidinol derivatives such as those described below, the preparation of which is described herein, and also including, for example, such derivatives which may be obtained by alkylation of a quinuclidine under reaction conditions such as those described hereinbelow.

"Alkyl" as used herein means a straight chain or branched, noncyclic or cyclic, unsaturated or saturated aliphatic hydrocarbon containing from 1 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Alkoxy" means an alkyl moiety attached through an oxygen bridge (i.e., —O-alkyl) such as methoxy, ethoxy, and the like.

"Alkylthio" means an alkyl moiety attached through a sulfur bridge (i.e., —S-alkyl) such as methylthio, ethylthio, and the like.

"Alkylsulfonyl" means an alkyl moiety attached through a sulfonyl bridge (i.e., —SO$_2$-alkyl) such as methylsulfonyl, ethylsulfonyl, and the like.

"Alkylamino" and "dialkylamino" mean one or two alkyl moieties attached through a nitrogen bridge (i.e., —N-alkyl) such as methylamino, ethylamino, dimethylamino, diethylamino, and the like.

"Aryl" means an aromatic carbocyclic moiety such as phenyl or naphthyl.

"Arylalkyl" means an alkyl having at least one alkyl hydrogen atom replaced with an aryl moiety, such as benzyl, —(CH$_2$)$_2$ phenyl, —(CH$_2$)$_3$ phenyl, —CH(phenyl)$_2$, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moeity, such as —CH$_2$ pyridinyl, —CH$_2$ pyrimidinyl, and the like.

"Halogen" means fluoro, chloro, bromo and iodo.

"Haloalkyl" means an alkyl having at least one hydrogen atom replaced with halogen, such as trifluoromethyl and the like.

"Heterocycle" (also referred to as a "heterocyclic ring") means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$ morpholinyl, and the like.

"Homocyclic" (also referred to herein as "homocyclic ring") means a saturated or unsaturated (but not aromatic) carbocyclic ring containing from 3-7 carbon atoms, such as cyclopropane, cyclobutane, cyclopentane, cyclohexane, cycloheptane, cyclohexene, and the like.

The term "substituted" as used herein means any of the above groups (e.g., alkyl, alkenyl, alkynyl, homocycle) wherein at least one hydrogen atom is replaced with a substituent. In the case of a keto substituent ("—C(═O)—") two hydrogen atoms are replaced. When substituted one or more of the above groups are substituted, "substituents" within the context of this invention include halogen, hydroxy, cyano, nitro, amino, alkylamino, dialkylamino, alkyl, alkoxy, alkylthio, haloalkyl, aryl, arylalkyl, heteroaryl, heteroarylalkyl, heterocycle and heterocyclealkyl, as well as —NR$_a$R$_b$, —NR$_a$C(═O)R$_b$—, NR$_a$C(═O)NR$_a$NR$_b$, —NR$_a$C(═O)OR$_b$—NR$_a$SO$_2$R$_b$, —C(═O)R$_a$, —C(═O)OR$_a$, —C(═O)NR$_a$R$_b$, —OC(═O)NR$_a$R$_b$, —OR$_a$, —SR$_a$, —SOR$_a$, —S(═O)$_2$R$_a$, —OS(═O)$_2$R$_a$ and —S(═O)$_2$OR$_a$. In addition, the above substituents may be further substituted with one or more of the above substituents, such that the substituent is substituted alkyl, substituted aryl, substituted arylalkyl, substituted heterocycle or substituted heterocyclealkyl. R$_a$ and R$_b$ in this context may be the same or different and independently hydrogen, alkyl, haloalkyl, substituted aryl, aryl, substituted aryl, arylalkyl, substituted arylalkyl, heterocycle, substituted heterocycle, heterocyclealkyl or substituted heterocyclealkyl.

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position. For example, in the following structure:

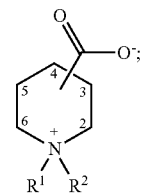

any carbon at positions 2, 3, 4, 5 and 6 of the piperidine ring may be substituted with a —C(O)O⁻ group, provided that only one —C(O)O⁻ substituent is on the piperidine ring. Ring atoms that are not substituted with the —C(O)O⁻ substituent are understood to be substituted with hydrogen, unless indicated otherwise. In those instances where the invention specifies that a non-aromatic ring is substituted with one or more functional groups, and those functional groups are shown connected to the non-aromatic ring with bonds that bisect ring bonds, then the functional groups may be present at different atoms of the ring, or on the same atom of the ring, so long as that atom could otherwise be substituted with a hydrogen atom.

According to certain embodiments as contemplated herein, there is provided a matrix for substantially dry storage of a biological sample which comprises a borate composition as provided herein and at least one stabilizer that is a quinuclidine derivative or a 3-quinuclidinol derivative that may be prepared according to the methods described herein. Exemplary quinuclidine or 3-quinuclidinol derivatives include: 4-(1-ammoniobicyclo[2.2.2]octan-1-yl)butanoate; 4-(1-ammoniobicyclo[2.2.2]octan-1-yl)butane-1-sulfonate; 3-(1-ammoniobicyclo[2.2.2]octan-1-yl)propane-1-sulfonate; 2-hydroxy-3-((1r,4r)-3-hydroxy-1-ammoniobicyclo[2.2.2] octan-1-yl)propane-1-sulfonate; 3-(-1-ammoniobicyclo [2.2.2]octan-1-yl)acetate; 3-(1-ammoniobicyclo[2.2.2]octan-1-yl)propanoate; 2-((1r,4r)-3-hydroxy-1-ammoniobicyclo[2.2.2]octan-1-yl)acetate; 3-((1s,4s)-3-hydroxy-1-ammoniobicyclo[2.2.2]octan-1-yl)propanoate; 4-((1s,4r)-3-hydroxy-1-ammoniobicyclo[2.2.2]octan-1-yl) butanoate; and 4-((1s,4r)-3-hydroxy-1-ammoniobicyclo [2.2.2]octan-1-yl)butane-1-sulfonate; such that the skilled person will recognize these and other quinuclidine and 3-quinuclidinol derivatives may be employed as stabilizers in the presently disclosed dry storage matrix compositions and their related methods of use.

The dissolvable/dissociable matrix may also be prepared in the sample storage device in a manner such that one or more wells contain at least one stabilizer, and in certain embodiments at least two stabilizers, which may include any agent that may desirably be included to preserve, stabilize, maintain, protect or otherwise contribute to the recovery from the biological sample storage device of a biological sample that has substantially the same biological activity as was present prior to the step of contacting the sample with the sample storage device. The stabilizer may in certain embodiments comprise a compound having a structure according to one of formulae (I)-(VII) or an osmoprotectant compound as described herein.

Stabilizers and osmoprotectant compounds may be used interchangeably and may also include organic solutes accumulated by cells/tissues in response to osmotic stress. In general, osmoprotectants increase thermodynamic stability of folded proteins and provide protection against denaturing stresses. Examples of osmolytes that act as such osmoprotectants include, but are not intended to be limited to, creatines, taurins, ectoins, their derivatives and corresponding biologically compatible salts such as hydroxyecotoine and homoectoine. Osmolytes are low molecular weight organic compounds with no net charge. These include zwitterionic compounds (compounds that contain charged species, but whose overall charge is zero due to equal numbers of positive and negative charges).

Additional examples of osmolytes contemplated for use in presently contemplated dry storage matrices, including use as stabilizers in combination with a borate composition as described herein, include, but are not limited to, sugars (e.g., sucrose, glucose, trehalose, fructose, xylose, mannitose, fucose), polyols (e.g., glycerol, mannitol, sorbitol, glycol, inositol), zwitterionic compounds (e.g., taurine), polyol sugars including myo-inositol and trehalose, polyunsaturated fatty acids including 3 fatty acid docosahexaenoic acid and eicosapentaenoic acid, free amino acids with no net charge (e.g., glycine, proline, valine, leucine, alanine, glutamine), derivatives of amino acids (e.g., glycine betaine, alternatively referred to as betaine), and trimethylamino N-oxide (TMAO). Betaine, betaine derivatives, and TMAO are examples of zwitterionic tetra-substituted amine derivatives, which are also contemplated as osmolytes for use in certain of the presently disclosed formulations. Preferred osmolytes include hydroxyectoine, ectoine, homoectoine, betaine, L-carnitine, sarcosine, N,N-Dimethylglycine, triethylammonium acetate, glycerol phosphate, tricine, MOPSO, pentaerythritol and N-ethyl-N,N-bis-(2-hydroxyethyl)ammonium-N-4-butyl sulfonate.

The addition of osmolytes often results in an observed increase in stability of the native structure for some proteins. The stabilization effect is observed with various osmolytes and small electrolytes such as sucrose, glycerol, trimethylamine N-oxide (TMAO), potassium glutamate, arginine and betaine (Wang et al., (1997) *Biochemistry* 36, 9101-9108; De-Sanctis et al. (1996) *J. Protein. Chem.* 15, 599-606; Chen et al., (1996) *J. Pharm. Sci.* 85, 419-426; Zhi et al., (1992) Protein Science 1, 552-529, the disclosures of which are incorporated herein by reference). This effect is based on the exclusion of osmolytes from hydration shells and crevices on protein surface (Timasheff (1992) *Biochemistry* 31, 9857-9864, the disclosure of which is incorporated herein by reference) or decreased solvation (Parsegian et al., (1995). *Methods. Enzymol.* 259, 43-94, the disclosure of which is incorporated herein by reference). In a series of quantitative studies, Wang and Bolen have shown that the osmolyte-induced increase in protein stability is due to a preferential burial of the polypeptide backbone rather than the amino acid side chains (Wang et al. (1997) *Biochemistry* 36, 9101-9108). Because native protein conformations are stabilized, proper folding reactions are also enhanced in the presence of osmolytes (Frye, K. J. and Royer, C. A. (1997) *Protein. Sci.* 6: 789-793; Kumar et al., (1998) *Biochem. Mol. Biol. Int.* 46, 509-517; Baskakov, I. and Bolen, D. W. (1998) *J. Biol. Chem.* 273: 4831-4834, the disclosures of which are incorporated herein by reference). Osmolytes usually affect protein stability and folding at physiological concentration range of 1-4 M (Yancey et al., (1982) *Science* 217, 1214-1222, the disclosure of which is incorporated herein by reference). However, it is apparent that the degree of stabilization depends on both the nature of the osmolyte and the protein substrate (Sola-Penna et al., (1997) *Eur. J. Biochem.* 248, 24-29, the disclosure of which is incorporated herein by reference) and, in some instances, the initial aggregation reaction can actually accelerate in the presence of osmolytes (Voziyan, P. A. and Fisher M. T. (2000) *Protein Science*, Volume 9, 2405-2412).

Osmolytes such as ectoine, glutamine, hydroxyectoine and betaine have been used to stabilize a variety of samples of biological origin for various uses. For example, DE-A-198 34 816 relates to the use of ectoine or ectoine derivatives in cosmetic formulations. It is disclosed that the mentioned compounds protect and stabilize nucleic acids of the human skin cells from physical, chemical and biological influences, such as radiation, especially ultraviolet radiation, denaturing substances, enzymes, especially endonucleases and restriction enzymes, and viruses, especially herpes viruses. U.S. Pat. No. 5,039,704 discloses a method of treating a catabolic dysfunction in an animal, wherein a therapeutically effective amount of glutamine or an analogue of glutamine is administered. U.S. Pat. No. 5,684,045 relates to the treatment of a catabolic gut-associated pathological process, especially intestinal mucosal and pancreatic atrophy, enhanced gut permeability and other diseases. These diseases are treated with a therapeutically effective amount of glutamine or an analogue thereof. U.S. Pat. No. 5,428,063 relates to a pharmaceutical composition in food supplements for the treatment or prevention of liver diseases. This involves the administration of high doses of betaine. U.S. Pat. No. 5,827,874 relates to the use of proline for the treatment of inflammations and pain, especially for the treatment of inflammatory conditions, rheumatic and non-rheumatic pain, and for post-surgical and post-traumatic pain. Knapp et al. in *Extremophiles* (1999), 3(3), 191-8, describe a temperature-stabilizing effect of compatible solutes. Ectoine, hydroxyectoine and betaine are mentioned. Sauer et al., *Biotechnology and Bioengineering* (1998), 57 (3), 306-13, disclose a temperature-stabilizing effect of the compatible solutes ectoine, hydroxyectoine and betaine. EP-A-0 915 167 relates to a method for the in-vivo recovery of components from cells by alternating conditions to which the cells are subjected. Ectoine and hydroxyectoine are described as an effective additive for the cryoprotection of biologically active substances. US 20050196824 relates to chaperonin and osmolyte protein folding and related screening methods.

Additional examples of stabilizing effects of hydroxyectoine include US 2003/0175232, US 2003/0157088 for use of hydroxyectoine in stabilizing enzymes in cosmetic products; US 2003/0199446 that discloses use of ectoin or ectoin derivatives for stabilizing p53 genes and gene products; WO/2004/112476 for use in reagents and methods for biomaterial preservation. Examples of the stabilizing effects of ectoine include U.S. Pat. No. 7,150,980 and US 2003/0138805 that discloses use of ectoine for use in methods for DNA amplification and sequencing by increasing the thermostability of DNA polymerases at elevated temperatures; U.S. Pat. No. 5,789,414 wherein ectoine is used to protect against freezing, drying and heating of pharmaceutical compositions; US 2003/0022148 and U.S. Pat. No. 6,475,716 that discloses ectoine as a biostabilizing substance for use in methods and reagents for organ preservation; and US 20080187924 describing methods for treatment of a sample containing biomolecules; and US 20020081565 that discloses use of ectoine as a stabilizer in the process of producing freeze dried competent cells and uses thereof. None of the disclosures cited above teaches or suggests the presently disclosed combinations of a borate composition and a stabilizer as described herein.

Other stabilizers contemplated for use according to certain embodiments disclosed herein may comprise an agent that is a biological inhibitor or a biochemical inhibitor, as provided herein. Accordingly, in certain embodiments the biological sample dry-storage matrix comprises at least one stabilizer that is such an inhibitor, for example, an anti-microbial agent such as (but not limited to) an anti-fungal and/or antibacterial agent capable of inhibiting or suppressing bacterial or fungal growth, viability and/or colonization, to inhibit microbial contamination of the wells and the stored sample during long-term storage. Stabilizers which may also be useful in the methods of this invention include polycations (see for example Slita et al., *J Biotechnol.* 2007 Jan. 20; 127(4):679-93. Epub 2006 Jul. 27), reducing agents (for example, dithiothreitol, 2-mercaptoethanol, dithioerythritol or other known thiol-active reducing agents, or the like); Scopes, R. K. 1994 *Protein Purification Principals and Practices.* Third edition, Springer, Inc., New York), steric stabilizers (such as alkyl groups, PEG chains, polysaccharides, alkyl amines; U.S. Pat. No. 7,098,033), amino acids and polyamino acids (see for example U.S. Pat. Nos. 7,011,825 and 6,143,817) including their derivatives (see for example U.S. Pat. No. 4,127,502), and buffers (Scopes, R. K. 1994 *Protein Purification: Principals and Practices.* Third edition, Springer, Inc., New York; Current Protocols, Protein Sciences, Cell Biology, Wiley and Sons, 2003). Non-limiting examples of amino acid stabilizers include serine, threonine, glycine, proline, carnitine, betaine and the like (see for example U.S. Pat. Nos. 7,258,873, 6,689,353 and 5,078,997). The stabilizer may in certain embodiments comprise a, a detergent, a polyol, an osmolyte, an organic solvent, an electrostatic reagent, a metal ion, a ligand, an inhibitor, a cofactor or substrate, a chaperonin, a redox buffer, disulfide isomerase or a protease inhibitor, which may facilitate dissolution of certain biological samples, such as proteins (see for example U.S. Pat. No. 6,057,159; Scopes, R. K. 1994 *Protein Purification: Principals and Practices.* Third edition, Springer, Inc., New York; Current Protocols, Protein Sciences, Cell Biology, Wiley and Sons, 2003).

Certain embodiments of the present invention are contemplated that expressly exclude particular dissolvable or dissociatable matrix materials such as soluble cationic polymers (e.g., DEAE-dextran) or anionic polymers (e.g., dextran sulphate) or agarose when used, absent other components of the herein described embodiments, with a di- or trisaccharide stabilizer (e.g., trehalose, lactitol, lactose, maltose, maltitol, sucrose, sorbitol, cellobiose, inositol, or chitosan) as disclosed for dry protein storage, for example, in one or more of U.S. Pat. No. 5,240,843, U.S. Pat. No. 5,834,254, U.S. Pat. No. 5,556,771, U.S. Pat. No. 4,891,319, U.S. Pat. No. 5,876,992, WO 90/05182, and WO 91/14773; and certain of the present embodiments may also expressly exclude the use of certain stabilizers that are disclosed in references cited above; but certain other embodiments of the present invention contemplate the use of such combinations of a dissolvable or dissociatable matrix comprising a borate composition and at least one stabilizer, including such first di- or trisaccharide stabilizer, along optionally with a second stabilizer that comprises a biological or biochemical inhibitor which may be a β-galactosidase inhibitor selected from the group consisting of D-galactono-1,4-lactone, L-arabinose, L-fucose, fructose, sucrose, D-galactose, dextrose, maltose, raffinose, xylose, melibiose, D-arabinose, cellobiose, D-glucose, and galactose. Certain other embodiments of the present invention contemplate the use of such combinations of a dissolvable or dissociatable matrix comprising a borate composition and at least one stabilizer (e.g., a compound of formula (I)-(VII) or an osmoprotectant compound) for substantially dry storage of biological samples other than proteins, for example, polynucleotides such as DNA, RNA, synthetic oligonucleotides, genomic DNA, natural and recombinant nucleic acid plasmids and constructs, and the like. Certain other embodiments of the present invention contemplate the use, for substantially dry storage of a biological sample as provided herein without refrigeration, of a matrix comprising a borate composition and at least one stabilizer that dissolves in a biocompatible solvent and which comprises a matrix material that dissolves in a biocompatible solvent and at least one stabilizer that dissolves in a biocompatible solvent.

As described herein, an added advantage of the herein described dissolvable matrix is that the storage container can be directly used as a reaction chamber after dissolving the matrix and rehydration of the material. The stability and activity of proteins in liquid form may be dependent on activity requirements such as pH, salt concentration, and cofactors. The stability of many proteins may in some cases be extremely labile at higher temperatures and the drying of proteins at ambient (e.g., room) temperature may therefore provide a stabilizing environment. Typically, in certain embodiments that relate to a dry-storable cell sample, the intact cell or virus may be present in an aqueous liquid that comprises a first solvent, for example as a cell or particle suspension or slurry that can be contacted with the matrix for substantially dry storage through the use of liquid handling instruments as appropriate for the type and quantity of cells or viruses to be stored.

Water comprises an exemplary first solvent and any of a number of aqueous liquids may be suitable aqueous liquids, such as well known buffered salt solutions, osmolar solutions or cell growth media including microbiological growth media (e.g., normal saline or physiological saline, phosphate-buffered saline, Tris, HEPES, carbonate, glycine or other buffered media, Hanks balanced salt solution, Ringer's solution, Luria broth, etc.), whereby following the step of contacting the sample with the matrix a step of drying is performed during which some or all of the solvent is removed. Preferably, the cell or virus is stored dry at room temperature for a period of time long enough to ensure subsequent recovery and isolation of nucleic acid when the step of redissolving or resuspending is performed, as opposed to recovery of viable cells or infectious viral particles (see, e.g., U.S. Ser. No. 11/291,267, which typically will involve dry storage periods of shorter duration), which as noted herein may vary as a function of the particular cell or virus type being stored and which in any event can be determined as described herein routinely through pilot studies in which various storage periods are employed and the recovered material is subsequently tested for nucleic acid recovery and/or residual cell viability.

The nucleic acid from the cell or virus is isolated following resuspending or redissolving of the dried sample. The solvent used for resuspending or redissolving the dried sample may be the same or different from the first solvent used to contact the sample with the storage matrix. Preferably, the solvent used to resuspend or redissolve the sample comprises an aqueous solvent, and more preferably the solvent used in the step of resuspending or redissolving to isolate nucleic acid is water. The isolated nucleic acid is in certain preferred embodiments DNA, and may be genomic DNA or plasmid DNA, depending on the source from which it is extracted (e.g. bacteria, virus, yeast, eukaryotic cell, etc.). As disclosed herein, following dry storage, and subsequent to resuspending or redissolving the composition that comprises the matrix material and the cell(s) or virus(es), thereby to isolate nucleic acid, the isolated nucleic acid is then ready for use, without the need for further purification, in downstream applications that may include, but need not be limited to, PCR amplification, cellular transformation, polynucleotide sequencing, rolling circle amplification, site-directed mutagenesis, T7 transcript generation, restriction enzyme analysis and other applications practiced by those skilled in the art (see for example, Maniatis, T. et al. 1982. *Molecular Cloning: A Laboratory Manual*, Cold Spring Harbor University Press, Cold Spring Harbor, N.Y.; Ausubel et al., 1993 *Current Protocols in Molecular Biology*, Greene Publ. Assoc. Inc. & John Wiley & Sons, Inc., Boston, Mass.).

As also described herein (including in the Examples) and in U.S. Application No. 20060099567, the presence of the dissacharide trehalose, believed to contribute to the stabilization of biological samples (e.g., Garcia de Castro et al., 2000 *Appl. Environ. Microbiol.* 66:4142; Manzanera et al., 2002 *Appl. Environ. Microbiol.* 68:4328), was not sufficient under certain conditions to support recovery of enzymatic activity in a protein following dry storage. As a brief background, trehalose is the natural substrate of trehalase, an enzyme that cleaves disaccharides. Trehalose is known to stabilize organic material such as proteins (e.g., PCT/GB86/00396), but when present under suboptimal conditions may be disadvantageous for longterm storage of proteins at ambient temperatures, since it is a natural energy source for fungi and bacteria.

Additional stabilizers contemplated for use according to certain other embodiments of the present invention may be present in a dry storage matrix but are not covalently linked to the polymeric matrix material as disclosed herein, and may include small molecules that comprise structures (i)-(xv), including several known amino acid side chains and mono-, di- and polysaccharides such as:

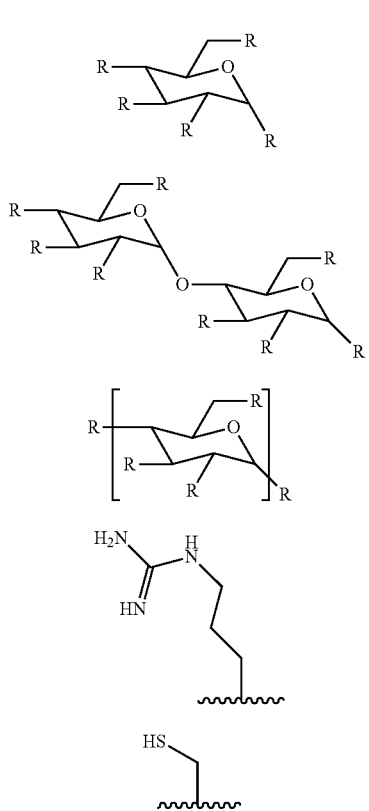

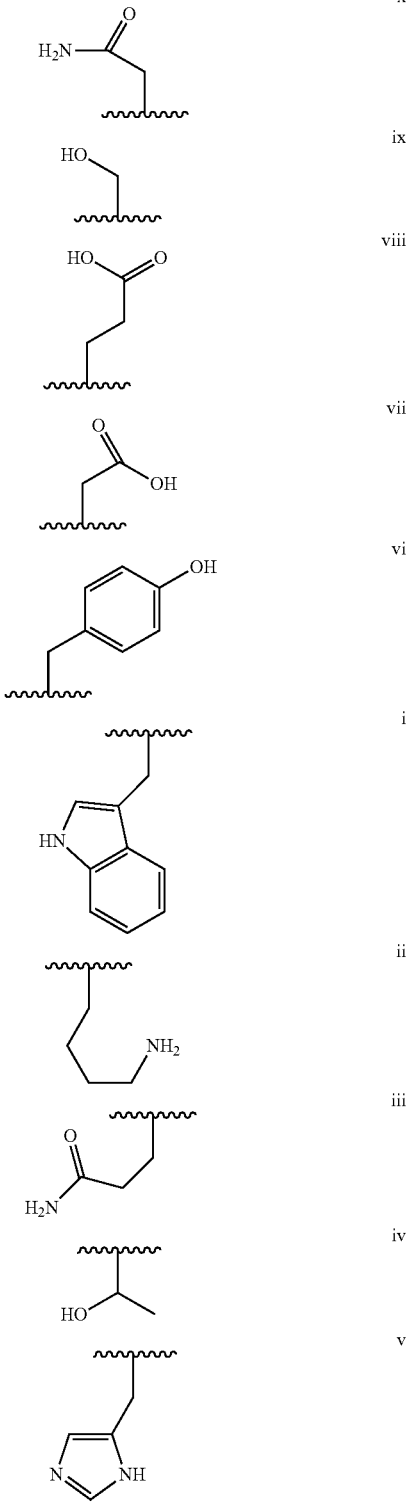

wherein R is selected from —H, —OH, —CH$_2$OH, —NHAc and —OAc. Such compositions are known in the art and are readily available from commercial suppliers.

In certain further embodiments at least one stabilizer may be selected from trehalose, lactitol, lactose, maltose, melezitose, maltitol, mannitol, gentibiose, raffinose, sucrose, sorbitol, cellobiose, melibiose, inositol, chitosan, hydroxyectoine, ectoine, homoectoine and/or, where, as also noted above, according to certain of such embodiments a chelator as described herein is also present to protect against metal ion contamination from the applied biological sample and additionally or alternatively according to certain other of such embodiments a herein disclosed matrix material is also present. The presently disclosed embodiments include several that contemplate the use, as modified according to the descriptions herein, of certain dry storage compositions of U.S. Pat. No. 5,240,843, U.S. Pat. No. 5,834,254, U.S. Pat. No. 5,556,771, U.S. Pat. No. 4,891,319, WO 87/00196, WO 89/00012, WO 89/06542, U.S. Pat. No. 5,876,992, U.S. Pat. No. 4,451,569, EP 0448146A1, WO 90/05182, and WO 91/14773, while certain other presently disclosed embodiments are contemplated that expressly exclude one or more components of the dry storage compositions of these publications.

Other exemplary stabilizers are commercially available and have structures that are well known, and include the following:

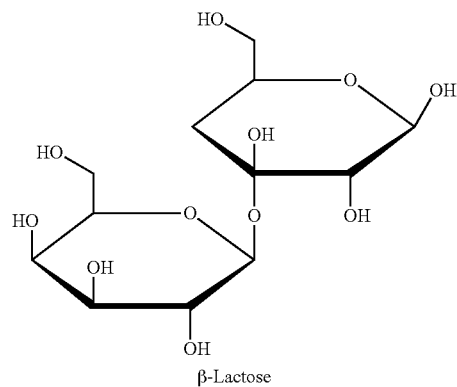

β-Lactose

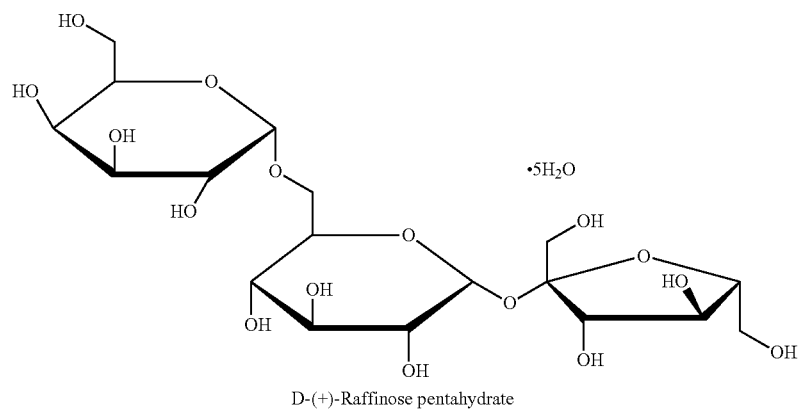

D-(+)-Raffinose pentahydrate

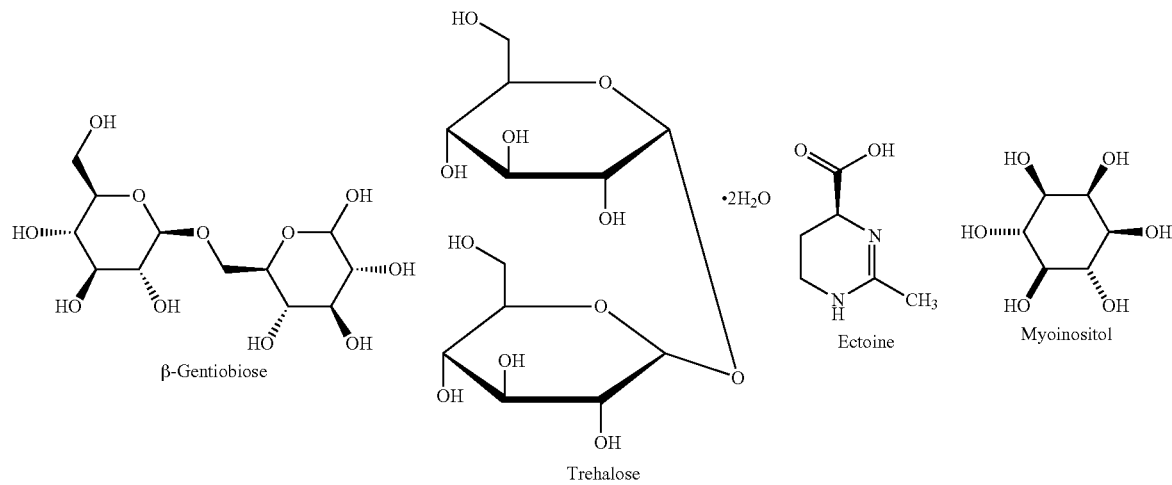

β-Gentiobiose

Trehalose

Ectoine

Myoinositol

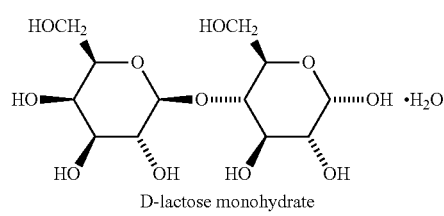
D-lactose monohydrate

-continued

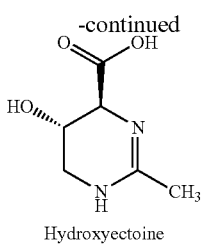
Hydroxyectoine

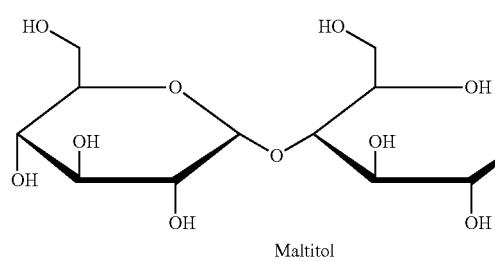
Maltitol

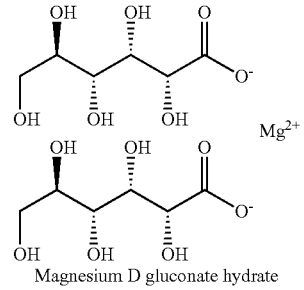
Magnesium D gluconate hydrate

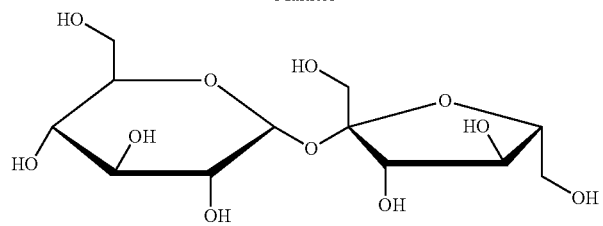
Sucrose

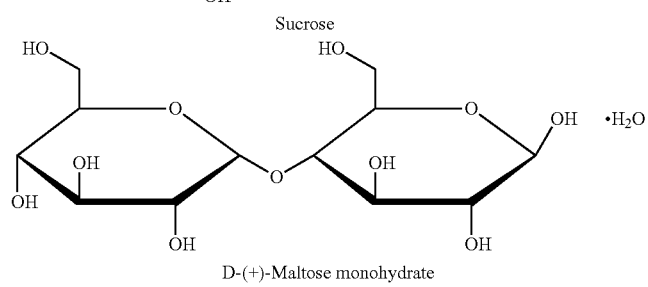
D-(+)-Maltose monohydrate

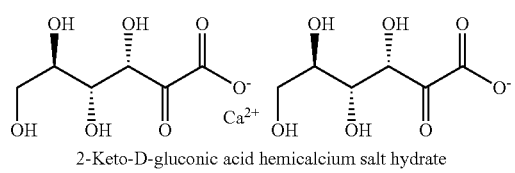
2-Keto-D-gluconic acid hemicalcium salt hydrate

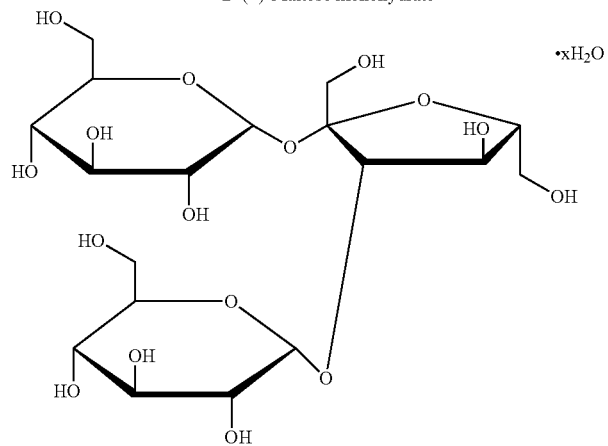
D(+)-Melezitose

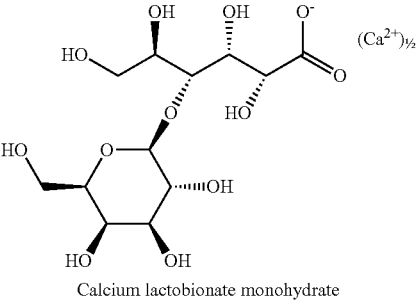
Calcium lactobionate monohydrate

⟨?⟩ indicates text missing or illegible when filed

Screening assays for identifying stabilizers are also provided by the present disclosure. More specifically, according to certain related embodiments, it is contemplated that the unexpected discovery disclosed herein, that biological activity of an isolated nucleic acid sample can be recovered following unrefrigerated substantially dry storage of the nucleic acid sample in a matrix that comprises a matrix material and a stabilizer, may be exploited to provide a method of identifying, from amongst one or a plurality of candidate agents, a stabilizer for stabilizing a substantially dry-storable nucleic acid sample as provided herein. Similarly, it is also contemplated that the surprising discovery as disclosed herein, that cellular nucleic acid can be readily recovered following unrefrigerated substantially dry storage of a cell sample prepared by drying a dry-storage matrix after contacting it with one or a plurality of isolated intact cells that contain nucleic acid (e.g., cellular nucleic acid), may be exploited to provide a method of identifying, from amongst one or a plurality of candidate agents, a stabilizer for stabilizing cellular nucleic acid in a substantially dry-storable cell sample as provided herein.

According to these and related embodiments, the dry-storage matrix may be prepared (i) with a known stabilizer as provided herein (e.g., as a positive control), or (ii) with one or more candidate stabilizers to prepare dry storage matrices to be tested for effectiveness of the candidate stabilizer(s) at contributing to the ability of biological activity of an isolated nucleic acid sample to be recovered from a resuspended or redissolved sample following unrefrigerated substantially dry storage of the sample, or (iii) with no stabilizer (e.g., as a negative control lacking any protective contribution from a stabilizer to retention of biological activity).

Following the steps of contacting the sample with each such matrix either in the presence or absence of a candidate agent (e.g., fluidly contacting an isolated nucleic acid with a matrix material that is dissolved or dissociated in a first biocompatible solvent; or contacting one or a plurality of isolated intact cells that contain nucleic acid with a matrix material that is dissolved or dissociated in a first biocompatible solvent), substantially drying the matrix, and maintaining the substantially dried matrix without refrigeration for at least one day, isolated nucleic acid may be recovered from each such sample as described herein, and the biological activity recovered from each dry-stored sample can be determined. Biological activity of the recovered nucleic acid from a sample that has been dried in the presence of a candidate stabilizer can be compared to that of a sample that has been dried in the absence of the stabilizer, such that as provided herein retention of substantially all activity by the sample dried with stabilizer present and substantial loss of activity by the sample dried in the absence of stabilizer, indicates the candidate agent acts as a stabilizer and has therefore been identified as such by the present method.

Detectable Indicator

Detectable indicators include compositions that permit detection (e.g., with statistical significance relative to an appropriate control, as will be know to the skilled artisan) or similar determination of any detectable parameter that directly relates to a condition, process, pathway, induction, activation, inhibition, regulation, dynamic structure, state, contamination, degradation or other activity or functional or structural change in a biological sample, including but not limited to altered enzymatic (including proteolytic and/or nucleolytic), respiratory, metabolic, catabolic, binding, catalytic, allosteric, conformational, or other biochemical or biophysical activity in the biological sample, and also including interactions between intermediates that may be formed as the result of such activities, including metabolites, catabolites, substrates, precursors, cofactors and the like.

A wide variety of detectable indicators are known to the art and can be selected for inclusion in the presently disclosed compositions and methods depending on the particular parameter or parameters that may be of interest for particular biological samples in particular sample storage applications. Non-limiting examples of parameters that may be detected by such detectable indicators include detection of the presence of one or more of an amine, an alcohol, an aldehyde, water, a thiol, a sulfide, a nitrite, avidin, biotin, an immunoglobulin, an oligosaccharide, a nucleic acid, a polypeptide, an enzyme, a cytoskeletal protein, a reactive oxygen species, a metal ion, pH, $Na^+$, $K^+$, $Cl^-$, a cyanide, a phosphate, selenium, a protease, a nuclease, a kinase, a phosphatase, a glycosidase, and a microbial contaminant, and others.

Examples of a broad range of detectable indicators (including colorimetric indicators) that may be selected for specific purposes are described in Haugland, 2002 *Handbook of Fluorescent Probes and Research Products—Ninth Ed.*, Molecular Probes, Eugene, Oreg.; in Mohr, 1999 *J. Mater. Chem.*, 9: 2259-2264; in Suslick et al., 2004 *Tetrahedron* 60:11133-11138; and in U.S. Pat. No. 6,323,039. (See also, e.g., Fluka Laboratory Products Catalog, 2001 Fluka, Milwaukee, Wis.; and Sigma Life Sciences Research Catalog, 2000, Sigma, St. Louis, Mo.) A detectable indicator may be a fluorescent indicator, a luminescent indicator, a phosphorescent indicator, a radiometric indicator, a dye, an enzyme, a substrate of an enzyme, an energy transfer molecule, or an affinity label. In certain preferred embodiments the detectable indicator may be one or more of phenol red, food dyes, ethidium bromide, dyes which do not appreciably interfere in quantitative PCR reactions, a DNA polymerase, an RNase inhibitor, a restriction endonuclease (e.g., a restriction enzyme used as a restriction nuclease such as a site- or sequence-specific restriction endonuclease), cobalt chloride (a moisture indicator that changes from blue color when water is present to pink when dry), Reichardt's dye (Aldrich Chemical) and a fluorogenic protease substrate.

According to certain embodiments herein described, drying the cells or viruses after the step of contacting with the dry-storage matrix can be performed at ambient temperatures on the lab bench, in a laminar flow hood, desiccating chamber, or under reduced atmospheric pressure including under vacuum (e.g. with vacuum pump such as a SpeedVac®). Other methods of drying are also contemplated and include for example without limitation, radiant heat drying, drying under a light source, desiccating, drying under nitrogen or other gas (e.g., preferably under a stream of a flowing inert gas), use of drying solvents or other chemicals, for example volatile organic solvents such as lower alcohols, lower alkanes and haloalkanes (e.g., pentanes, hexanes, methylene chloride, chloroform, carbon tetrachloride), ethers (e.g., tetrahydrofuran), ethyl acetate, acetonitrile, trifluoroacetic acid, pyridine, acetone or other solvents (where such solvents may in certain other embodiments comprise a second solvent in which a biological sample may be resuspended or redissolved), preferably in anhydrous form, air pressure, freeze-drying and other methods to facilitate and accelerate evaporation.

Drying of the sample can be determined by simple visual inspection or touch (i.e. tapping with a pipette tip) to ensure all moisture has been evaporated or removed; samples should not look or feel tacky from residual moisture). In some embodiments, a moisture indicator may be preferably included to ascertain a degree of drying has been achieved at which rehydration will effect nucleic acid isolation. For example, cobalt chloride may optionally be included as a detectable (by visible color-change or colorimetry) indicator of moisture content in a sample. A moisture indicator such as an electronic device that measures the dielectric content of material to determine moisture content (e.g. Aqua-Spear™, Mastrad Limited, Douglas, UK) is also contemplated for use in certain of these and related embodiments. A drying agent such as calcium sulfate (i.e. Drierite®, W.A. Hammond Drierite Co., Xenia, Ohio) or phosphorus pentoxide with a moisture indicator is also contemplated for use in certain embodiments of the present disclosure.

A detectable indicator in certain embodiments may comprise a polynucleotide polymerase and/or a suitable oligonucleotide, either or both of which may be employed as an indicator or, in certain other embodiments, as components of other nucleic acids-based applications of the compositions and methods described herein. Polymerases (including DNA polymerases and RNA polymerases) useful in accordance with certain embodiments of the present invention include, but are not limited to, *Thermus thermophilus* (Tth) DNA polymerase, *Thermus aquaticus* (Taq) DNA polymerase, *Thermologa neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu) DNA polymerase, DEEPVENT™ DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, mycobacterium DNA polymerase (Mtb, Mlep), and mutants, and variants and derivatives thereof. RNA polymerases such as T3, T5 and SP6 and mutants, variants and derivatives thereof may also be used in accordance with the invention.

Polymerases used in accordance with the invention may be any enzyme that can synthesize a nucleic acid molecule from a nucleic acid template, typically in the 5' to 3' direction. The nucleic acid polymerases used in the present invention may be mesophilic or thermophilic, and are preferably thermophilic. Preferred mesophilic DNA polymerases include T7 DNA polymerase, T5 DNA polymerase, Klenow fragment DNA polymerase, DNA polymerase III and the like. Preferred thermostable DNA polymerases that may be used in the methods of the invention include Taq, Tne, Tma, Pfu, Tfl, Tth, Stoffel fragment, VENT™ and DEEPVENT™ DNA polymerases, and mutants, variants and derivatives thereof (U.S. Pat. No. 5,436,149; U.S. Pat. No. 4,889,818; U.S. Pat. No. 4,965,188; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; WO 92/06188; WO 92/06200; WO 96/10640; Barnes, W. M., *Gene* 112:29-35 (1992); Lawyer et al., *PCR Meth. Appl.* 2:275-287 (1993); Flaman et al., *Nucl. Acids Res.* 22(15):3259-3260 (1994)).

Other detectable indicators for use in certain embodiments contemplated herein include affinity reagents such as antibodies, lectins, immunoglobulin Fc receptor proteins (e.g., *Staphylococcus aureus* protein A, protein G or other Fc receptors), avidin, biotin, other ligands, receptors or counterreceptors or their analogues or mimetics, and the like. For such affinity methodologies, reagents for immunometric measurements, such as suitably labeled antibodies or lectins, may be prepared including, for example, those labeled with radionuclides, with fluorophores, with affinity tags, with biotin or biotin mimetic sequences or those prepared as antibody-enzyme conjugates (see, e.g., Weir, D. M., *Handbook of Experimental Immunology*, 1986, Blackwell Scientific, Boston; Scouten, W. H., *Methods in Enzymology* 135:30-65, 1987; Harlow and Lane, *Antibodies: A Laboratory Manual*, Cold Spring Harbor Laboratory, 1988; Haugland, 2002 *Handbook of Fluorescent Probes and Research Products—Ninth Ed.*, Molecular Probes, Eugene, Oreg.; Scopes, R. K., *Protein Purification: Principles and Practice*, 1987, Springer-Verlag, NY; Hermanson, G. T. et al., *Immobilized Affinity Ligand Techniques*, 1992, Academic Press, Inc., NY; Luo et al., 1998 *J. Biotechnol.* 65:225 and references cited therein).

The dissolvable (or dissociable) matrix may be applied to storage containers, storage vessels or the like for biological samples, for example, by contacting or administering a matrix material that dissolves or dissociates in a solvent to one or a plurality of sample wells or vessels or the like of a storage device as described herein. For instance, the dissolvable matrix material may readily adhere to tubes and plates made of glass or plastic such as polypropylene, polystyrene or other materials. The dissolvable material is dried, which may by way of non-limiting illustration be accomplished by air drying at ambient temperature (typically within the range 20° C.-30° C. such as at 22° C., 23° C., 24° C., 25° C.) and/or at an appropriately elevated temperature, and/or under reduced atmospheric pressure (e.g., partial or full vacuum) and/or under a suitable gas stream such as a stream of filtered air, $CO_2$ or an inert gas such as nitrogen or other suitable drying gas, or by other drying means including lyophilization (i.e., freeze-drying under reduced pressure whereby frozen solvent sublimation to the gas phase transpires).

After the step of drying to achieve a matrix that is substantially dry, which may be complete drying (e.g., with statistical significance, all or substantially all detectable solvent has been removed) or, if desired, to achieve only partial drying, the dissolvable/dissociable matrix material is ready to accept the biological sample to be stored. In certain preferred embodiments a matrix that is substantially dry is provided for substantially dry storage of a biological sample, which includes storage of a matrix that has been combined with a sample and from which, with statistical significance, all or substantially all detectable solvent has been removed. Preferably and in certain embodiments which may vary according to the nature of the sample to be stored and its intended uses, greater than 75%, 80%, 82%, 84%, 86%, 88%, 90%, 91%, 92%, 93%, 94%, 95%, 96%, 97%, 98% or 99% of detectable solvent has been removed for purposes of substantially dry storage.

Biological material provided in or derived from a biological sample may also be added to the wells, tubes, vessels or the like in combination with the storage matrix in liquid form (e.g., by simultaneously contacting the sample well with the sample and the matrix dissolved or dissociated in a solvent), allowing the drying of the biological material and the matrix material to proceed at the same time, for example, to arrive at a matrix for substantially dry storage as provide herein. The dissolvable matrix does not, in preferred embodiments, interfere with biochemical reactions such that purification steps may not be required to separate the matrix from the biological sample prior to further processing of the sample, for instance, prior to performance of biochemical reactions, such as assays or the like, in the wells of the sample storage device.

For example, certain preferred embodiments as disclosed herein relate to a method for isolating a nucleic acid from a cell, wherein the cellular nucleic acid is DNA or RNA that is naturally occurring or the result of genetic engineering, the method comprising contacting a biological sample that comprises a cell with a dry-storage matrix in a container such as a sample well or vessel to obtain a composition comprising the matrix material and the cell; drying the container; maintaining the dried container (for instance, a dried sample well as part of a biological sample storage device that is maintained without refrigeration); and resuspending or redissolving the matrix material and the cell in a solvent, thereby isolating the nucleic acid. As described herein, these and related embodiments provide a surprisingly simple and fast method to isolate and recover from cells, with minimal manipulation, genomic (e.g., chromosomal) and epigenomic (e.g., plasmid) nucleic acid molecules, following unrefrigerated dry storage under conditions in which the nucleic acid molecules are unusually stable to temperature, ultraviolet radiation, and other potential environmental insults.

The buffer conditions in the dissolvable matrix may be adjusted such that greater than at least 70-75%, 75-80%, 80-85%, 85-90%, at least 90 percent, preferably greater than 95 percent, more preferably greater than 96, 97, 98 or 99 percent of the biological activity (e.g., enzymatic or affinity activity, or structural integrity or other biological activity as described herein and known to the art) of the biological sample is maintained upon solvent reconstitution (e.g., rehydration with water), eliminating the need to laboriously remove the sample from the storage container and transfer it to a reaction buffer in a separate container. Certain such invention embodiments correspondingly provide the unexpected advantage of eliminating the need to separately aliquot and/or calibrate certain biological reagents each time a stored sample is to be assayed.

Other non-limiting examples of matrix materials comprising a borate composition and at least one stabilizer as provided herein, that may be used in conjunction with dry storage matrix materials, including additional materials that comprise one or more of polycarbonate, cellulose (e.g., cellulose papers such as FTA™ paper, Whatman Corp., Florham Park, N.J.), cellulose acetate, cellulose nitrate, nitrocellulose, agarose, crosslinked agarose such as 2,3-dibromopropanol-crosslinked agarose, 3,6-anhydro-L-galactose, dextrans and other polysaccharides including chemically crosslinked polysaccharides such as epichlorohydrin-crosslinked dextran or N,N'-methylene bisacrylamide-crosslinked dextran, borosilicate microfiber glass, fiberglass, asbestos, polymers and plastics such as polypropylene, polystyrene, polyvinylidene fluoride (PVDF), nylon, polysulfone, polyethersulfone, polytetrafluoroethylene, and derivatives of these materials (e.g., U.S. Pat. No. 5,496,562) as well as other similar materials as are known in the art, or as can readily be determined to be suitable for use in the devices and methods described herein based on the present disclosure. See also, for example, U.S. Pat. No. 5,089,407, U.S. Pat. No. 4,891,319, U.S. Pat. No. 4,806,343, and U.S. Pat. No. 6,610,531.

The matrix material may be treated for the storage and preservation of biological materials. It is well documented that the adjustment of buffer conditions and the addition of chemicals and enzymes and other reagents can stabilize DNA and RNA (for example, Sambrook et al., 1989; Current Protocols, Nucleic Acid Chemistry, Molecular Biology, Wiley and Sons, 2003) and/or proteins, enzymes and/or other biological materials (for example, blood, tissue, bodily fluids) against degradation from enzymes, proteases and environmental factors (for example, Current Protocols, Protein Sciences, Cell Biology, Wiley and Sons, 2003). Matrix compositions for dry storage and methods for their use that combine certain chemical components to provide beneficial effects on the biological sample are also contemplated and may vary according to particular samples and uses thereof.

Various such chemical components and compounds may include but are not limited to a buffer capable of maintaining a desired pH level as may be selected by those familiar with the art, for example, buffers comprising Tris, Bis-Tris(Bis(2-hydroxyethyl)amino-2-(hydroxymethyl)-1,3-propanediol or 2,2-Bis(hydroxymethyl)-2,2',2''-nitrilotriethanol), citrate, acetate, phosphate, borate, HEPES, MES, MOPS, PIPES, carbonate and/or bicarbonate or other buffers (see, e.g., Calbiochem® Biochemicals & Immunochemicals Catalog 2004/2005, pp. 68-69 and pages cited therein, EMD Biosciences, La Jolla, Calif.) and suitable solutes such as salts (e.g., KCl, NaCl, $CaCl_2$, $MgCl_2$, etc.) for maintaining, preserving, enhancing, protecting or otherwise promoting one or more biological sample components (e.g., biomolecules), or activity buffers that may be selected and optimized for particular activities of specific biomolecules such as nucleic acid hybridization or activities of enzymes, antibodies or other proteins, or other buffers, for instance, Tris buffer (THAM, Trometanol, 2-amino-2-(hydroxymethyl)-1,3-propane diol), Tris-EDTA buffer (TE), sodium chloride/sodium citrate buffer (SSC), MOPS/sodium acetate/EDTA buffer (MOPS), ethylenediamine tetraacetic acid (EDTA), sodium acetate buffer at physiological pH, and the like.

Additional and/or exemplary pH buffers include CAPS (3-(Cyclohexylamino)-1-propanesulfonic acid), CAPSO (3-(Cyclohexylamino)-2-hydroxy-1-propanesulfonic acid), EPPS (4-(2-Hydroxyethyl)-1-piperazinepropanesulfonic acid), HEPES (4-(2-Hydroxyethyl)piperazine-1-ethanesulfonic acid), MES (2-(N-Morpholino)ethanesulfonic acid), MOPS (3-(N-Morpholino)propanesulfonic acid), MOPSO (3-Morpholino-2-hydroxypropanesulfonic acid), PIPES (1,4-piperazinediethanesulfonic acid), TAPS (N-[Tris(hydroxymethyl)methyl]-3-aminopropanesulfonic acid), TAPSO (2-Hydroxy-3-[tris(hydroxymethyl)methylamino]-1-propanesulfonic acid), TES (N-[Tris(hydroxymethyl)methyl]-2-aminoethanesulfonic acid), Bicine (N,N-Bis(2-hydroxyethyl)glycine), and Tricine (N-[Tris(hydroxymethyl)methyl]glycine).

Chelators may also be optionally included in dry storage matrices, for instance, ethylenediaminetetraacetic acid (EDTA), ethylene glycol tetraacetic acid (EGTA), diethylenetriaminepentaacetic acid (DTPA), trans-1,2-diaminocyclohexane-N,N,N',N'-tetraacetic acid (CDTA), 1,2-bis(2-aminophenoxy)ethane-N,N,N',N'-tetraacetic acid (BAPTA), 1,4,7,10-tetraazacyclododecane-1,4,7,10-tetraacetic acid (DOTA), N-(2-hydroxyethyl)ethylenediamine-N,N',N'-triacetic acid, and nitrilotriacetic acid (NTA).and other known chelators familiar to those skilled in the art, including salts thereof. For example, certain of the presently disclosed embodiments contemplate substantially drying a borate composition/stabilizer solution that includes a chelator, to obtain a matrix material for substantially dry storage of a biological sample, such as a solution that comprises about 1-50 mM sodium borate, about 1-50 mM tetraborate, about 10-100 mM hydroxyectoine, and about 0.05-0.5 mM EDTA, DTPA, EGTA or NTA.

Other chemical components that may be included in dry storage matrices include human placental ribonuclease inhibitor, bovine ribonuclease inhibitor, porcine ribonuclease inhibitor, diethyl pyrocarbonate, ethanol, formamide, guanidinium thiocyanate, vanadyl-ribonucleoside complexes, macaloid, proteinase K, heparin, hydroxylamine-oxygen-cupric ion, bentonite, ammonium sulfate, dithiothreitol (DTT), beta-mercaptoethanol or specific inhibiting antibodies.

Accordingly, certain invention embodiments contemplate a matrix for substantially dry storage of a biological sample, comprising a matrix material that dissolves or dissociates in a solvent, at least one stabilizer, and a sample treatment composition. The sample treatment composition may comprise an activity buffer as described below, and/or the sample treatment composition may comprise one or more of a cell lysis buffer, a free radical trapping agent, a sample denaturant, a solubilization agent, surfactant, and a pathogen-neutralizing agent. As provided by these embodiments, the dry storage matrix may thus comprise a set of components prepared to effect a desired treatment on a biological sample when the sample is introduced to the matrix, for example, in embodiments wherein the step of contacting the sample with the matrix occurs simultaneously with, or immediately prior to, rehydration or solvent reconstitution of the dried matrix. Moreover, in certain contemplated embodiments any buffer (including an activity buffer, a cell lysis buffer, etc.), additives, sample treatment composition or dry storage matrix described herein may be designed and/or configured such that after drying the storage matrix, only water may be added to obtain a functional, reconstituted biocompatible solvent from which to recover the biological sample.

An activity buffer may comprise a solvent or solution in liquid form, including a concentrate, or one or more dry ingredients which, when reconstituted with, dissolved in and/or diluted with one or more appropriate solvents (e.g., water typically, or additionally or alternatively, an alcohol such as methanol, ethanol, n-propanol, isopropanol, butanol, etc., an organic solvent such as dimethylsulfoxide, acetonitrile, phenol, chloroform, etc. or other solvent) as appropriate for the intended use, results in a liquid that is suitable for a desired use of the biological sample, such as a functional or structural characterization of one or more components of the sample.

Non-limiting examples of such uses may include determining one or more enzyme activities, determining intermolecular binding interactions, detecting the presence of a specific polynucleotide or amino acid sequence or of an immunologically defined epitope or of a defined oligosaccharide structure, detection of particular viruses or of microbial cells or of animal cells (including human), determining particular metabolites or catabolites, etc., all of which can be accomplished using methodologies and conditions that are defined and known to those skilled in the relevant art, including suitable conditions that can be provided through contacting the sample with an appropriate activity buffer.

A cell lysis buffer may be any composition that is selected to lyse (i.e., disrupt a boundary membrane of) a cell or organelle, and many such formulations are known to the art, based on principles of osmotic shock (e.g., hypotonic shock) and/or disruption of a cell membrane such as a plasma membrane through the use of a surfactant such as a detergent (e.g., Triton® X-100, Nonidet® P-40, any of the Tween® family of surfactants, sodium dodecyl sulfate, sodium lauryl sulfate, deoxycholate, octyl-glucopyranoside, betaines, or the like) and/or solute (e.g., urea, guanidine hydrochloride, guanidinium isothiocyanate, high salt concentration) system. Numerous cell lysis buffers are known and can be appropriately selected as a function of the nature of the biological sample and of the biomolecule(s), biological activities or biological structures that are desirably recovered, which may also in some embodiments include the selection of appropriate pH buffers, biological or biochemical inhibitors and detectable indicators.

Sample denaturants similarly may vary as a function of the biological sample and the dry storage matrix, but may include an agent that non-covalently alters (e.g., with statistical significance relative to an appropriate control such as an untreated sample) at least one of the three-dimensional conformation, quaternary, tertiary and/or secondary structure, degree of solvation, surface charge profile, surface hydrophobicity profile, or hydrogen bond-forming capability of a biomolecule of interest in the sample. Examples of sample denaturants include chaotropes (e.g., urea, guanidine, thiocyanate salts), detergents (e.g., sodium dodecyl sulfate), high-salt conditions or other agents or combinations of agents that promote denaturing conditions.

Free radical trapping agents for use in certain embodiments may include any agent that is capable of stably absorbing an unpaired free radical electron from a reactive compound, such as reactive oxygen species (ROS), for example, superoxide, peroxynitrite or hydroxyl radicals, and potentially other reactive species, and antioxidants represent exemplary free radical trapping agents. Accordingly a wide variety of known free radical trapping agents are commercially available and may be selected for inclusion in certain embodiments of the presently disclosed compositions and methods. Examples include ascorbate, beta-carotene, vitamin E, lycopene, tert-nitrosobutane, alpha-phenyl-tert-butylnitrone, 5,5-dimethylpyrroline-N-oxide, and others, as described in, e.g., Halliwell and Gutteridge (*Free Radicals in Biology and Medicine,* 1989 Clarendon Press, Oxford, UK, Chapters 5 and 6); Vanin (1999 *Meth. Enzymol.* 301:269); Marshall (2001 *Stroke* 32:190); Yang et al. (2000 *Exp. Neurol.* 163:39); Zhao et al. (2001 *Brain Res.* 909:46); and elsewhere.

As noted above, certain embodiments contemplate inclusion of a pathogen-neutralizing agent in the presently disclosed compositions and methods, which includes any agent that is capable of completely or partially, but in any event in a manner having statistical significance relative to an appropriate control, neutralizing, impairing, impeding, inhibiting, blocking, preventing, counteracting, reducing, decreasing or otherwise blocking any pathogenic effect of a pathogen such as a bacterium, virus, fungus, parasite, prion, yeast, protozoan, infectious agent or any other microbiological agent that causes a disease or disorder in humans or vertebrate animals. Persons familiar with the relevant art will recognize suitable pathogen-neutralizing agents for use according to the present disclosure. Exemplary agents include sodium azide, borate, sodium hypochlorite, hydrogen peroxide or other oxidizing agents, sodium dichloroisocyanurate, ethanol, isopropanol, antibiotics, fungicides, nucleoside analogues, antiviral compounds, and other microbicides; these or others may be selected according to the properties of the particular biological sample of interest.

As elaborated upon below, each well of a typical biological sample storage device in which the presently described dry storage matrix may be used holds about 5 µl to about 100, 200 or 300 µl of liquid sample material, preferably about 10 µl to about 30 µl of liquid sample material. Sample amounts can vary from about 0.01 µg to about 1000 µg of DNA, RNA, protein, blood, urine, feces, virus, bacteria, cells, tissue, cell extract, tissue extract, metabolites, chemicals, or other materials. Sample application is through direct application and can be automated. The applied wells may be provided with a detectable indicator such as a color indicator that changes color indicating an occupied well. Color change may be achieved by adding a color agent. For example, Ponceau red dye, Nitrazine yellow, Bromthymol Blue, Bromophenyl blue, Bromocresol Green, Methyl Orange, Congo red, Bromochlorophenol can be deposited with or prior to subsequent to the sample material, or by treating the matrix material before or after deposition of sample material into the well. A pH-dependent color reagent can be applied that changes color after deposition of a sample with a biological pH of 6.5 to 8.5 onto the matrix within the well. Applied wells dry within about 1 to about 20 minutes at ambient temperature or within about 0.1 to about 10 minutes at elevated temperature. DNA can be retrieved through re-hydration of the well for up to about 50 to about 80 times. The re-hydration reagent may be a solution or sample buffer, for example, one having a biological pH of 6.5-8.5, such as Tris buffer, Tris-EDTA buffer (TE), sodium chloride/sodium citrate buffer (SSC), MOPS/sodium acetate/EDTA buffer (MOPS), sodium acetate buffer, or another buffer as described herein and known in the art. The dry storage device design is applicable without further modifications for the storage of biological samples, including, for example, purified genomic DNA from bacterial, yeast, human, animals, plants and other sources. With additional modification, such as but not limited to coating the filters with denaturing agents for proteases, the dry storage device can be also used for bacteria, buccal swabs or samples, biopsy tissue, semen, urine, feces, blood, proteins and other samples.

Related embodiments are directed to kits that comprise the biological sample storage device as described herein, along with one or more ancillary reagents that may be selected for desired uses. Optionally the kit may also include a box, case, jar, drum, drawer, cabinet, carton, carrier, handle, rack, tray, pan, tank, bag, envelope, sleeve, housing or the like, such as any other suitable container. Ancillary reagents may include one or more solvents or buffers as described herein and known to the art, and may in certain embodiments include an activity buffer.

As used in this specification and the appended claims, the singular forms "a," "an" and "the" include plural references unless the content clearly dictates otherwise.

As used herein, in particular embodiments, the terms "about" or "approximately" when preceding a numerical value indicates the value plus or minus a range of 5%. In other embodiments, the terms "about" or "approximately" when preceding a numerical value indicates the value plus or minus a range of 10%. In yet other embodiments, the terms "about" or "approximately" when preceding a numerical value indicates the value plus or minus a range of 15%.

For example, in one embodiment, an oligonucleotide of approximately 20 nucleotides in length is equivalent to oligonucleotides that range from 19 to 21 nucleotides in length. In another embodiment, an oligonucleotide of approximately 20 nucleotides in length is equivalent to oligonucleotides that range from 18 to 22 nucleotides in length. In yet another embodiment, an oligonucleotide of approximately 20 nucleotides in length is equivalent to oligonucleotides that range from 17 to 23 nucleotides in length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are required and may or may not be present depending upon whether or not they affect the activity or action of the listed elements. As used herein, the term "each" when used in reference to a collection of items is intended to identify one or more individual items in the collection but does not necessarily refer to every item in the collection unless the content clearly dictates otherwise.

The practice of the present invention will employ, unless indicated specifically to the contrary, conventional methods of chemistry, biochemistry, organic chemistry, molecular biology, microbiology, recombinant DNA techniques, genetics, immunology, cell biology, stem cell protocols, cell culture and transgenic biology that are within the skill of the art, many of which are described below for the purpose of illustration. Such techniques are explained fully in the literature. See, e.g., Sambrook, et al., *Molecular Cloning: A Laboratory Manual* (3$^{rd}$ Edition, 2001); Sambrook, et al., *Molecular Cloning: A Laboratory Manual* (2$^{nd}$ Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-interscience; Glover, *DNA Cloning: A Practical Approach*, vol. I & II (IRL Press, Oxford, 1985); Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); Fire et al., *RNA Interference Technology: From Basic Science to Drug Development* (Cambridge University Press, Cambridge, 2005); Schepers, *RNA Interference in Practice* (Wiley-VCH, 2005); Engelke, *RNA Interference (RNAi): The Nuts & Bolts of siRNA Technology* (DNA Press, 2003); Gott, *RNA Interference, Editing, and Modification: Methods and Protocols* (Methods in Molecular Biology; Human Press, Totowa, N.J., 2004); Sohail, *Gene Silencing by RNA Interference: Technology and Application* (CRC, 2004); Clarke and Sanseau, *microRNA: Biology, Function & Expression* (Nuts & Bolts series; DNA Press, 2006); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and C C Blackwell, eds., 1986); Riott, *Essential Immunology*, 6th Edition, (Blackwell Scientific Publications, Oxford, 1988); *Embryonic Stem Cells: Methods and Protocols* (Methods in Molecular Biology) (Kurstad Turksen, Ed., 2002); *Embryonic Stem Cell Protocols Volume I: Isolation and Characterization* (Methods in Molecular Biology) (Kurstad Turksen, Ed., 2006); *Embryonic Stem Cell Protocols: Volume II: Differentiation Models* (Methods in Molecular Biology) (Kurstad Turksen, Ed., 2006); *Human Embryonic Stem Cell Protocols* (Methods in Molecular Biology) (Kurstad Turksen Ed., 2006); *Mesenchymal Stem Cells: Methods and Protocols* (Methods in Molecular Biology) (Darwin J. Prockop, Donald G. Phinney, and Bruce A. Bunnell Eds., 2008); *Hematopoietic Stem Cell Protocols* (Methods in Molecular Medicine) (Christopher A. Klug, and Craig T. Jordan Eds., 2001); *Hematopoietic Stem Cell Protocols* (Methods in Molecular Biology) (Kevin D. Bunting Ed., 2008) *Neural Stem Cells: Methods and Protocols* (Methods in Molecular Biology) (Leslie P. Weiner Ed., 2008); Hogan et al., *Methods of Manipulating the Mouse Embyro* (2$^{nd}$ Edition, 1994); Nagy et al., *Methods of Manipulating the Mouse Embryo* (3$^{rd}$ Edition, 2002), and *The zebrafish book. A guide for the laboratory use of zebrafish (Danio rerio)*, 4th Ed., (Univ. of Oregon Press, Eugene, Oreg., 2000).

All publications, patents and patent applications cited herein, whether supra or infra, are hereby incorporated by reference in their entirety.

EXAMPLES

Example 1

Preparation of Matrix for Biological Sample Storage

This example describes preparation of a dissolvable matrix comprising a borate composition and a stabilizer as provided herein, for storage of biological sample material, including unrefrigerated substantially dry storage. Unless otherwise noted, all reagents to which reference is made in these Examples were from Sigma-Aldrich (St. Louis, Mo.). 191 mg of sodium tetraborate decahydrate was placed in a 50 mL conical tube and then 158 mg of hydroxyectoine was added. RNase- and DNase-free 18.2 megaOhm water was added to bring the total volume to 50 mL. The mixture was stirred until the solids were completely dissolved.

The matrix in liquid form was applied to sample wells of a 96-well plate and dried completely at room temperature either under standard pressure or under vacuum in a vacuum chamber. The drying time for a 20-50 µl volume of the borate-stabilizer matrix was overnight, and under vacuum a shorter drying time was required. The plates were then ready for the storage of biological material.

Additional storage additives such as one or more of EDTA or other chelators known in the art and described herein (e.g., ethylenediaminetetraacetic acid (EDTA), ethylene glycol tetraacetic acid (EGTA), diethylenetriaminepentaacetic acid (DTPA), trans-1,2-diaminocyclohexane-N,N,N',N'-tetraacetic acid (CDTA), 1,2-Bis(2-aminophenoxy)ethane-N,N,N', N'-tetraacetic acid (BAPTA), 1,4,7,10-tetraazacyclododecane-1,4,7,10-tetraacetic acid (DOTA), N-(2-hydroxyethyl) ethylenediamine-N,N',N'-triacetic acid, and nitrilotriacetic acid (NTA), and salts thereof), Na-Acetate, cysteine, dithiothreitol (DTT, Cleland's reagent), potassium acetate, $K_2HPO_4$, glycerol, Triton X-100®, sodium dodecyl sulfate (SDS), sodium azide, protease inhibitors (e.g., PMSF, aminoethylbenzenesulfonyl fluoride, pepstatin, E64, bestatin, leupeptin, aprotinin), 2-mercaptoethanol, polyethylene glycol (PEG), bovine serum albumin (BSA), nicotinic adenine dinucleotide (NAD), ATP may also be added directly into the storage matrix for stabilization and activation after rehydration, depending on the biological sample to be stored and the bioactivity to be recovered and/or tested. For biological material associated with biological activity such as enzymes, the reaction conditions may be adjusted directly in the storage matrix. In some cases the only substance to be added for rehydration prior to an activity reaction is water. The matrix can also include one or more inhibitors such as antibacterial and/or antifungal agents. The borate-stabilizer dry storage matrix can be sterilized through sterile filtration or autoclaving prior to aliquoting the matrix into the individual storage wells. The autoclaved matrix is applied in aliquots to the storage wells either in single tubes or in multiwell plates at a liquid volume of 10 to 100l per well in the case of a 96-well plate.

Example 2

Dry Storage of Nucleic Acids

Biological sample storage devices were prepared with dried borate/hydroxyectoine matrices as described in Example 1. General molecular biology materials and methods were used, as described. (Sambrook et al., *Molecular Cloning: A Laboratory Manual*, Cold Spring Harbor Laboratories, Cold Spring Harbor, N.Y., 2001; Ausubel et al., 1993 *Current Protocols in Molecular Biology*, Greene Publ. Assoc. Inc. & John Wiley & Sons, Inc., Boston, Mass.). Stability tests were performed for plasmids, oligonucleotides, DNA fragments in the form of a 1 kB ladder, PCR products, genomic DNA (feline and human) and RNA. Recovery and stability tests were performed using electrophoretic gel-based, polymerase chain reaction (PCR), and transformation rate analyses.

A. Genomic Human DNA

A total of 100 ng of human genomic DNA (Novagen/EMD4 Biosciences, San Diego, Calif.) in Tris-EDTA (TE) buffer-pH 8 was applied directly into wells of a 96-well plate that either contained the borate/stabilizer matrix material or lacked any borate-stabilizer matrix (non-protected control sample). The borate composition matrix materials in different wells contained various amounts of different stabilizers as provided herein, including hydroxyectoine, ectoine, homoectoine, betaine, L-carnitine, sarcosine, N,N-Dimethylglycine, triethylammonium acetate, glycerol phosphate, tricine, MOPSO, pentaerythritol and N-ethyl-N,N-bis-(2-hydroxyethyl)ammonium-N-4-butyl sulfonate, prepared in 10 mM sodium tetraborate decahydrate or 10 mM sodium borate (prepared from boric acid). Identical aliquots were also distributed into empty wells of a second 96-well plate for storage at −20° C., for use as reference control samples. The genomic DNA was dried overnight and stored at room temperature. Control DNA samples were stored frozen at −20° C. The dried samples were then stored for 18 days at 85° C.

Following dry storage, wells containing the genomic human DNA were rehydrated with 10 µl water and then 5 µl was mixed with DNA electrophoretic gel loading buffer and applied to wells of an 0.8% agarose gel cast with ethidium bromide to assess the integrity of the recovered DNA following storage at elevated temperatures. PCR reactions contained 1×PCR buffer, 2 human (3-actin specific primers at a concentration of 10 µM and dNTPs, and were allowed to proceed for 15 minutes under standard conditions. The rehydrated reaction mixture was transferred into PCR tubes and Taq polymerase was added. The reaction was cycled for 35 cycles and analyzed on a 1% agarose gel. The fragment of the human β-actin gene of expected size (1.2 kb) was amplified without a decrease in amplification compared to frozen stored genomic DNA.

Example 3

Storage of Human Genomic DNA for Three Months at 85° C.

Human genomic DNA samples prepared as described in Example 2 were analyzed after 90 days of dry storage at 85° C. Samples were rehydrated with sample loading buffer and applied to an 0.8% agarose gel and electrophoresed at a constant 150 V for 40 min. Gel images were obtained using a KODAK-100 gel imager (Eastman Kodak, Rochester, N.Y.) using an ethidium bromide filter and excitation of the DNA bands with 302 nm UV light with exposure set at 0.15 seconds. Highly intact DNA was recovered from borate/stabilizer matrix-containing wells and could be observed migrating in gel electrophoresis with an apparent molecular mass greater than the 23 kb fragment of the reference standard DNA ladder for the samples with which the borate/stabilizer matrix was used to protect the DNA. Unprotected DNA (i.e., DNA that had been dry-stored in wells in the absence of any matrix) was degraded to the point where it could not be visualized by this method. Borate/stabilizer matrices protected DNA from degradation even after significantly longer (e.g., one-year) dry storage periods at 85° C. (Example 4, FIG. 2).

Example 4

Preparation and Use of Matrix for Unrefrigerated Dry Biological Sample Storage

This example describes preparation of the dissolvable matrix for storage of material. 191 mg of sodium tetraborate decahydrate was placed in a 50 mL conical tube and then 395 mg of hydroxyectoine was added. RNase- and DNase-free 18.2 MΩ water was added to bring the total volume to 50 mL for a final composition of 50 mM hydroxyectoine/10 mM sodium tetraborate decahydrate. The mixture was stirred until the solids were completely dissolved. Additional formulations were prepared as described above, containing 100, 25 or 10 mM hydroxyectoine in 10 mM sodium tetraborate decahydrate. All reagents were from Sigma-Aldrich (St. Louis, Mo.) unless otherwise noted.

Figure 2:
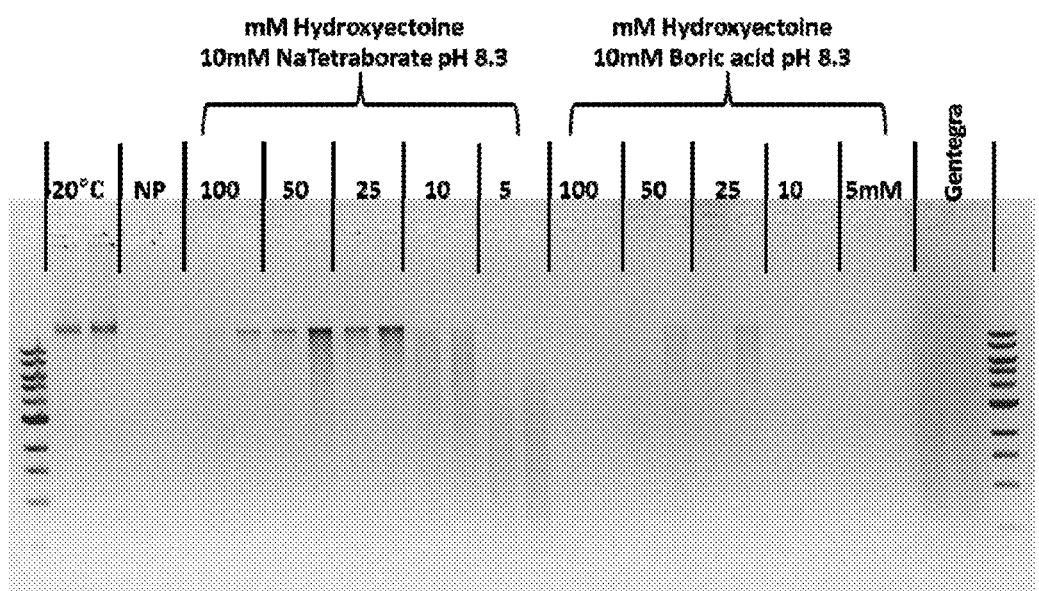
FIG. 2 shows an electrophoretogram of human genomic (293T cell) DNA samples following dry storage for one year at 85° C. on a borate/hydroxyectoine matrix of indicated composition, or in Gentegra™ tubes (Genvault, San Diego, Calif.) according to the manufacturer's instructions. Control lanes show DNA samples analyzed after −20° C. storage for a comparable time period (20° C.), and after one year at 85° C. in the absence of any protective dry storage matrix (NP). Outer lanes (unmarked) contain 1 kb ladder reference standard from New England Biolabs (Beverly, Mass.), in kb (from the top), 10, 8, 6, 5, 4, 3, 2, 1.5, 1.0, 0.5 kb.

The borate/hydroxyectoine compositions in liquid form were applied to sample wells of a 96 well SampleGard™ plate (Biomatrica Inc., San Diego, Calif.)), 20 L/well, and dried completely at room temperature overnight in a biological safety cabinet. Human genomic DNA isolated from 293T cells was diluted in NEB (New England Biolabs, Beverly, Mass.) DNase- and RNase-free water to give a final concentration of 5 µg/µL. 20 µL of the genomic DNA solution was applied to each matrix-containing well and also to several control wells that did not receive any of the borate/stabilizer matrix preservative composition. The solution in each well was mixed to ensure complete dissolution of the matrix (where present) and then the plate was allowed to dry overnight in a biological safety cabinet. Additionally, several 20 µL aliquots of DNA were placed into Axygen (Axygen Scientific, Inc., Union City, Calif.) DNAse-free sterile 1.7 mL microfuge tubes, closed and stored at −20° C. After drying the plates were transferred to a Thermo Scientific (ThermoFischer Scientific, Waltham, Mass.) oven set at 85° C. and stored there until removed for analysis by agarose gel electrophoresis. FIG. 2 shows the electrophoretic profile of DNA that was recovered after one year of dry storage at 85° C. on borate/stabilizer matrix material and analyzed after redissolving the contents of individual wells in 10 µL of gel loading buffer and applying the redissolved material to individual wells of a 0.8% agarose gel containing ethidium bromide. The gel was electrophoresed at a constant 150V for 45 min and imaged using UV transillumination at 302 nm on a KODAK 100 gel imager equipped with an ethidium bromide filter.

Example 5

Preparation of N-Ethyl-N,N-bis(2-hydroxyethyl) ammonium-4-butylsulfonate, an Exemplary Stabilizer This example describes synthesis of N-ethyl-N,N-bis(2-hydroxyethyl)ammonium-4-butylsulfonate, an exemplary stabilizer, according to the methodologies of M. Vasudevamurthy ("Betaine Analogues and Related Compounds for Biomedical Applications", Doctoral thesis, Univ. of Canterbury, Christchurch, New Zealand, 2006). 2.66 grams of N-ethyldiethanolamine (Sigma-Aldrich, cat #112062) was added to a 15 mL ace glass pressure tube that had been equipped with a stir bar. 2.72 g of 1,4-butane sultone (Sigma-Aldrich, cat #B85501) was added and the Teflon tube plug with o-ring was attached and tightened. The tube was mounted upright in a silicone oil bath and heated to 90° C. and held at 90° C. for 16 hours. The mixture was stirred until it became a solid mass. After 16 hours the tube was cooled and 10 mL of ethyl acetate was added. The solid mass was broken up using a stir bar and then filtered using a 30 mL medium porosity fritted glass funnel. The solid was washed 3× with 20 mL of ethylacetate and dried at 70° C. in a drying oven to give 4.864 g of N-ethyl-N,N-bis(2-hydroxyethyl)ammonium-4-butylsulfonate. The structure was confirmed by positive mode electrospray mass spectroscopy ESI/MS=290.1 m/z (M+Na), confirmed by $^1$H NMR.

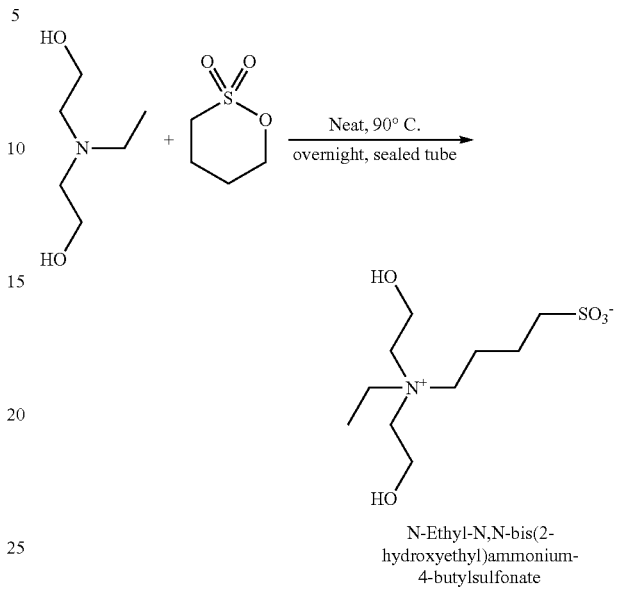

N-Ethyl-N,N-bis(2-hydroxyethyl)ammonium-4-butylsulfonate

Example 6

Preparation of Stabilizers

This example describes the synthesis and characterization of several exemplary stabilizers as provided herein.

Compound VIII

Synthesis of 1-ethyl-1-(4-sulfonatobutyl)piperidin-1-ium (VIII)

1.13 grams of N-ethylpiperidine was weighed into a 15 mL Ace Glass pressure tube containing a stir bar. 1.36 grams of was added dropwise to the pressure tube and the tube sealed with a teflon plug and o-ring. The tube was placed in a silicone oil bath and the temperature raised to 90° C. using a VWR heating stir plate (VWR Scientific, West Chester, Pa.) with temperature control and maintained at 90° C. After 16 hours the tube was allowed to cool to room temperature and 10 mL of ethyl acetate was added to the tube and the solid broken up using a spatula. The solid was collected by vacuum filtration using a medium porosity glass fritted funnel and washed with 30 mL of ethyl acetate. The solid was dried in a drying chamber containing Drierite® to give 1.59 g of a white solid.

Compound IX

Synthesis of 4-ethyl-4-(4-sulfonatobutyl)morpholin-4-ium

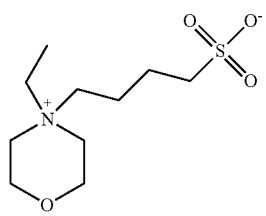

(IX)

1.15 grams of N-ethylmorpholine was alkylated with 1,4-butanesultone in similar fashion to the previous example to give 1.09 grams of a white solid. The structure was confirmed by positive mode electrospray mass spectroscopy (M+H)=252.6 and (M+Na) 274.2 m/z and $^1$H NMR.

Compound X

Synthesis of 3-(1-azoniabicyclo[2.2.2]oct-1-yl)propane-1-sulfonate

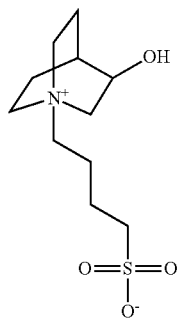

(X)

1.91 grams of 3-quinuclidinol was added to a 100 mL round bottom flask containing a stir bar. 50 mL of chloroform was added to the flask and mixture stirred to dissolve the quinuclidinol. The solution was cooled to near 0° C. in an ice bath. 1.83 grams of propane sultone was dissolved in 8 mL of chloroform in a test tube and then added dropwise to the solution of 3-quinuclidinol with stirring. During the addition of the propane sultone a white solid began to precipitate from solution. Following the addition the ice bath was removed and the solution allowed to warm to room temperature. The mixture was allowed to stir overnight then diluted with 50 ml of acetone and the solid collected on a fine porosity fritted glass funnel. The white precipitate was washed with 30 mL of acetone and the solid dried in a drying chamber containing Drierite® to obtain 3.42 g of a white solid. The structure was confirmed by positive mode electrospray mass spectrometry (M+Na)=286.2 and $^1$H NMR.

Compound XI

Synthesis of 1-(2-carboxylatoethyl)-1-azabicyclo[2.2.2]octan-1-ium

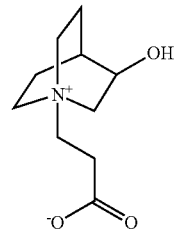

(XI)

1.91 grams of 3-quinuclidinol was added to a 100 mL round bottom flask containing a stir bar. 50 mL of dichloromethane was added to the flask and the mixture stirred to dissolve the quinuclidinol. 1.08 grams of acrylic acid was dissolved in 8 mL of dichloromethane in a test tube and then added dropwise to the solution of 3-quinuclidinol with stirring. The mixture was allowed to stir for 48 hours at room temperature during which time about half of the dichloromethane evaporated leaving a white slurry which was diluted with ethyl acetate and the solid collected in a medium porosity glass fritted funnel. The solid was washed with 30 mL of ethyl acetate and the resulting solid dried in a 85° C. drying oven to give 2.37 grams of a white solid. The structure was confirmed by positive mode electrospray mass spectrometry (M+H)=199.3 m/z and $^1$H NMR.

Compound XII

Synthesis of 4-[tris(2-hydroxyethyl)azaniumyl]butane-1-sulfonate

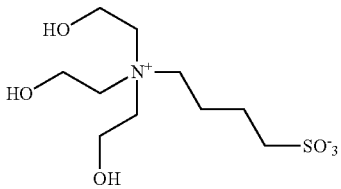

(XII)

1.49 grams of triethanolamine was added to a 100 mL round bottom flask equipped with a stir bar. 40 mL of dichloromethane was added to the flask and the mixture stirred thoroughly. The solution was cooled to near 0° C. using an ice water bath. 1.36 grams of 1,4-butanesultone was dissolved in 8 mL of dichloromethane and the butanesultone solution added dropwise to the stirred triethanolamine solution. Following complete addition the ice water bath was removed and the solution allowed to warm to room temperature. The mixture was stirred for 16 hours during which a flocculent precipitate formed. The solid was filtered using a medium porosity glass fritted funnel. The white solid was washed using 30 mL of ethyl ether and the solid dried in a dessicator over Drierite® to give 2.52 grams of a white solid. The structure was confirmed by positive mode electrospray mass spectometry (M+Na)=308.3 m/z and ¹H NMR.

Compound XIII

Synthesis of 4-[benzyl(2-hydroxyethyl)methylazaniumyl]butane-1-sulfonate

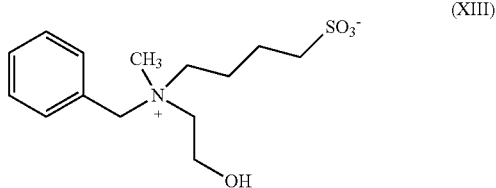

(XIII)

Compound XIII was synthesized in like manner to the example of Compound XI. 1.65 grams of N-benzyl-N-methylethanolamine was alkylated with 1.36 grams of 1,4-butanesultone to give 1.26 g of a white solid. The structure was confirmed by positive mode electrospray mass spectrometry (M+H)=302.4 m/z, (M+Na)=324.3 and ¹H NMR.

Example 7

Dry Storage of Nucleic Acids on Matrix Comprising Borate Composition and Zwitterionic Stabilizer This example shows characterization by quantitative polymerase chain reaction (qPCR) of DNA following dry storage in a borate-stabilizer matrix as disclosed herein, including a comparison of sample recovery following dry storage at 85° C. to sample recovery following dry storage at ambient (room) temperature.

The following compositions were prepared and spotted into a 96 well SampleGard™ (Biomatrica Inc., San Diego, Calif.) plate at 20 uL/well:

1=50 mM hydroxyectoine, 10 mM boric acid, 0.4 mM DTPA, pH 8.3.
2=50 mM hydroxyectoine, 10 mM boric acid, 1 mM sodium tetraborate, 0.4 mM DTPA, pH 8.3.
3=25 mM hydroxyectoine, 10 mM boric acid, 0.4 mM DTPA, pH 8.3.
4=25 mM hydroxyectoine, 10 mM boric acid, 1 mM sodium tetraborate, 0.4 mM DTPA, pH 8.3.

The plates were kept in the laminar flow hood and the solutions allowed to evaporate overnight. Genomic DNA isolated from human 293T cells was diluted to 1 ng/ul and then 10 uL applied to each well. The plates were mixed on a plate mixer for 10 min at 1000 rpm and then placed into a laminar flow hood and allowed to dry overnight. The next day one plate was placed in an 85° C. oven and the other kept at room temperature. The −20° C. controls were prepared by placing 10 uL of the 1 ng/uL stock of 293T DNA into DNAse-free microfuge tubes. The tubes were stored at −20° C., thawed and used at the respective time points. qPCR analysis was performed on an ABI 7300 instrument using ABI's TaqMan™ Universal PCR MasterMix™ according to the manufacturer's recommendations (ABI/Life Technologies, Carlsbad, Calif.). The default program was employed using the following primer and TaqMan™ probe:

```
beta actin Forward primer:
                                        [SEQ ID NO: 1]
5'TCA CCC ACA CTG TGC CCA TCT ACG A3' beta actin Reverse primer:
                                        [SEQ ID NO: 2]
5'CAG CGG AAC CGC TCA TTG CCA ATG G3' beta actin probe:
                                        [SEQ ID NO: 3]
5'(6-FAM)ATG CCT CCC CCA TGC CAT CCT GCG
T(BHQ1a-Q)3'
```

Figure 3:
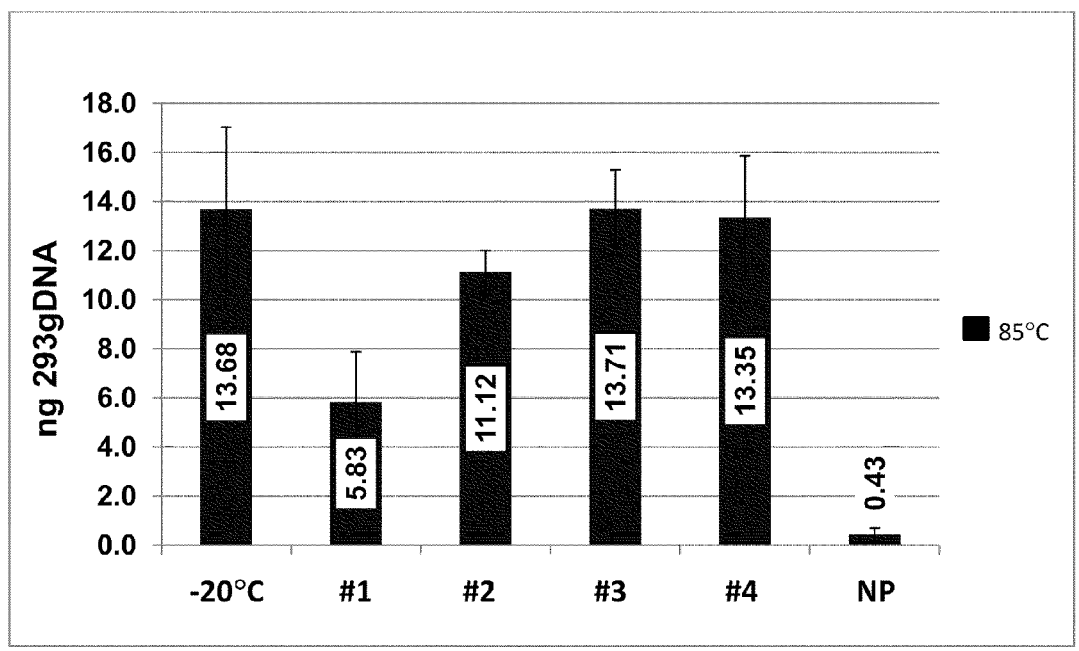
FIG. 3 summarizes DNA recoveries determined by quantitative PCR. Data were obtained using as PCR templates for each PCR reaction the DNA recovered following dry storage on the indicated dry storage matrix of 10 nanograms of DNA from HEK-293T cells for seven days at elevated temperature (85° C.). Set #1, dry storage matrix was prepared from 50 mM hydroxyectoine, 10 mM boric acid, 0.4 mM DTPA, pH 8.3; Set #2, 50 mM hydroxyectoine, 10 mM boric acid, 1 mM sodium tetraborate, 0.4 mM DTPA, pH 8.3; Set #3, 25 mM hydroxyectoine, 10 mM boric acid, 0.4 mM DTPA, pH 8.3; Set #4, mM hydroxyectoine, 10 mM boric acid, 1 mM sodium tetraborate, 0.4 mM DTPA, pH 8.3; NP, dry storage with no matrix material present; −20° C., data from control DNA samples analyzed after −20° C. storage for seven days.summarizes DNA recoveries determined by quantitative PCR. Data were obtained using as PCR templates for each PCR reaction the DNA recovered following dry storage on the indicated dry storage matrix of 10 nanograms of DNA from HEK-293T cells at ambient temperature (25° C.) for 10 days. Set #1, dry storage matrix was prepared from 50 mM hydroxyectoine, 10 mM boric acid, 0.4 mM DTPA, pH 8.3; Set #2, 50 mM hydroxyectoine, 10 mM boric acid, 1 mM sodium tetraborate, 0.4 mM DTPA, pH 8.3; Set #3, 25 mM hydroxyectoine, 10 mM boric acid, 0.4 mM DTPA, pH 8.3; Set #4, 25 mM hydroxyectoine, 10 mM boric acid, 1 mM sodium tetraborate, 0.4 mM DTPA, pH 8.3; NP, dry storage with no matrix material present; −20° C., data from control DNA samples analyzed after −20° C. storage for 10 days.
Figure 4:
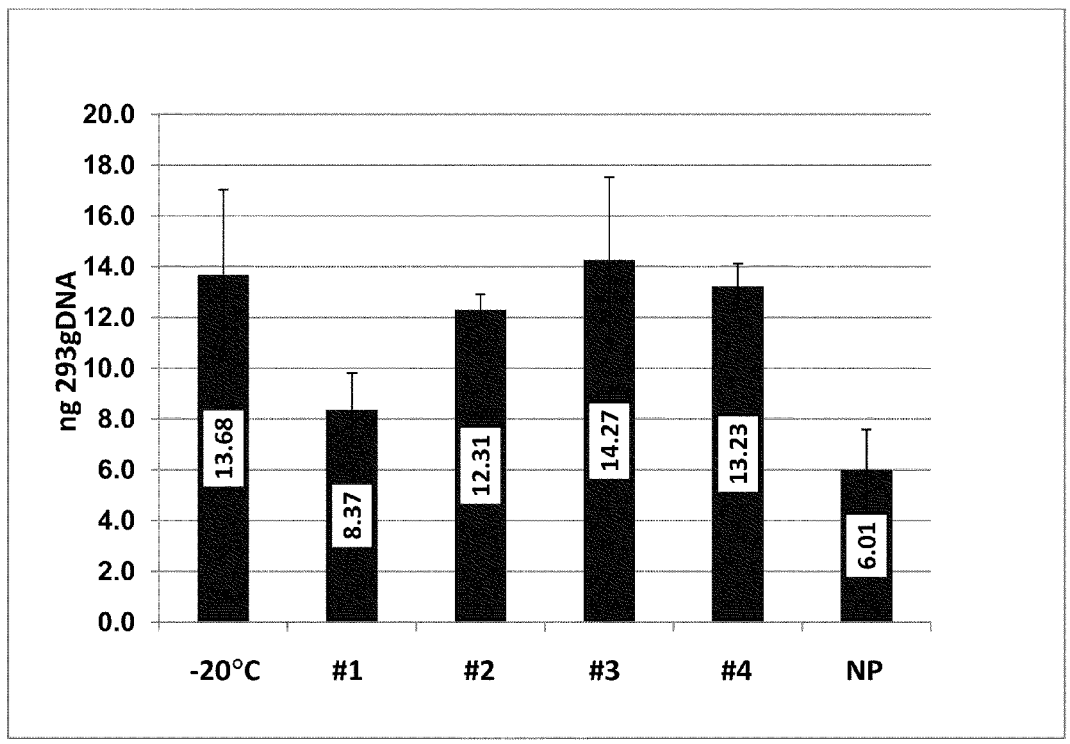
FIG. 4 summarizes DNA recoveries determined by quantitative PCR. Data were obtained using as PCR templates for each PCR reaction the DNA recovered following dry storage on the indicated dry storage matrix of 10 nanograms of DNA from HEK-293T cells at ambient temperature (25° C.) for 10 days. Set #1, dry storage matrix was prepared from 50 mM hydroxyectoine, 10 mM boric acid, 0.4 mM DTPA, pH 8.3; Set #2, 50 mM hydroxyectoine, 10 mM boric acid, 1 mM sodium tetraborate, 0.4 mM DTPA, pH 8.3; Set #3, 25 mM hydroxyectoine, 10 mM boric acid, 0.4 mM DTPA, pH 8.3; Set #4, 25 mM hydroxyectoine, 10 mM boric acid, 1 mM sodium tetraborate, 0.4 mM DTPA, pH 8.3; NP, dry storage with no matrix material present; −20° C., data from control DNA samples analyzed after −20° C. storage for 10 days.

Quantitative sample recoveries are depicted in FIGS. 3 and 4.

Example 8

Stabilization of RNA Extracted from 293T Cells

Various formulations of borate composition (inhibitor)/stabilizer (osmoprotectant) matrix materials were prepared according to Tables 1 and 2; where indicated the pH was adjusted with 1 N NaOH or 1 N HCl to achieve the final pH as shown below.

TABLE 1

Borate Composition/Stabilizer Combinations and Concentrations

| Sol'n | Stabilizer/Osmoprotectant | Inhibitor 1 | Inhibitor 2 | Final pH |
|---|---|---|---|---|
| 1 | 25 mM Hydroxyectoine | 25 mM Boric acid | None | |
| 2 | 50 mM Hydroxyectoine | 25 mM Boric acid | None | |
| 3 | 25 mM Hydroxyectoine | 25 mM Boric acid | 5 mM Sodium tetraborate | |
| 4 | 50 mM Hydroxyectoine | 25 mM Boric acid | 5 mM Sodium tetraborate | |
| 5 | 20 mM Malic acid | None | 10 mM Sodium tetraborate | 5.5 |
| 6 | 20 mM Dipicolinic acid | None | 10 mM Sodium tetraborate | 6.6 |

Figure 5:
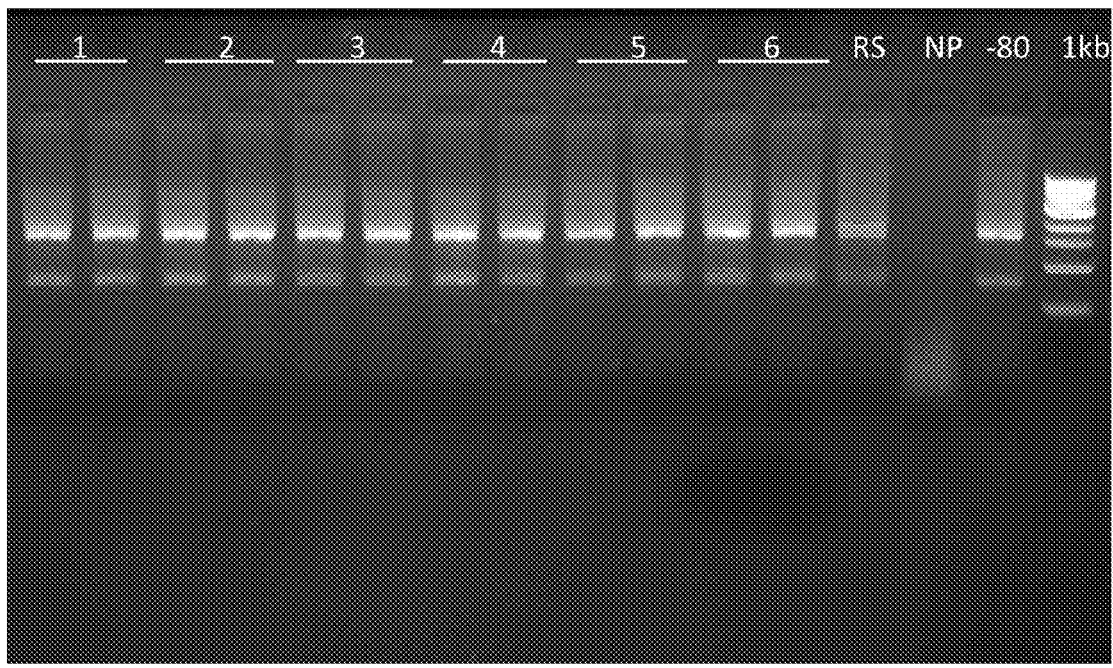
FIG. 5 shows an electrophoretogram of purified RNA samples recovered from borate-stabilizer storage matrices (lanes 1-6) following dry storage for 72 hours at 60° C. Control samples were dry-stored in the absence of borate-stabilizer matrix (NP) or at −80° C.

20 μL of each of the formulations shown in Table 1 were applied to each of 24 wells in SampleGard™ plates (Biomatrica Inc., San Diego, Calif.). The plates were kept in a laminar flow hood overnight to allow the matrix to dry. The next day the concentration of purified RNA was adjusted with RNase free water to give 27.5 ng of RNA/μL base of the absorbance at 260 nm. 20 μL of diluted RNA was spotted into each and mixed with the matrix for a total of 550 ng of RNA per well. The plates were kept in the laminar flow hood and allowed to dry overnight. The plates were transferred to a 60° C. Bender oven and maintained at 60° C. for three days prior to analysis. After 72 hours the samples were removed from the oven and rehydrated in 18 μL of gel loading buffer and applied to a 1.2% agarose gel prepared with 1×TAE buffer and containing 20 μg of ethidium bromide/100 mL of gel. The gel was electrophoresed for 40 min at a constant 150V and imaged on a UV light box equipped with a Kodak Gel-100 imager (FIG. 5).

TABLE 2

Additional Borate Composition/Stabilizer (Osmoprotectant) Combinations and Concentrations

| Sol'n | Stablilizer/ Osmoprotectant 1 | Inhibitor 1 | Stabilizer/ Osmoprotectant 2 | Final pH |
|---|---|---|---|---|
| 7 | 50 mM Hydroxyectoine | 10 mM Sodium tetraborate | 20 mM Dipicolinic acid | |
| 8 | 50 mM Hydroxyectoine | 10 mM Sodium tetraborate | 20 mM Malic acid | |
| 9 | 25 mM L-Carnitine | 25 mM Boric acid | | 5.8 |
| 10 | 25 mM Threonine | 25 mM Boric acid | | 5.6 |
| 11 | 40 mM Threonine | 10 mM Sodium tetraborate | | 6.6 |

Figure 6:
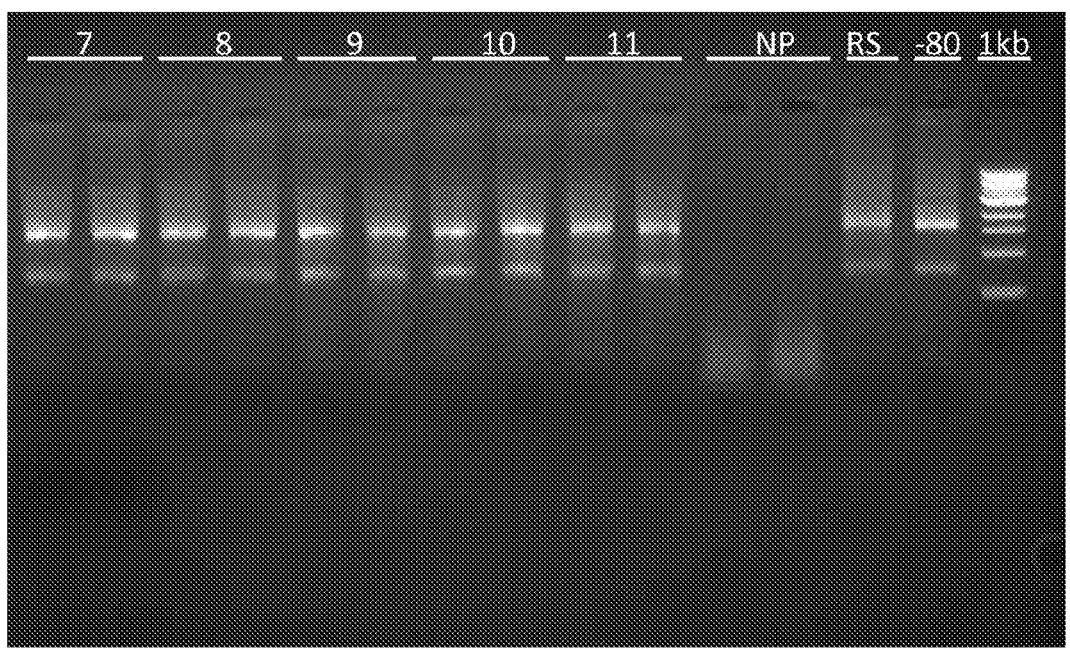
FIG. 6 shows an electrophoretogram of purified RNA samples recovered from borate-stabilizer storage matrices (lanes 7-11) following dry storage for 72 hours at 60° C. Control samples were dry-stored in the absence of borate-stabilizer matrix (NP) or at −80° C.

20 µL of each of the formulations shown in Table 2 were applied to each of 24 wells in SampleGard™ plates (Biomatrica Inc., San Diego, Calif.). The plates were kept in a laminar flow hood overnight to allow the matrix to dry. The next day the concentration of purified RNA was adjusted with RNase-free water to give 27.5 ng of RNA/µL base of the absorbance at 260 nm. 20 µL of diluted RNA was spotted into each and mixed with the matrix for a total of 550 ng of RNA per well. The plates were kept in the laminar flow hood and allowed to dry overnight. The plates were transferred to a 60° C. Bender oven and maintained at 60° C. for three days prior to analysis. After 72 hours the samples were removed from the oven and rehydrated in 18 µL of gel loading buffer and applied to a 1.2% agarose gel prepared with 1×TAE buffer and containing 20 µg of ethidium bromide/100 mL of gel. The gel was electrophoresed for 40 min at a constant 150V and imaged on a UV light box equipped with a Kodak Gel-100 imager (FIG. 6).

Example 9

Syntheses of Stabilizer Compounds

Synthesis of 4-(2-Ethoxy-2-oxoethyl)-4-methylmorpholin-4-ium bromide 3.0 g (29.6 mmol) of 4-methylmorpholine was dissolved in 50 mL dichloromethane and cooled to 0° C. in an ice bath. To this solution 5.0 g of ethyl bromoacetate (29.6 mmol) was added dropwise with continuous stirring and the mixture was then allowed to warm to room temperature. The clear solution started to form white precipitate after 5 minutes of stirring at room temperature. The resulting mixture was stirred for another 3 h. The precipitate was isolated by vacuum filtration using a 30 mL glass fritted funnel and washed 3 times with 30 mL of acetone to give 8.0 g of the product as a white solid. Positive mode ESI/MS: m/z=188 (M+, minus Br); confirmed by $^1$H NMR.

Synthesis of 2-(4-methylmorpholino-4-ium)acetate

To a solution of 4-(2-ethoxy-2-oxoethyl)-4-methylmorpholin-4-ium bromide, 1 (3.0 g, 11.2 mmol) in water (45 mL) was added conc. $H_2SO_4$ (1.0 mL). Dowex® (1×8, 200-400 mesh 'Cl') (3.0 g) was added to this solution. The resulting mixture was heated to reflux for 18 h. The resin was filtered off and the aqueous solution was concentrated. The resultant light yellow oil was triturated with isopropanol to afford 1.7 g, 95% yield of the desired product as white solid. Positive mode ESI/MS: m/z=160.1 (M+H); confirmed by $^1$H NMR.

Synthesis of 1-(2-Ethoxy-2-oxoethyl)-1-ethylpiperidinium bromide

To a solution of 1-ethylpiperidine (2.5 g, 22.1 mmol) in dichloromethane (4 mL) was added ethylbromoacetate (3.7 g, 22.1 mmol) via a syringe. The mixture was stirred at room temperature overnight. The resulting white precipitate was washed with hexane and ethylacetate to give 6.1 g, 98.6% yield of the product as a white solid. Positive mode ESI/MS: m/z=200.4 (M+, minus Br); confirmed by $^1$H NMR.

Synthesis of 2-(1-ethylpiperidinium-1-yl)acetate

To a solution of 1-(2-ethoxy-2-oxoethyl)-1-ethylpiperidinium bromide (3) (3.0 g, 10.7 mmol) in water (45 mL) was added conc. $H_2SO_4$ (1.0 mL). Dowex® (1×8, 200-400 mesh 'Cl') (3.0 g) was added to this solution. The resulting mixture was heated to reflux for 18 h. The resin was filtered off and the aqueous solution was concentrated. The resultant light yellow oil was triturated with isopropanol and did not form a precipitate. The yellow oil was dried under reduced pressure to give 1.6 g, 93% yield of the desired product as yellow oil. Positive mode ESI/MS: m/z=172.1 (M+H); confirmed by $^1$H NMR.

Synthesis of 3-(Ethoxycarbonyl)-1,1-dimethylpiperidinium iodide (11)

Ethylnipecotate (4.0 mL, 25.6 mmol) was added dropwise to a round bottom flask containing methyliodide (6.4 mL, 102.4 mmol) and 25 mL in an ice bath. The reaction mixture was stirred at room temperature overnight. The resulting precipitate was isolated by filtration. The precipitate was washed with dichloromethane several times to give 2.7 g, 34% yield of the desired product as a white solid. Positive mode ESI/MS: m/z=186.2 (M+, minus iodide); confirmed by $^1$H NMR

Synthesis of 1,1-Dimethylpiperidinium-3-carboxylate (12)

To a solution of 3-(ethoxycarbonyl)-1,1-dimethylpiperidinium iodide (5) (2.2 g, 6.9 mmol) in water (45 mL) was added conc. $H_2SO_4$ (1.0 mL). Dowex® (1×8, 200-400 mesh 'Cl') (2.0 g) was added to this solution. The resulting mixture was heated to reflux for 18 h. The resin was filtered off and the aqueous solution was concentrated. The resultant brown oil was triturated with isopropanol to form an off-white precipitate. The precipitate was washed with isopropanol until the color became white. The resulting white precipitate was dried under reduced pressure to give 1.0 g, 93% yield of the desired product. Positive mode ESI/MS: m/z=158 (M+H); confirmed by $^1$H NMR.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A matrix for substantially dry storage of a biological sample, comprising:

(a) a borate composition which comprises at least one compound selected from the group consisting of boric acid, boric anhydride, dihydrogen borate, hydrogen borate, diborate, triborate, tetraborate, metaborate, hydroxoborate (borax), borate salt, boric acid-glycerol and boric-acid-1,3 propanediol;

(b) at least one stabilizer that is selected from the group consisting of:

(ii)

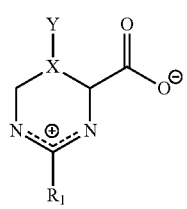

(II)

wherein $R_1$ is $CH_3$ or $CH_2CH_3$, and wherein when X is CH, Y is H or OH, and when X is $CH_2$—CH, Y is H;

(iv) a compound of formula IV:

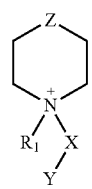

(IV)

wherein $R_1$ is selected from aryl, arylaklyl, —H, —$CH_3$— $CH_2$—$CH_3$, —$CH_2CH_2OH$, $CH_2CHOHCH_3$, $CH_2CHOHCH_2OH$, and $CH_2CH_2CH_2OH$, wherein X is selected from —$CH_2$—, —$CH_2CH_2$—, —$CH_2CHOH$, —$CH_2CH_2CH_2$—, $CH_2CH_2CH_2CH_2$, $CH_2CHOHCH_2$ and —$CH_2CHOHCHOHCH_2$—, wherein Y is selected from $COO^-$ and $SO_3^-$, and wherein Z is selected from —$CH_2$—, —$CHOH$—, O and S;

(vi) a compound of formula VI:

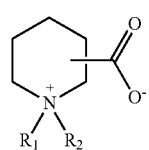

(VI)

wherein $R_1$ and $R_2$ are each independently selected from aryl, arylakyl, —H, —CH$_3$—-CH$_2$—CH$_3$, —CH$_2$CH$_2$OH, CH$_2$CHOHCH$_3$, CH$_2$CHOHCH$_2$OH, and CH$_2$CH$_2$CH$_2$OH;

wherein the borate composition and the stabilizer are present at a molar ratio that is selected from a molar ratio of from about 10:1 to about 1:10, a molar ratio of from about 5:1 to about 1:5, and a molar ratio of from about 20:1 to about 1:20, and wherein the matrix is capable of preventing degradation of an isolated DNA fragment of at least 10 kilobases during substantially dry storage of the DNA fragment in the matrix at 85° C. for a time period of at least two weeks.

2. The matrix of claim 1 wherein the biological sample comprises at least one of
(i) an isolated biomolecule that is selected from the group consisting of a nucleic acid, a protein, a polypeptide, a lipid, a glyconconjugate, an oligosaccharide, and a polysaccharide, and
(ii) a biological material that is selected from the group consisting of a mammalian cell, a bacterium, a yeast cell, a virus, a vaccine, blood, urine, a biological fluid, and a buccal swab.

3. The matrix of claim 1 wherein the biological sample comprises at least one isolated nucleic acid that is selected from DNA and RNA.

4. The matrix of claim 1 further comprising a biological inhibitor or biochemical inhibitor that is selected from the group consisting of a reducing agent, an alkylating agent, an antifungal agent and an antimicrobial agent.

5. A matrix for substantially dry storage of a biological sample, comprising:
(a) a borate composition which comprises at least one compound selected from the group consisting of boric acid, dihydrogen borate, hydrogen borate, diborate, triborate, tetraborate, metaborate, hydroxoborate (borax), borate salt, boric acid-glycerol, boric anhydride (B$_2$O$_3$) and boric-acid-1,3 propanediol;
(b) at least one stabilizer selected from the group consisting of hydroxyectoine, ectoine, homoectoine, betaine, L-carnitine, sarcosine, N,N-dimethylglycine, triethylammonium acetate, glycerol phosphate, tricine, MOPSO, pentaerythritol and N-ethyl-N,N-bis-(2-hydroxyethyl)ammonium-N-4-butyl sulfonate, glycolic acid, lactic acid, malic acid and tartaric acid; and
(c) a sample treatment composition, wherein the borate composition and the stabilizer are present at a molar ratio of from about 10:1 to about 1:10, and wherein the matrix is capable of preventing degradation of an isolated DNA fragment of at least 10 kilobases during substantially dry storage of the DNA fragment in the matrix at 85° C. for a time period of at least two weeks.

* * * * *

SEQUENCE LISTING

```
<160> NUMBER OF SEQ ID NOS: 3

<210> SEQ ID NO 1
<211> LENGTH: 25
<212> TYPE: DNA
<213> ORGANISM: Artificial Sequence
<220> FEATURE:
<223> OTHER INFORMATION: Primer Sequence

<400> SEQUENCE: 1
tcacccacac tgtgcccatc tacga                                25

<210> SEQ ID NO 2
<211> LENGTH: 25
<212> TYPE: DNA
<213> ORGANISM: Artificial Sequence
<220> FEATURE:
<223> OTHER INFORMATION: Primer Sequence

<400> SEQUENCE: 2
cagcggaacc gctcattgcc aatgg                                25

<210> SEQ ID NO 3
<211> LENGTH: 25
<212> TYPE: DNA
<213> ORGANISM: Artificial Sequence
<220> FEATURE:
<223> OTHER INFORMATION: Probe Sequence

<400> SEQUENCE: 3
atgcctcccc catgccatcc tgcgt                                25
```